US007928069B2

(12) United States Patent
Prestwich et al.

(10) Patent No.: US 7,928,069 B2
(45) Date of Patent: Apr. 19, 2011

(54) CROSSLINKED COMPOUNDS AND METHODS OF MAKING AND USING THEREOF

(75) Inventors: Glenn D. Prestwich, Salt Lake City, UT (US); Xiao Zheng Shu, Salt Lake City, UT (US); Yi Luo, Harriman, NY (US); Kelly R. Kirker, Salt Lake City, UT (US); Yanchun Liu, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 12/244,135

(22) Filed: Oct. 2, 2008

(65) Prior Publication Data

US 2009/0117078 A1 May 7, 2009

Related U.S. Application Data

(63) Continuation of application No. 12/234,445, filed on Sep. 19, 2008, which is a continuation of application No. 10/519,173, filed as application No. PCT/US03/15519 on May 15, 2003, now abandoned.

(60) Provisional application No. 60/390,504, filed on Jun. 21, 2002.

(51) Int. Cl.
*A61K 38/16* (2006.01)

(52) U.S. Cl. ...... 514/17.2; 514/21.2; 530/350; 530/353; 530/354; 530/356; 530/402; 530/345

(58) Field of Classification Search .................. 530/402, 530/345, 350, 353, 354, 356; 514/17.2, 21.2
See application file for complete search history.

(56) References Cited

U.S. PATENT DOCUMENTS

| | | | |
|---|---|---|---|
| 4,501,860 A | 2/1985 | Campbell et al. | |
| 4,507,413 A | 3/1985 | Thoma et al. | |
| 4,582,865 A | 4/1986 | Balazs et al. | |
| 4,644,059 A | 2/1987 | Gordon | |
| 4,713,448 A | 12/1987 | Balazs et al. | |
| 4,767,745 A | 8/1988 | Young et al. | |
| 4,851,121 A | 7/1989 | Yakota et al. | |
| 4,925,945 A * | 5/1990 | Klein et al. | 546/292 |
| 4,970,303 A * | 11/1990 | Reardan et al. | 536/124 |
| 5,135,919 A | 8/1992 | Folkman et al. | |
| 5,290,807 A | 3/1994 | Folkman et al. | |
| 5,443,953 A * | 8/1995 | Hansen et al. | 424/1.49 |
| 5,504,074 A | 4/1996 | D'Amato et al. | |
| 5,554,754 A | 9/1996 | Ravichandran et al. | |
| 5,616,568 A | 4/1997 | Pouyani et al. | |
| 5,635,603 A * | 6/1997 | Hansen et al. | 530/391.5 |
| 5,639,725 A | 6/1997 | O'Reilly et al. | |
| 5,652,347 A | 7/1997 | Pouyani et al. | |
| 5,661,143 A | 8/1997 | D'Amato et al. | |
| 5,698,586 A | 12/1997 | Kishimoto et al. | |
| 5,733,876 A | 3/1998 | O'Reilly et al. | |
| 5,762,918 A * | 6/1998 | Thorpe | 424/78.17 |
| 5,792,845 A | 8/1998 | O'Reilly et al. | |
| 5,837,682 A | 11/1998 | Folkman et al. | |
| 5,854,205 A | 12/1998 | O'Reilly et al. | |
| 5,854,221 A | 12/1998 | Cao et al. | |
| 5,861,372 A | 1/1999 | Folkman et al. | |
| 5,874,417 A | 2/1999 | Prestwich et al. | |
| 5,885,795 A | 3/1999 | O'Reilly et al. | |
| 5,892,069 A | 4/1999 | D'Amato et al. | |
| 5,945,403 A | 8/1999 | Folkman et al. | |
| 6,017,954 A | 1/2000 | Folkman et al. | |
| 6,024,688 A | 2/2000 | Folkman et al. | |
| 6,086,865 A | 7/2000 | Folkman et al. | |
| 6,174,861 B1 | 1/2001 | O'Reilly et al. | |
| 6,310,039 B1 | 10/2001 | Kratz | |
| 6,649,742 B1 | 11/2003 | Better et al. | |
| 6,664,372 B1 | 12/2003 | Janda et al. | |
| 6,825,269 B1 | 11/2004 | Gottschall | |
| 2005/0176620 A1 | 8/2005 | Prestwich et al. | |
| 2006/0205674 A2 | 9/2006 | Satyam | |
| 2009/0105193 A1 | 4/2009 | Prestwich et al. | |

FOREIGN PATENT DOCUMENTS

| | | |
|---|---|---|
| WO | WO 96/33750 | 10/1996 |
| WO | WO 98/22114 A1 | 5/1998 |
| WO | WO 00/16818 A1 | 3/2000 |
| WO | WO 02/06373 A1 | 1/2002 |
| WO | WO 02/41877 | 5/2002 |

OTHER PUBLICATIONS

Zara, Jane J. (Analytical Biochemistry 194(1), 156-62, 1991).*
Carlsson, Biochemical Journal 173, 723-37, 1978.*
Shu, Biomacromolecules 3, 1304-1311, 2002.*
Abstract of EP 0,339,264 (Nov. 1989).*
Definition of "Viscosupplementation", from The Free Dictionary [online], retrieved on Oct. 7, 2010, 1 page, http://medical-dictionary.thefreedictionary.com/viscosupplementation.
Wen, "Intra-articular hyaluronic acid injections for knee osteoarthritis", American Family Physician Online Article, pp. 1-6 (2000) http://www.aafp.org/afp/20000801/565.html.
Agren et al., "Developmentally programmed expression of hyaluronan in human skin and its appendages", *J. Invest. Dermatol.*, 109:219-224 (1997).
Aigner et al., "Cartilage tissue engineering with novel nonwoven structured biomaterial based on hyaluronic acid benzyl ester", *J. Biomed. Mater. Res.*, 42:172-181 (1998).
Anseth and Bryant, "The effects of scaffold thickness on tissue engineered cartilage in photocrosslinked poly(ethylene oxide) hydrogel", *Biomaterials* 22:619-626 (2001).
Anseth et al., "In situ forming degradable networks and their application in tissue engineering and drug delivery", *J. Control. Release*, 78:199-209 (2002).
Arnold et al., "Evaluation of resorbable barriers for preventing surgical adhesions", *Ferl. Steril.*, 73:157-161 (2000).

(Continued)

*Primary Examiner* — David Lukton
(74) *Attorney, Agent, or Firm* — Susan T. Evans; King & Spalding LLP

(57) ABSTRACT

Described herein are crosslinked compounds useful in numerous treatments. Described herein are methods of making crosslinked compounds via (1) die oxidative coupling of two or more thiol compounds or (2) by the reaction between at least one thiol compound with at least one thiol-reactive compound.

9 Claims, 18 Drawing Sheets

OTHER PUBLICATIONS

Band, P.A., "Hyaluronan derivatives: Chemistry and clinical applications. In: Laurent TC, editor The chemistry, biology and medical applications of hyaluronan and its derivatives", London: Portland Press, p. 33-42. (1998).

Barbucci et al., "Synthesis, chemical and theological characterization of new hyaluronic acid-based hydrogels", *Biomater. Sci. Polym. Ed.*, 11:383-99 (2000).

Belluco et al., "Prevention of postsurgical adhesions with an autocrosslinked hyaluronan derivative gel", *J. Surg. Res.*, 100:217-21 (2001).

Benedetti et al., "Biocompatibility and biodegradation of different hyaluronan derivatives (Hyaff) implanted in rats", *Biomaterials*, 14:1154-160 (1993).

Benedetti et al., "Microspheres of hyaluronic acid esters—fabrication methods and In vitro hydrocortisone release", *J. Controlled Rel.*, 13:33-41 (1990).

Benesch and Benesch, "Thiolation of protein", *Proc Nat Acad Sci USA*, 44:848-53 (1958).

Bitter and Muir, "A modified uronic acid carbozole reaction" *Anal. Biochem.*, 4:330-34 (1962).

Boyce et al., "Comparative assessment of cultured skin substitutes and native skin autograft for treatment of full-thickness burns", *Ann. Surg.*, 222:743-52 (1995).

Boyce et al., "Hyaluronic acid induces tumour necrosis factor-a production by human macrophages in vitro", *British J. Plast. Surg.*, 50:362-68 (1997).

Boyce et al., "Reduced wound contraction after grafting of full-thickness burns with a collagen and chondroitin-6-sulfate (GAG) dermal skin substitute and coverage with biobrane", *J. Burn Care Rehabil.*, 9:364-70 (1988).

Boyce et al., "Skin anatomy and antigen expression after burn wound closure with composite grafts of cultured skin cell and biopolymers", *Plast. Reconstr. Surg.*, 91:632-41 (1993).

Brown et al. (1999) Absorption of hyaluronan applied to the surface of intact skin. J. Invest. Dermatol. 113:740-746 (1999).

Brown et al., "Enhancement wound healing by topical treatment with epidermal growth factor", *New Engl. J. Med.*, 321:76-79 (1989).

Brun et al., "In vitro reconstructed tissues on hydroluronan-based temporary scaffolding", *J. Mater. Sci. Mater. Med.*, 10:683-88 (1999).

Bulpitt and Aeschllmann, "New strategy for chemical modification of hyaluronic acid: Preparation of functionalized derivatives and their use in the formation of novel biocompatible hydrogels", J. Biomed. Mater. Res., 47:152-69 (1999).

Burdick and Anseth, "Photoencapsulation of osteoblasts in injectable RGD-modified PEG hydrogel for bone tissue engineering", Biomaterials, 23:4315-23 (2002).

Burns at al., "A hyaluronate based gel for the prevention of postsurgical adhesions: Evaluation in two animal species", Fertil, Steril., 66:814-821 (1996).

Burns et al., "Preclinical evaluation of Seprafilm bioresorbable membrane", *Eur. Surg. Suppl.*, 577:40-48 (1997).

Burns et al., "Prevention of tissue Injury and postsurgical adhesions by precoating tissues with hyaluronic acid solutions", J. Surg. Res., 59:644-652 (1995).

Butterworth et al., "A modification of the Ellman procedure for the estimation of protein sulfhydryl groups", *Arch Biochem. Biophys.*, 118:716-723 (1967).

Campoccia et al., "Quantitative assessment of the tissue response to films of hyaluronan derivatives", *Biomaterials*, 17:963-975 (1996).

Campoccia et al., "Semisynthetic resorbable materials from hyaluronan esterification", *Biomaterials*, 19:2101-2127 (1998).

Capozzi and Modena, "Oxidation of thiol. In: The Chemistry of the Thiol Group Part II", Patai, S., editor. New York: Wiley, p. 785-839 (1974).

Casabona et al., "Prefabricated engineered bone flaps: an experimental model of tissue reconstruction in plastic surgery", *Plastic Reconstr. Surg.*, 101:577-581 (1998).

Chen and Abatangelo, "Functions of hyaluronan in wound repair", *Wound Repair Regen.*, 7:79-89 (1999).

Chen et al., "Photoimmobilization of sulfated hyaluronic acid for antithrombogenicity", *Bioconjugate Chem.*, 8:730-734 (1997).

Cheung et al., "Receptor for hyaluronan-mediated motility (RHAMM), a hyaladherin that regulates cell responses to growth factors", *Biochem. Soc. Trans.*, 27:135-42 (1999).

Choi et al., "Detection of transforming growth factor-a in the serum of gastric carcinoma patients", On*cology*, 57:236-41 (1999).

Choi et al., Studies on gelatin-containing artificial skin, II. Preparation and characterization of cross-linked gelatin-hyaluronate sponge. *J. Biomed. Mater. Res.* 48:631-39 (1999).

Coelho et al., "Properties of protein polymers as substratum for cell growth in vitro", *J. Cell Physiol.*, 83:379-388 (1974).

Collis et al., "Rapid hyaluronan uptake is associated with enhanced motility: implications for an intracellular mode of action", *FEBS Lett.*, 440:444-449 1998.

Cooper et at., "The effect of an arginine-glycine-aspartic acid peptide and hyaluronate synthetic matrix on epithelialization of meshed skin graft interstices", *J. Burn Care Rehabil.*, 17:108-16 (1996).

The European Search Report for EP application No. 03799796.2 dated Jun. 16, 2008, 9 pages (2008).

Cram et al., "Human skin storage techniques: A study utilizing a nude mouse recipient", *J. Trauma*, 23:924-29 (1983).

Cruise et al. "A sensitivity study of the key parameters in the interfacial photopolymerization of poly(ethylene glycol) diacrylate upon porcine islets", *Biotechnol. Bioeng.*, 57:655-65 (1998).

Davidson et al., "Hyaluronate derivatives and their application to wound healing: preliminary observations", *Clin. Mater.*, 8:171-77 (1991).

Day and Prestwich, "Hyaluronan-binding proteins: Tying up the giant", J. Biol. Chem., 277:4585-88 (2002).

Day and Sheehan, "Hyaluronan: polysaccharide chaos to protein organization", *Curr Opin. Stud. Biol.*, 11:617-22 (2001).

De Laco et al., "A novel hyaluronan-based gel in laparoscopic adhesion prevention: preclinical evaluation in an animal model", *Fertil. Steril.*, 69:318-23 (1998).

De Laco. P., "Adhesion in prevention in gynecological surgery: preclinical and clinical studies. In: New Frontiers in Medical Sciences: Redefining Hyaluronan", Abbazia dl Praglia, Padua, Italy, p. 345-349 (1999).

Dizerega and Campcau, "Peritoneal repair and post-surgical adhesion formation", *Hum. Reprod. Update*, 7:547-55 (2001).

Dowthwaite et al., "An essential role for the interaction between hyaluronan and hyaluronan binding proteins during Joint development", *J. Histochem. Cytochem.*, 46:641-51 (1998).

Dyson et al., "Effects of buried charged groups on cysteine thiol ionization and reactivity in *Escherichia coil* thioredoxin: structural and functional characterization of mutants of Asp 25 and Lys 57", *Biochemistry*, 36:2622-2636 (1997).

Elbert and Hubbell, "Conjugate addition reactions combined with free-radical crosslinking for the design of materials for tissue engineering", *Biomacromolecules*, 2:430-41 (2001).

Elisseeff et al., "Photoencapsulation of chondrocytes in poly(ethylene oxide) based semi-interpenetrating networks", *J. Biomed. Mater. Res.*, 51:164-71 (2000).

Elisseeff et al., "Transdermal photopolymerization for minimally invasive implantation", *Proc. Natl. Acad. Sci. USA*, 96:3104-07 (1999).

Ellman, G. L., "A colorimetric method for determining low concentrations of mercaptans", *Arch. Biochem. Biophys.*, 74:443-50 (1958).

Entwistle et al., "HA Receptors: regulators of signaling to the cytoskeleton", *J. Cell Biochem.*, 61:569-77 (1996).

Feinberg and Beebe, "Hyaluronate in vasculogenesis", *Science*, 220:1177-79 (1989).

Foschi et al., "Hyaluronic acid prevents oxygen free-radical damage to granulation tissue: a study in rats", *Int. J. Tiss. React.*, XII:333-39 (1990).

Fraser et al., "Hyaluronan: its nature, distribution, functions and turnover", *J. Intern. Med.*, 242(1 ):27-33 (1997).

Fratianne et al., "Keratinocyte allografts accelerate healing of split-thickness donor sites: Applications for improved treatment of burns", *J. Burn Care & Rehabil.*, 14:146-54 (1993).

Friedman et al., "Relative nucleophilic reactivities of amino groups and mercaptide ions in addition reactions with unsaturated compounds", *J. Am. Chem. Soc.*, 87:3672-82 (1965).
Gerdin and Hallgren, "Dynamic role of hyaluronan (HYA) in connective tissue activation and inflammation", *J. Intern. Med.*, 242:49-55 (1997).
Ghofrani et al., "The influence of systemic growth hormone administration on the healing time of skin graft donor sites in a pig model", *Plast. Reconstr. Surg.*, 104:470-5 (1988).
Gibran et al., "Basic fibroblast growth in the early human burn wound" *J. Surg. Res.*, 56:226-32 (1994).
Gilpin et al., "Recombinant human growth hormone accelerates wound healing in children with large cutaneous burns", *Ann. Surg*, 220:19-24 (1994).
Glass et al., "Characterization of a hyaluronic acid-Arg-Gly-Asp peptide cell attachment matrix", *Biomaterials*, 17:1101-08 (1996).
Goretsky et al., "Expression of interleukin-la, inteleukin-6, and basic fibroblast growth factor by cultured skin substitutes before and after grafting to full-thickness wounds in athymic mice", *J. Trauma: Injury, Infec. Crit. Care*, 40:894-900 (1996).
Gospodarowicz et al., "Fibroblast growth factor: Structure and biologic properties", *J. Cell Physiol.*, 5:15. (1987).
Gowland et al., "Marked enhanced efficacy of cyclosporin when combined with hyaluronic acid. Evidence from two T cell-mediated models", *Clin. Drug Invest.*, 11:245-50 (1996).
Graham, N. B. (1998) Hydrogels: their future, Part II. Med. Device Technol. 9:22-25 (1998).
Graham, N.B., "Hydrogels: their future, Part I", *Med. Device Technol.*, 9:18-22. (1998).
Greenhaigh et al., "PDGF and FGF stimulate wound healing in the genetically diabetic mouse", *Am. J. Pathol.*, 136:1235-46 (1990).
Hallen et al., "The potential use of hyaluronan-based compounds in laryngeal augmentative surgery", *Elsevier Science B. V.*, 353-359 (2000).
Hanthamrongwit et al., "Chondroitin-6-sulphate incorporated into collagen gels for the growth of human keratinocytes: the effect of cross-linking agents and diamines", *Biomaterials*, 17:775-80 (1996).
Hardwick et al., "Molecular cloning of a novel hyaluronic receptor that mediates tumor cell motility", *J. Cell Biol.*, 117:1343-50 (1992).
Harris et al., "Use of hyaluronic acid and cultured autologous keratinocytes and fibroblasts in extensive burns", *The Lancet*, 353:35-36 (1999).
Hascall and Laurent, "Hyaluronan: structure and physical properties". In Science of Hyaluronan Today; V. C. Mescall and M. Yanagishita, Ed.; Selkagaku Corporation: Tokyo (1997).
Hebda et al., "Basic fibroblast growth factor stimulation of epidermal wound healing in pigs", *J. Invest. Dermatol.*, 95:626-31 (1990).
Hennink and van Nostrum, "Novel crosslinking methods to design hydrogels", *Adv. Drug Del, Rev.*, 54:13-36 (2002).
Hoekstra, D., "Hyaluronan-modified surfaces for medical devices", *Medical Device Diag. Ind.*, p. 48-58 (1999).
Hong et al., "Study on gelatin-containing artificial skin IV: a comparative study on the effect of antibiotic and EGF on cell proliferation during epidermal healing", *Biomaterials*, 22:2777-83 (2001).
Hooker et al., "Prevention of adhesion formation with the use of sodium hyaluronate-based bioresorbable membrane in a rat model of ventral hernia repair with polypropylene mesh-A randomized, controlled study", *Surgery*, 125:211-16 (1999).
Hu et al., "Improvement of schwann cell attachment and proliferation on modified hyaluronic acid strands by polylysine", *Tissue Engineering*, 6(6):585-93 (2000).
Hu et al., "Polypeptide resurfacing method improves fibroblast's adhesion to hyaluronan strands", *J. Biomed. Mater. Res.*, 47:79-84 (1999).
Huang-Lee et al., "Effects of hyaluronan on collagen fibrillar matrix contraction by fibroblasts", *J. Biomed. Mater. Res*, 28:123-32 (1994).
Hubbell, J. A., "Biomaterials in Tissue Engineering", *Biotechnology*, 13:565-76 (1995).
Hubbell, J.A., "Bioactive Biomaterials", *Curr, Opin. Biotechnol.*, 10:123-129 (1999).
Iio et al., "Cell growth on poly(vinyl alcohol) hydrogel membranes containing. biguanido groups", *J. Biomed. Mater. Res.*, 28:459-62 (1994).

Illum et al., "Hyaluronic acid ester microspheres as a nasal delivery system for insulin", *J. Controlled Rel.*, 29:133-41 (1994).
Jackson et al., "Paclitaxel-loaded crosslinked hyaluronic acid films for the prevention of postsurgical adhesion", *Pharm. Res.*, 19(4):411-17 (2002).
Jeong et al., "Thermoreversible gelatin of PEG-PLEA-PEG triblock copolymer aqueous solutions", *Macromol.*, 32:7064-69 (1999).
Jiang and Zhu, "Polyanion/gelatin complexes as pH-sensitive gels for controlled protein release", *J. Appl. Polym. Sol.*, 80:1416-25 (2001).
Johns et al., "Reduction of adhesion formation by postoperative administration of ionically crass-linked hyaluronic acid", *Fertil. Steril.*, 68:37-42 (1997).
Johns et al., "Reduction of postsurgical adhesions with Intergel® adhesion prevention solution: a multicenter study of safety and efficacy after conservative gynecologic surgery", *Fertil. Steril.*, 76:595-604 (2001).
Jones and Senft, "An improved method to determine cell viability by simultaneous staining with fluorescein diacetate-propidium iodide", *Histochem. Cytochem.*, 33:77-79 (1985).
Juhlin, L., "Hyaluronan in skin", *J. Intern. Med.*, 242:61-66 (1997).
Kenchington, A. W., "Chemical modification of the side chains of gelatin" *Biochem. J.*, 68:458-68 (1958).
King and Patrick, "Development and in vitro characterization of vascular endothelial growth factor (VEGF)-loaded poly(DL-lactic-co-glycolic acid)/poly(ethylene glycol) microspheres using a solid encapsulation/single emulsion/solvent extraction technique", *J. Biomed. Mater. Res.*, 51:383-90 (2000).
Kirker et al., "Glycosaminoglycan hydrogel films as bio-interactive dressings for wound healing", *Biomaterials*, 23(17):3661-71 (2002).
Kirker et al., "Glycosaminoglycan hydrogel films as supplemental wound dressing material for donor sites", *J. Burn Care Rehab.*, 25(3):276-286 (2002).
Knudson and Knudson, "Cartilage proteoglycans", *Semin. Cell Dev. Biol.*, 12(2):6978 (2001).
Kortemme and Creighton, "Ionization of cysteine residues at the termini of model a-helical peptides. Relevance to unusual thiol pKa values in proteins of the thioredoxin family", J. Mol., Biol. 253:799-812 (1995).
Koyano et al., "Attachment and growth of cultured fibroblast cells on PVA/chitosan-blended hydrogel", *J. Biomed. Mater. Res.*, 39:486-90 (1998).
Krejci et al., "In vitro reconstitution of skin: Fibroblasts facilitate keratinocyte growth and differentiation on a cellular reticular dermis", *J. Invest. Dermatol.*, 97:843-49 (1991).
Krueger and Shelby, "Biology of human skin transplanted to the nude mouse. 1. Response to agents which modify epidermal proliferation", *J. Invest. Derm.*, 76:506-11 (1981).
Krueger et al., "Involved and uninvolved skin from psonatic subjects: are they equally diseased? Assessment by skin transplanted to congenitally athymic (nude) mice", *J. Clin. Invest.*, 68:1548-57 (1981).
Kuhl and Griffith-Cima, "Tethered epidermal growth factor as a paradigm for growth factor-induced stimulation from the solid phase", *Nature Med.*, 2:1022-27 (1996).
Kuo et al., "Chemical modification of hyaluronic acid by carbodiimides", *Bioconjugate Chem.*, 2:23241 (1991).
Langer, R., "Biomaterial in drug delivery and tissue engineering: one laboratory's experience", Acc. Chem. Res. 33:94-101 (2000).
Larsen and Balazs, "Drug delivery systems using hyaluronan and its derivatives", *Adv. Drug Deily. Rev.*, 7:279-93 (1991).
Larsen et al., "Hylan gel biomaterial: dermal and Immunologic compatibility" *J. Biomed. Mater. Res.*, 27:1129-34 (1993).
Laurent et al., "Functions of hyaluronan", *Ann. Rheum. Dis.*, 54:429-32 (1995).
Leach et al. "Reduction of postsurgical adhesion formation in the rabbit uterine horn model with use of hyaluronate/carboxymethylcellulose gel", *Fertility and Sterility*, 69:415-18 (1998).
Lee and Mooney, "Hydrogels for tissue engineering", Chem. Rev. 101:1869-79 (2001).
Lee et al., "Biomedical applications of collagen", *Int. J. Pharm.*, 221:1-22 (2001).
Lee et al., "Controlled growth factor release from synthetic extracellular matrices", *Nature*, 408:998-1000 (2000).

Lesley et al., "CD44 in inflammation and metastasis", *Glycoconjugate J.*, 14:611-22 (1997).

Lin et al., "Ligament tissue engineering using synthetic biodegradable fiber scaffolds", *Tissue Engineering*, 5:443-51 (1999).

Lundorff et al., "Reduction of post-surgical adhesions with ferric hyaluronate gel: a European study", *Human Reprod.*, 16:1982-1988 (2001).

Luo and Prestwich, "Synthesis and selective cytotoxicity of a hyaluronic acid-antitumor bioconjugate", *Bioconjucate Chem.*, 10:755.63 (1999).

Luo et al., "Cross-linked hyaluronic acid hydrogel films: new biomaterials for drug delivery.", *J. Control. Release*, 69(1):169.84 (2000).

Luo et al., "Hyaluronic acid-N-hydnoxysuccinimide: a useful Intermediate for bioconjugation", *Bioconjugate Chem.*, 12:1085-88 (2001).

Lutolf et al., "Systematic modulation of Michael-type reactivity of thiols through the use of charged amino acids", *Bioconjugate Chem.*, 12:1051-56 (2001).

Macky et al., "Synthesis, pharmacokinetics, efficacy and MT rential toxicity of a novel mitomycin C-triamcinolone acetineide conjugate", *J. Med..Chem.*, 45:122-27 (2002).

Mann et al., "Smooth muscle cell growth in photopolymerized hydrogels with cell adhesive and proteolytically degradable domains: synthetic ECM analogs for tissue engineering", *Biomateriais*, 21:3045-51 (2001).

Manuskiatti and Malnach, "Hyaluronic acid and skin: wound healing and aging", *Int. J. Dermatology*, 35:539-44 (1996).

Merrell et al., "An in vivo test of viability for cryopreserved human skin", *Curr. Sum.*, 43:296 (1986).

Mignatti et al. "Role of degradative enzymes in wound healing. In: The molecular and cellular biology of wound healing", R. A. F. Clark and P. M. Henson, Ed., Plenum Press: New York (1988).

Miller et al., "Efficacy of hyaluronic acid/nonsteroidal anti-inflammatory drug systems in preventing postsurgical tendon adhesions", *J. Biomed. Mater. Res. (Apel. Biomater.)*, 38:25-33 (1997).

Moore and Willoughby, "Hyaluronan as a drug delivery system for diclofenac: a hypothesis for mode of action", *Int. J. Tissue React.*, 17:153-56 (1995).

Morimoto et al., "Effects of viscous hyaluronate-sodium solutions on the nasal absorption of vasopressin and an analogue", *Pharm. Res.*, 8:471-74 (1991).

Moriyama et al., "Hyaluronic acid grafted with poly(ethylene glycol) as a novel peptide formulation", *J. Control. Release*, 59:77-86 (1999).

Murashita et al., Acceleration of granulation tissue ingrowth by hyaluyronic acid in artificial skin, *Brit. J. Mast Surg.*, 49:58-63 (1996).

Mustoe et al., "Growth factor-induced acceleration of tissue repair through direct and Inductive activities in a rabbit dermal ulcer model", *J. Clin. Invest.*, 87:694-701 (1991).

Nanney, L., "Epidermal and dermal effects of epidermal growth factor during wound repair", *J. Invest. Dermatol.* 94:624-29 (1990).

Neely et al., "Gleatinase activities in wounds of healing-impaired mice versus wounds of non-healing-Impaired mice", *J. Burn Care Rehabil.*, 21:395-402 (2000).

Nicolas and Gagnieu, Denatured thiolated collagen 11. Crosslinking by oxidation. *Biomaterials*, 18:815-21 (1997).

Nicolas and Gagnieu, "Denatured thiolated collagen I. Synthesis and characterization", *Biomaterials*, 18:807-13 (1997).

Nightlinger et al., In: Proc. Intern. Symp. Control. Rel. Bioact. Mater.; Controlled Release Society Inc., Deerfield, USA: Seattle, Washington, USA, p. 738-739 (1995).

Ohya at al., "Thermoresponsive artificial extracellular matrix for tissue engineering: hyaluronic acid bioconjugated with poly(N-isopropylacrylamide) grafts", *Biomacromolecules*, 2(3):856-63 (2001).

Osada et al., "The effect of cross-linked hyaluronate hydrogel on the reduction of post-surgical adhesion reformation in rabbits", *J. Int. Med. Res.*, 27:233-41 (1999).

Osada et at., "The effect of hyaluronic acid-carboxymethycelluslose in reducing adhesion reformation in rabbits", *J. Int. Med. Res.*, 27:292-96 (1999).

Otulakowski et al., "Use of a human skin-grafted nude mouse model for-the evaluation of topical retinoic acid treatment", *J. Invest. Dermatol.*, 102:515-18 (1994).

Panchagnula et at., "Animal models for transdermal drug delivery", *Methods. Fin. Exp. Clin. Pharm.*, 19:335 (1997).

Park et al., "Effects of protein charge heterogeneity in protein-polyelectrolyte complexation", *Macromolecules*, 25:290-95 (1992).

Peattie et al. (2002) Stimulation of in vivo angiogenesis by cytokine-loaded hyaluronic acid hydrogel implants and potential gene expression mechanisms for new vessel growth. Biomed. Eng. Soc.. Houston, TX, (Oct. 2002).

Peppas and Bures, "Hydrogels in pharmaceutical formulation", *Eur. Pharm. Biopharm.*, 50:27-46 (2000).

Piacquadio et al., "Evaluation of hylan b gel as a soft-tissue augmentation implant material", *J. Am. Acad. Dermatol.*, 36:544-49 (1997).

Pouyani and Prestwich, "Functionalized derivatives of hyaluronic acid ollgosaccharides: drug carriers and novel biomaterials", *Bioconjugate Chem.*, 5:339-47 (1994).

Pouyani et al., "Novel hydrogels of hyaluronic acid: Synthesis, surface morphology, and solid-state NMR", *J. Am. Chem. Soc.*, 116:7515-22 (1994).

Prestwich and Vercruysse, "Therapeutic applications of hyaluronic acid and hyaluronan derivatives", *Pharm. Sol. Technol. Today*, 1:42-43 (1998).

Prestwich et al., "Controlled chemical modification of hyaluronic acid: synthesis, applications, and biodegradation of hydrazide derivatives", *J. Control. Release*, 53:93-103 (1998).

Prestwich et al., *Chemical modification of hyaluronic acid for drug delivery, biomaterials, and biochemical probes. In: The Chemistry, Biology, and Medical Applications of Hvaluronan and its Derivatives*. T. C. Laurent, Ed.: Portland Press: London, p. 43-65 (1998).

Prestwich et al., Chemicaly-modified hyaluronan: new biomaterials and probes for cell biology. In: Abatangelo G, editor. New Frontiers in Medical Sciences: Redefining Hyaluronan. Portland Press: London, p. 181-194 (2000).

Prestwich, G. D., Biomaterials from Chemically-Modified Hyaluronan. Glycoforum http://glycoforum.gr.jpfscience/hyaluronan/HA113/1-1A18E.html (2001).

Prevo et al., "Mouse LYVE-1 is an endocytic receptor for hyaluronan in lymphatic endothelium", *J. Biol. Chem.*, 276:19420-19430 (2001).

Puchelic and Peault, "Human airway xenograft models of epithelial cell regeneration", *Respir. Res.*, 1:125-28 (2000).

Ramamurthi and Vesely, "Smooth muscle cell adhesion on crosslinked hyaluronan gels", *J. Biomed. Mater. Res.*, 60:196-205 (2002).

Richardson et al., Novel vaginal delivery systems for calcitonin. 1. Evaluation of HYAFF calcitonin microspheres in rats. *Int. J. Pharm.*, 115:9-15 (1995).

Roberts and Spom, Transforming Growth Factor-beta. In The Molecular and Cellular Biology of Wound Repair. 2nd ed., R. Clark, Ed., Plenum Press: New York, Ch. 8, p. 275-308 (1996).

Robson et al. "The safety and efficacy of topically applied recombinant basic fibroblast growth factor on the healing of chronic sores", *Ann. Surg.*, 216:401-08 (1992).

Rodgers et al. "Effect of oxiplex films (PEO/CMC) on adhesion formation and reformation in rabbit models and on periotoncal infection in a rat model", *Fertil. Steril.*, 73:831-8 (2000).

Rodgers et al., "Reduction of adhesion formation with hyaluronic acid after peritoneal surgery in rabbits", *Fertil. Steril.*, 67:553-58 (1997).

Ronchetti et al., "Structural parameters of the human knee synovial membrane in osteoarthritis before and after hyaluronan treatment", *Elsevier Science B. V.*, 119-127 (2000).

Rosenquist et at., "Skin Preservation at 4 degrees C: a species comparison. Cryobiology" 25:31-7 (1988).

Ruiz-Cardona et al., "Application of benzyl hyaluronate membranes as potential wound dressings: evaluation of water vapour and gas permeabilities", *Biomaterials*, 17:1639-43 (1996).

Saettone et al., "Mucoadhesive ophthalmic vehicles: Evaluation of polymeric low-viscosity formulations", *J. Ocular Pharm.*, 10:83-92 (1994).

Sawada et al., "Adhesion preventative effect of hyaluronic acid after intraperitoneal surgery in mice", *European Soc. Hum. Reprod. Embryol.*, 14:1470-72 (1999).

Scott and Pappas, "Compositional effects on network structure of highly crosslinked copolymers of PEG-containing -multiacrylates with acrylic acid", *Macromolecules*, 32:6139-48 (1999).

Seckel et al., "Hyaluronic acid through a new injectable nerve guide delivery system enhances peripheral nerve regeneration in the rat", *J. Neurosci. Res.*, 40:318-24 (1995).

Short et al., "Percutaneous absorption of biologically active interferon-gamma in a human skin graft-nude mouse model", *Pharm. Res.*, 13:1020-27 (1996).

Shu et al., "Disulfide-crosslinked hyaluronan-gelatin hydrogel films: a covalent mimic of the extracellular matrix for in vitro cell growth", *Biomaterials*, 24:3825-34 (2003).

Shu et al., "Novel pH-sensitive citrate crosslinked chitosan film for drug controlled release", *Int. J. Pharm.*, 212:19-28 (2001).

Shu et al., "In situ crosslinkable hyaluronan hydrogels for tissue engineering", *Biomaterials*, 25:1339-48 (2004).

Smeds et al., "Synthesis of a novel polysaccharide hydrogel" *Pure Appl. Chem. A*. 36:981-89 (1999).

Smith et al., "Efficacy of growth factors in the accelerated closure of interstices in explanted meshed human skin grafts", *J. Burn Care Rehab.*, 21:5-9 (2000).

Sorrell et al., "Versican in human fetal skin development", *Anat. Embryol. P.*, 45-56 (1999).

Sullivan and Klagsburn, "Purification and assay of intact human basic fibroblast growth factor using heparin-sepharose chromatography", *J. Tiss. Culture Meth.*, 10:125-32 (1986).

Sutherland, I. W., "Novel established applications of microbial polysaccharides", *Trends Biotechnol.*, 16:41-6 (1998).

Swift et al., "Age-related alerations in the inflammatory response to dermal injury", *J. Invest. Derm.*, 117:1027-35 (2001).

Swift et at., "Impaired wound repair and delayed angiogenesis in aged mice", *Lab. Invest.*, 79:1479-1487 (1999).

Tabata and Ikeda, "Protein release from gelatin matrices", *Adv. Drug Del. Rev.*, 31:287-301 (1998).

Tammi et al., "Hyaluronan enters keratinocytes by a novel endocytic route catabolism", *J. Biol. Chem..* 276:35111-22 (2001).

Thannhauser et al., "Analysis for disulfide bonds in peptides and proteins", *Methods Enzymol.*, 143:115-19 (1987).

The Gordon Research Conference in Signal Transduction By Engineered Extracellular Matrices; Jun. 23-27, 2002 at Connecticut College in New London, Connecticut pp. 1-4 (2002).

Tomihata and Ikeda, "Cross-linking of hyaluronic acid with glutaraldehyde", *J. Polym. Sci. A: Polym. Chem.*, 35:3553-59 (1997).

Tomihata and Ikeda, "Crosslinking of hyaluronic acid with water-soluble carbodimide", *J Biomed. Mater. Res.*, 37:243-51 (1997).

Tompkins et al., "Increased survival after massive thermal injuries in adults: preliminary report using artificial skin", *Crit. Care Med.*, 17:734-40 (1989).

Tompkins et al., "Prompt escchar excision: a treatment system contributing to reduce burn mortality", *Ann. Surg.*, 204:272-81 (1986).

Tompkins et at., "Significant reductions in mortality for children with burn injuries through the use of prompt eschar excision", *Ann. Surg.*, 208:577-85 (1988).

Toole, B. P. "Hyaluronan in morphogenesis", *Semin. Cell Dev. Biol.*, 12:79-87 (2001).

Toole, B. P., "Hyaluronan in morphogenesis", *J. Intern. Med.*, 242:35-40 (1997).

Turley, E. A., "The role of a cell-associated hyaluronan binding protein in fibroblast behavior" In: *The Biology of Hvaluronan*. C. Foundation, Ed.; J. Wiley & Sons, Ltd.: Chichester, UK, p. 121-37 (1989).

Vercruysse and Prestvvich, "Hyaluronate derivatives in drug delivery" *Crit. Rev. Ther. Drug Carrier Syst.*, 15(5):513-55 1998.

Vercruysse et al., "Synthesis and in vitro degradation of new polyvalent hydrazide cross-linked hydrogels of hyaluronic acid", *Bioconjugate Chem.*, 8:686-94 (1997).

Verso et at., "Development of a novel glucose polymer solution (Icodextrin) for adhesion prevention: pre-clinical studies", *Hum. Reprod.*, 15:1764-72 (2000).

Vlodaysky, L., "Extracellular sequestration and release of fibroblast growth factor a regulatory mechanism?", *Trends Biochem. Sci.*, 16:268-71 (1991).

Werner et at., "Induction of keratinocyte growth factor expression is reduced and delayed during wound healing in the genetically diabetic mouse", *J. Invest. Dermatol.*, 103:469-75 (1994).

West and Hubbell, "Comparison of covalently and physically cross-linked polyethylene glycol-based hydrogels for the prevention of postoperative adhesions in a rat model", *Biomaterials*, 16:1153-6 (1995).

West et al., "Angiogenesis induced by degradation products of hyaluronic acid", *Science*, 228:1324-26 (1991).

White et al., "Live confocal microscopy of oligonecleotide uptake by keratinicytes in human skin grafts on nude mice", *J. Invest. Dermatol.*, p. 112 (1999).

Wiig et al., "Effects of hyaluronan on cell proliferation and collagen synthesis: a study of rabbit flexor tendons in vitro", *J. Hand Surg.*, p. 21A:599-604 (1996).

Willen et at., "Patterns of glycosaminoglycan/proteoglycan immunostaining in human skin during aging", *J. Invest. Dermatol.*, 96:968-74 (1991).

Working et al., "Safety of poly(ethylene glycol) and poly(ethylene glycol) derivatives", In: *Poly(ethylene glycol): Chemistry and Biological Applications*. J. M. Harris and S. Zalipsky, Ed.; American Chemical Society : Washington, D.C., pp. 45-57 (1997).

Yaacobi et al., "Prevention of postoperative abdominal adhesions by tissue precoating with polymer solutions", *J. Surgical. Res.*, 55:422-26 (1993).

Yamauchi et al., "Films of collagen crosslinked by S-S bonds: preparation and characterization", *Biomaterials*, 22:855-63 (2001).

Yates et al., "Epidermal growth factor and related growth factors", *Int, J. Dermatol.*, 30:687-94 (1991).

Yoldemir et at., "Comparison of the reduction of postoperative adhesions by two barriers, one solution, and two phamtacologic agents in the rat uterine model", *Fertility and Sterility*, 78(2):335-39 (2002).

Yu and Grainger (1994) Amphiphilic thermosensitive n-isopropylacrylamide terpolymer hydrogels prepared by micellar polymerization in aqueous media. Macromolecules 27:4554-60.

Yui et al., "Inflammation Responsive Degradation of Crosslinked Hyaluronic Acid Gels", *J. Control. Release*, 22:105-16 (1992).

Yui et al., "Photo-Responsive degradation of heterogeneous hydrogels comprising crosslinked hyaluronic acid and lipid microspheres for temporal drug delivery", *J. Control. Release*, 26:141-45 (1993).

Yui et al., "Regulated release of drug microspheres from inflammation responsive degradable matrices of crosslinked hyaluronic acid", *J. Control. Release*, 25:133-43 (1993).

Zhao, "Hydrazide-containing inhibitors of HIV-1 integrase", *J. Med. Chem.*, 40:937-941 (1997).

Zhong et al., "Biodegradation of hyaluronic acid derivatives by hyaluronidase", *Biomaterials*, 15:359-65 (1994).

Zhou et al., "Purification and subunit characterization of the rat liver endocytic hyaluronan receptor", *J. Biol. Chem.*, 274:33831-34 (1999).

Zhu et al., "Stabilization of proteins encapsulated in injectable poly(lactide-co-glycolide)", *Nature Biotech.*, 18:52-7 (2000).

Zimmermann et al., "Novel hydrogel as supports for in vitro cell growth: poly(ethylene glycol)- and gelatine-based (meth)acrylamidopeptide macromonomers", *Biomaterials*, 23:2127-34 (2002).

Chamow, et al., "Conjugation of soluble CD4 without loss of biological activity via a novel carbohydrate-directed cross-linking reagent", J. Biol. Chem., vol. 267, No. 22, pp. 15916-15922 (1992).

Keller, et al., "Preparation and some properties of maleimido acids and maleoyl derivatives of peptides", Helv. Chimica Acta, vol. 58, No. 2, pp. 62-63 (1975).

Roy, et al., "Dendritic 3'-sulfo-lewis$^x$-(Glc) as potent L- and E-selectin antogonists", Carbohydrate Letters, vol. 2, pp. 259-266, (1997).

Shafer, et al., "Activation of soluble polysaccharides with 1-cyano-4-dimethylaminopyridinium tetrafluoroborate (CDAP) for use in protein-polysaccharide conjugate vaccines and immunological reagents. II. Selective crosslinking of proteins to CDAP-activated polysaccharides", Vaccine, vol. 18, p. 1273-1281 (2000).

Shu, et al., "Disulfide cross-linked hyaluronan hydrogels", Biomacromolecules, vol. 3, pp. 1304-1311 (2002).

Suli-Varga, et al., "b-Chloroethylcarbamoyl derivatives of enkaphalin analogs", Acta Chimica Hungarica, vol. 120, No. 1, pp. 23-28 (1985).

Umemoto, et al., "Preparation and in vitro cytotoxicity of a methotrexate-anti-mm46 monoclonal antibody conjugate via an oligopeptide spacer", Int. J. Cancer, vol. 43, No. 677-684 (1989).

Zaidi, et al., "Disulfide linkage of biotin identifies a 106-kDa $Ca^{2+}$ release channel in sarcoplasmic reticulum", J. Biol. Chem., vol. 264, No. 36, pp. 21737-21747 (1989).

Zara, et al., "A Carbohydrate-directed heterobifunctional cross-linking reagent for the synthesis of immunoconjugates", Anal. Biochem., vol. 194, pp. 156-162 (1991).

\* cited by examiner

CROSSLINKED COMPOUNDS AND METHODS OF MAKING AND USING THEREOF

CROSS REFERENCE TO RELATED APPLICATIONS

This application claims the benefit of priority and is a continuation of U.S. patent application Ser. No. 12/234,445, filed Sep. 19, 2008, which is a continuation of U.S. patent application Ser. No. 10/519,173, filed Apr. 19, 2005 now abandoned, which is a U.S. national stage application filed under 35 U.S.C. §371 based upon International Patent Application No. PCT/US03/15519, filed May 15, 2003, which claims the benefit of priority of U.S. Provisional Patent Application No. 60/390,504, filed Jun. 21, 2002, which are hereby incorporated by reference herein in their entireties.

The research leading to this invention was funded in part by the National Institutes of Health, Grant No. NIH 5R01 DC04663. The U.S. Government may have certain rights on this invention.

BACKGROUND

The use of macromolecules in pharmaceutical applications has received considerable attention. At times, it is desirable to couple two or more macromolecules to produce new macromolecule scaffolds with multiple activities. Existing technologies used to couple two or macromolecules, however, present numerous difficulties. For example, the alkaline conditions or high temperatures necessary to create hydrogels with high mechanical strength are cumbersome and harsh. Although the use of crosslinkers to produce macromolecular scaffolds has met with some success, the crosslinking agents are often relatively small, cytotoxic molecules, and the resulting scaffold has to be extracted or washed extensively to remove traces of unreacted reagents and byproducts (Hennink, W. E.; van Nostrum, C. F. *Adv. Drug Del. Rev.* 2002, 54, 13-36), thus precluding use in many medical applications. A physiologically compatible macromolecular scaffold capable of being produced in a straightforward manner is heeded before they will be useful as therapeutic aids. Described herein are compounds and methods that are capable of coupling two or more molecules, such as macromolecules, under mild conditions.

SUMMARY OF EMBODIMENTS

Described herein are crosslinked compounds. Also described herein are methods of making and using crosslinked compounds.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
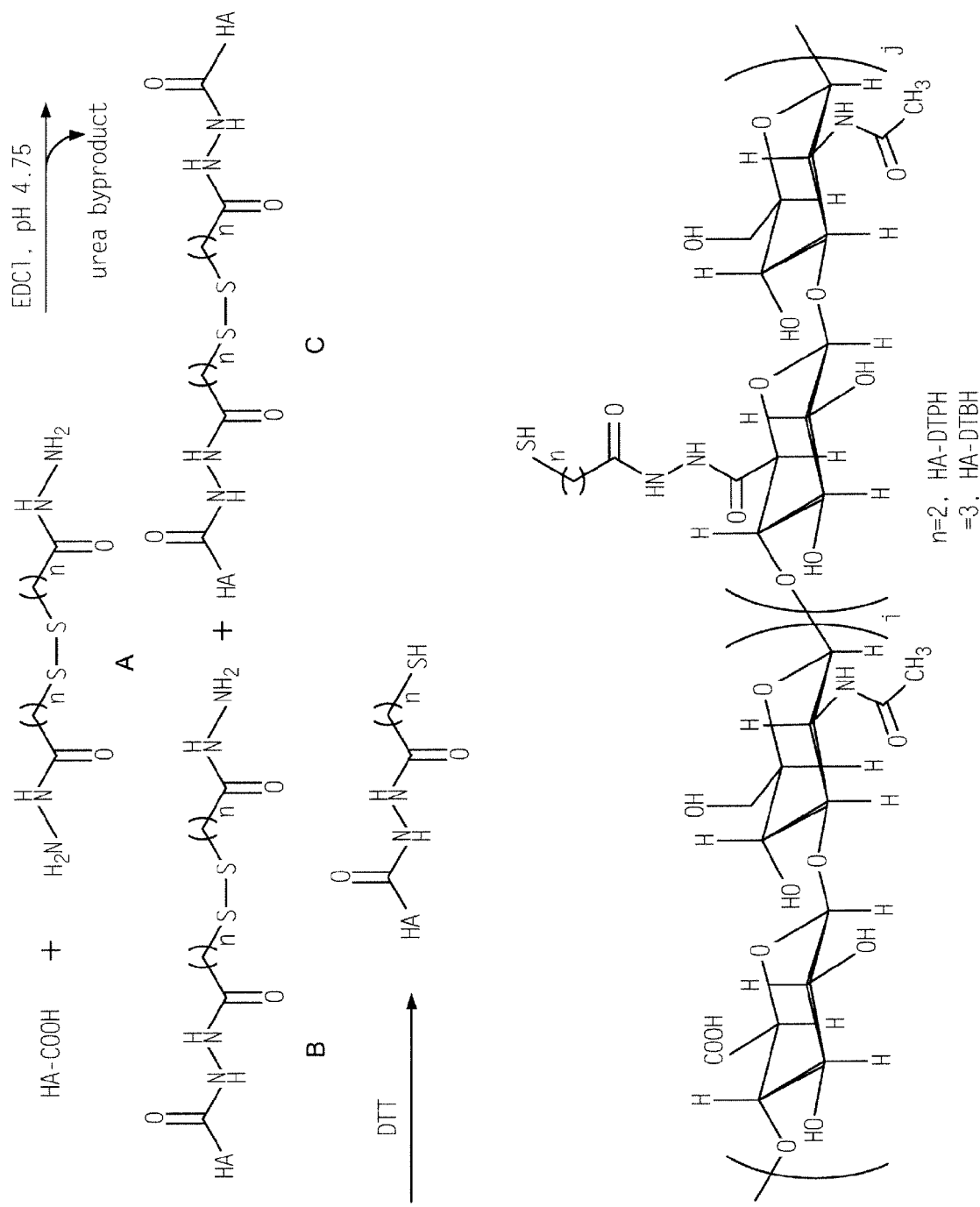
FIG. 1 shows the reaction scheme for producing HA-thiolated derivatives.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a." "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

A residue of a chemical species, as used in the specification and concluding claims, refers to the moiety that is the resulting product of the chemical species in a particular reaction scheme or subsequent formulation or, chemical product, regardless of whether the moiety is actually obtained from the chemical species. For example, a polysaccharide that contains at least one —COOH group can be represented by the formula Y—COOH, where Y is the remainder (i.e., residue) of the polysaccharide molecule.

Variables such as $R^3$-$R^5$, $R^7$, $R^8$, E, L, J, G, M, Q, U, V, X, Y, and Z used throughout the application are the same variables as previously defined unless stated to the contrary.

The term "alkyl group" as used herein is a branched or unbranched saturated hydrocarbon group of 1 to 24 carbon atoms, such as methyl, ethyl, n-propyl, isopropyl, n-butyl, isobutyl, r-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "polyalkylene group" as used herein is a group having two or more $CH_2$ groups linked to one another. The polyalkylene group can be represented by the formula —$(CH_2)_n$—, where n is an integer of from 2 to 25.

The term "polyether group" as used herein is a group having the formula —$[(CHR)_nO]_m$—, where R is hydrogen or a lower alkyl group, n is an integer of from 1 to 20, and m is an integer of from 1 to 100. Examples of polyether groups include, polyethylene oxide, polypropylene oxide, and polybutylene oxide.

The term "polythioether group" as used herein is a group having the formula —$[(CHR)_nS]_m$—, where R is hydrogen or a lower alkyl group, n is an integer of from 1 to 20, and m is an integer of from 1 to 100.

The term "polyimino group" as used herein is a group having the formula —$[(CHR)_nNR]_m$—, where each R is, independently, hydrogen or a lower alkyl group, n is an integer of from 1 to 20, and m is an integer of from 1 to 100.

The term "polyester group" as used herein is a group that is produced by the reaction between a compound having at least two carboxylic acid groups with a compound having at least two hydroxyl groups.

The term "polyamide group" as used herein is a group that is produced by the reaction between a compound having at least two carboxylic acid groups with a compound having at least two unsubstituted or monosubstituted amino groups.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

I. Crosslinking Via Oxidative Coupling

In one aspect described herein is a method for preparing a compound, wherein the method includes reacting a first thiolated compound having the formula III

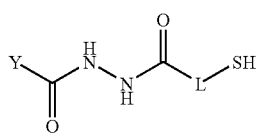

III wherein

Y is a residue of a macromolecule, and

L is a polyalkylene group, a polyether group, a polyamide group, a polyimino group, an aryl group, a polyester, or a polythioether group, with a second thiolated compound having at least one SH group in the presence of an oxidant, wherein the first thiolated compound and second thiolated compound are the same or different compounds.

FIG. 1 depicts one aspect of the method described above for producing a first thiolated compound having the formula III, where Y is hyaluronan. The first step involves reacting a macromolecule having the formula Y—COOH with the dihydrazide/disulfide compound having the formula A. The reaction is performed in the presence of a condensing agent. A condensing agent is any compound that facilitates the reaction between the dihydrazide group of compound A and the COOH group on the macromolecule. In one aspect, the condensing agent is a carbodiimide, including, but not limited to, 1-ethyl-3-[3-(dimethylamino)propyl]-carbodiimide (EDCI). As depicted in FIG. 1, a mixture of products (B and C) are produced after the first step. The disulfide bond in compounds B and C is cleaved with a reducing agent. In one aspect, the reducing agent is dithiothreitol. Cleavage of the disulfide bonds in compounds B and C produces the first thiolated compound having the formula III.

The macromolecule is any compound having at least one group that can react, with a hydrazide compound. In one aspect, the macromolecule has at least one —COOH group of the salt or ester thereof. In another aspect, the macromolecule is an oligonucleotide, a nucleic acid or a metabolically stabilized analogue thereof, a polypeptide, a lipid, a glycoprotein, or a glycolipid. In another aspect, the macromolecule is a polysaccharide, a protein, or a synthetic polymer.

In one aspect, the macromolecule can be a pharmaceutically-acceptable compound. In one aspect, the pharmaceutically-acceptable compounds can include substances capable of preventing an infection systemically in the biological system or locally at the defect site, as for example, anti-inflammatory agents such as, but not limited to pilocarpine, hydrocortisone, prednisolone, cortisone, diclofenac sodium, indomethacin, 6∝-methyl-prednisolone, corticosterone, dexamethasone, prednisone, and the like; antibacterial agents including, but not limited to, penicillin, cephalosporins, bacitracin, tetracycline, doxycycline, gentamycin, chloroquine, vidarabine, and the like; analgesic agents including, but not limited to, salicylic acid, acetaminophen, ibuprofen, naproxen, piroxicam, flurbiprofen, morphine, and the like; local anesthetics including, but not limited to, cocaine, lidocaine, benzocaine, and the like; immunogens (vaccines) for stimulating antibodies against hepatitis, influenza, measles, rubella, tetanus, polio, rabies, and the like; peptides including, but not limited to, leuprolide acetate (an LH-RH agonist), nafarelin, and the like. AH compounds are available from Sigma Chemical Co. (Milwaukee, Wis.).

In another aspect, the pharmaceutically-acceptable compound can be a substance or metabolic precursor which is capable of promoting growth and survival of cells and tissues or augmenting the functioning of cells is useful, as for example, a nerve growth promoting substance such as a ganglioside, a nerve growth factor, and the like; a hard or soft tissue growth promoting agent such as fibronectin (FN), human growth hormone (HGH), a colony stimulating factor, bone morphogenic protein, platelet-derived growth factor (PDGF), insulin-derived growth factor (IGF-I, IGF-II), transforming growth factor-alpha (TGF-alpha), transforming growth factor-beta (TGF-beta), epidermal growth factor (EGF), fibroblast growth factor (FGF), interleukin-1 (IL-1), vascular endothelial growth factor (VEGF) and keratinocyte growth factor (KGF), dried bone material, and the like; and antineoplastic agents such as methotrexate, 5-fluorouracil, adriamycin, vinblastine, cisplatin, tumor-specific antibodies conjugated to toxins, tumor necrosis factor, and the like.

In another aspect, the pharmaceutically-acceptable compound can include hormones such as progesterone, testosterone, and follicle stimulating hormone (FSH) (birth control, fertility-enhancement), insulin, and the like; antihistamines such as diphenhydramine, and the like; cardiovascular agents such as papaverine, streptokinase and the like; anti-ulcer agents such as isopropamide iodide, and the like; bronchodilators such as metaproternal sulfate, aminophylline, and the like; vasodilators such as theophylline, niacin, minoxidil, and the like; central nervous system agents such as tranquilizer, B-adrenergic blocking agent, dopamine, and the like; antipsychotic agents such as risperidone, narcotic antagonists such as naltrexone, naloxone, buprenorphine; and other like substances. All compounds are available from Sigma Chemical Co. (Milwaukee, Wis.).

Polysaccharides useful in the methods described herein have at least one group, such as a carboxylic acid group or the salt or ester thereof, that can react with a dihydrazide. In one aspect, the polysaccharide is a glycosaminoglycan (GAG). A GAG is one molecule with many alternating subunits. For example, HA is (GlcNAc-GlcUA-)x. Other GAGs are sulfated at different sugars. Generically, GAGs are represented by the formula A-B-A-B-A-B, where A is a uronic acid and B is an aminosugar that is either O—or N-sulfated, where the A and B units can be heterogeneous with respect to epimeric content or sulfation. Any natural or synthetic polymer containing uronic acid can be used. In one aspect, Y in formula III is a sulfated-GAG.

There are many different types of GAGs, having commonly understood structures, which, for example, are within the disclosed compositions, such as chondroitin sulfate, dermatan, heparan, heparin, dermatan sulfate, and heparan sulfate. Any GAG known in the art can be used in any of the methods described herein. Glycosaminoglycans can be purchased from Sigma, and many other biochemical suppliers. Alginic acid, pectin, and carboxymethylcellulose are among other carboxylic acid containing polysaccharides useful in the methods described herein.

In another aspect, the polysaccharide Y in formula III is hyaluronan (HA). HA is a non-sulfated GAG. Hyaluronan is a well known, naturally occurring, water soluble polysaccharide composed of two alternatively linked sugars, D-glucuronic acid and N-acetylglucosamine. The polymer is hydrophilic and highly viscous in aqueous solution at relatively low solute concentrations. It often occurs naturally as the sodium salt, sodium hyaluronate. Methods of preparing commercially available hyaluronan and salts thereof are well known.

Hyaluronan can be purchased from Seikugaku Company, Clear Solutions Biotech, Inc., Pharmacia Inc., Sigma Inc., and many other suppliers. For high molecular weight hyaluronan it is often in the range of 100 to 10,000 disaccharide units. In another, aspect, the lower limit of the molecular weight of the hyaluronan is from 10,000, 20,000, 30,000, 40,000, 50,000, 60,000, 70,000, 80,000, 90,000, or 100,000, and the upper limit is 200,000, 300,000, 400,000, 500,000, 600,000, 700,000, 800,000, 900,000, or 1,000,000, where any of the lower limits can be combined with any of the upper limits. In another aspect, Y in formula III is not hyaluronan.

Y in formula III can also be a synthetic polymer. The synthetic polymer has at least one carboxylic acid group or the salt or ester thereof, which is capable of reacting with a hydrazide. In one aspect, the synthetic polymer residue in formula III comprises the synthetic polymer comprises glucuronic acid, polyacrylic acid, polyaspratic acid, polytartaric acid, polyglutamic acid, or polyfumaric acid.

In another aspect, Y in formula III is a protein. Proteins useful in the methods described herein include, but are not limited to, an extracellular matrix protein, a chemically-modified extracellular matrix protein, or a partially hydrolyzed derivative of an extracellular matrix protein. The proteins may be naturally occurring or recombinant polypeptides possessing a cell interactive domain. The protein can also be mixtures of proteins, where one or more of the proteins are modified. Specific examples of proteins include, but are not limited to, collagen, elastin, decorin, laminin, or fibronectin.

The identity and length of L in formula III will vary depending upon the end use of the compound. In one aspect, L in formula III is a polyalkylene group. In another aspect, L in formula III is a $C_1$ to $C_{20}$ polyalkylene group. In another aspect, L in formula I is $CH_2CH_2$ or $CH_2CH_2CH_2$. In another aspect, Y is a residue of a polysaccharide or protein and L is $CH_2CH_2$ or $CH_2CH_2CH_2$.

The second thiolated compound is any compound having at least one thiol group. The first and second thiolated compounds can be the same or different compounds. In one aspect, the second thiolated compound can be any macromolecule described above. In one aspect, the second thiolated compound is a polysaccharide having at least one SH group. Any of the polysaccharides described above can be used as the second thiolated compound. In another aspect, the second thiolated compound comprises a sulfated-glycosaminoglycan. In a further aspect, the second thiolated compound includes chondroitin sulfate, dermatan, heparan, heparin, dermatan sulfate, heparan sulfate, alginic acid, pectin, carboxymethylcellulose, or hyaluronan having at least one SH group.

In another aspect, the second thiolated compound has the formula II

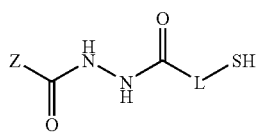

wherein
Z is a residue of a macromolecule, and
L is a polyalkylene group, a polyether group, a polyamide group, a polyimino group, an aryl group, a polyester, or a polythioether group.

The macromolecule residue Z can be any of the macromolecules described above. In one aspect, the second thiolated compound can be a protein having at least one thiol group. In one aspect, the protein comprises an extracellular matrix protein or a chemically-modified extracellular matrix protein. In another aspect, the protein comprises collagen, elastin, decorin, laminin, or fibronectin In another aspect, L in formula II is a polyalkylene group. In another aspect, L in formula II is a $C_1$ to $C_{20}$ polyalkylene group. In another aspect, L in formula II is $CH_2CH_2$ or $CH_2CH_2CH_2$. In one aspect, Z is a residue of hyaluronan and L in formula II is $CH_2CH_2$ or $CH_2CH_2CH_2$. In a further aspect, Z is a residue of gelatin and L in formula II is $CH_2CH_2$ or $CH_2CH_2CH_2$.

In another aspect, described herein is a method for making a crosslinked compound involving reacting
  (a) a first thiolated compound comprising a protein having at least one SH group; and
  (b) a second thiolated compound comprising a polysaccharide or synthetic polymer having at least one SH group,
in the presence of an oxidant.

In this aspect, the first thiolated compound has the formula III

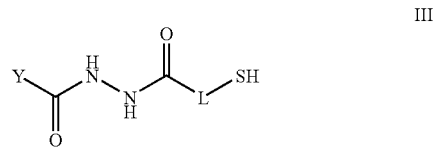

and the second thiolated compound has the formula II

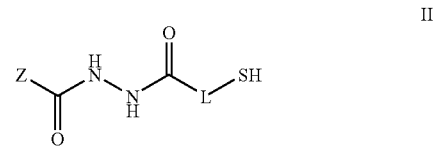

wherein
  Y is a protein residue;
  Z is a polysaccharide residue or a residue of a synthetic polymer; and
  each L is, independently, a polyalkylene group, a polyether group, a polyamide group, a polyester group, a polyimino group, an aryl group, or a polythioether group.

In one aspect, L in formula II and II is, independently, $CH_2CH_2$ or $CH_2CH_2CH_2$. In another aspect, Z is a residue of hyaluronan.

The reaction between the first and second thiolated compounds is performed in the presence of an oxidant. In one aspect, the reaction between the first and second thiolated compounds can be conducted in the presence of any gas that contains oxygen. In one aspect, the oxidant is air. This aspect also contemplates the addition of a second oxidant to expedite the reaction. In another aspect, the reaction can be performed under, an inert atmosphere (i.e., oxygen free), and an oxidant is added to the reaction. Examples of oxidants useful in this method include, but are not limited to, molecular iodine, hydrogen peroxide, alkylhydroperoxides, peroxy acids, dialkyl sulfoxides, high valent metals such as $Co^{+3}$ and $Ce^{+4}$, metal oxides of manganese, lead, and chromium, and halogen transfer agents. The oxidants disclosed in Capozzi. G.; Modena. G. In *The Chemistry of the Thiol Group Part II*; Patai, S., Ed.; Wiley: New York, 1974; pp 785-839, which is incorporated by reference in its entirety, are useful in the methods described herein.

The reaction between the first and second thiolated compounds can be conducted in a buffer solution that is slightly basic. The amount of the first thiolated compound relative the amount of the second thiolated compound can vary. In one aspect, the volume ratio of the first thiolated compound to the second thiolated compound is from 99:1, 90:10, 80:20, 70:30, 60:40, 50:50, 40:60, 30:70, 20:80, 10:90, or 1:99. In one aspect, the first and second thiolated compound react in air and are allowed to dry at room temperature. In this aspect, the dried material can be exposed to a second oxidant, such as hydrogen peroxide. The resultant compound can then be rinsed with water to remove any unreacted first and/or second thiolated compound and any unused oxidant. One advantage of preparing coupled compound via the oxidative coupling methodology described herein is that crosslinking can occur in an aqueous media under physiologically benign conditions without the necessity of additional crosslinking reagents.

The compounds produced using the methods described above have at least one fragment comprising the formula VI

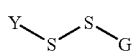

VI wherein

Y is a residue of a macromolecule, wherein Y is not a residue of hyaluronan; and G is a residue of a thiolated compound.

The term "fragment" as used herein refers to the entire molecule itself or a portion or segment of a larger molecule. For example, Y in formula VI may be high molecular weight polysaccharide that is crosslinked by disulfide linkage with another polysaccharide, synthetic polymer, or thiolated polymer to produce the coupled compound. Alternatively, the coupled compound may have multiple disulfide linkages. The compound has at a minimum one unit depicted in formula VI, which represents at least one disulfide linkage as the result of at least one first thiolated compound that reacted with at least one second thiolated compound via oxidation.

The macromolecule (Y) and thiolated compound (G) can be any of the macromolecules described above. In one aspect, Y in formula VI is a polysaccharide, a protein, or a synthetic polymer. In another aspect, the fragment comprises the formula VIII

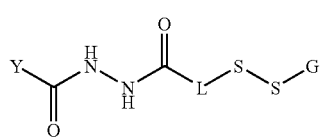

VIII wherein

Y is a residue of a macromolecule, wherein Y is not a residue of hyaluronan;

L is a polyalkylene group, a polyether group, a polyamide group, a polyimino group, an aryl group, a polyester, or a polythioether group; and G is a residue of a thiolated compound.

In one aspect, Y in formula VIII is a residue of any of the glycosaminoglycans described above including, but not limited to, chondroitin sulfate, dermatan, heparan, heparin, dermatan sulfate, heparan sulfate, alginic acid, pectin, or carboxymethylcellulose. In a further aspect, L in formula VIII is $CH_2CH_2$ or $CH_2CH_2CH_2$. In another aspect, G is a residue of any of the polysaccharides described above, including a glycosaminoglycan such as chondroitin sulfate, dermatan, heparan, heparin, dermatan sulfate, heparan sulfate, alginic acid, pectin, carboxymethylcellulose, or hyaluronan.

II. Coupling Compounds Via the Reaction Between a Thiol Compound and a Thiol-Reactive Compound In another aspect, described herein is a method for coupling two or more compounds by reacting a first thiolated macromolecule having at least one SH group with at least one compound having at one thiol-reactive electrophilic functional group. In one aspect, the compound has at least two-thiol reactive functional groups.

Any of the macromolecules described above can be used in this aspect. Two or more different macromolecules can be used in this method. For example, a second thiolated macromolecule can be used in combination with the first thiolated macromolecule. In this aspect, the first and second thiolated macromolecule can be the same or different compounds.

In one aspect, the macromolecule is a polysaccharide. In this aspect, the polysaccharide is a sulfated-glycosaminoglycan including, but not limited to, chondroitin sulfate, dermatan, heparan, heparin, dermatan sulfate, heparan sulfate, alginic acid, pectin, or carboxymethylcellulose. In another aspect, the polysaccharide is hyaluronan. In another aspect, the polysaccharide has the formula III described above. In this aspect, Y is a residue of hyaluronan and L is $CH_2CH_2$ or $CH_2CH_2CH_2$.

In another aspect, the macromolecule is a compound having the formula III, wherein Y is a protein. Any of the proteins described above can be used in this aspect. In one aspect, the protein is collagen, elastin, decorin, laminin, or fibronectin.

A compound having at least one thiol-reactive electrophilic group is also used in this aspect of the method. The term "thiol-reactive electrophilic group" as used herein is any group that is susceptible to nucleophilic attack by the lone-pair electrons on the sulfur atom of the thiol group or by the thiolate anion. Examples of thiol-reactive electrophilic groups include groups that have good leaving groups. For example, an alkyl group having a halide or alkoxy group attached to it or an α-halocarbonyl group are examples of thiol-reactive electrophilic groups. In another aspect, the thiol-reactive electrophilic group is an electron-deficient vinyl group. The term "an electron-deficient vinyl group" as used herein, is a group having a carbon-carbon double bond and an electron-withdrawing group attached to one of the carbon atoms. An electron-deficient vinyl group is depicted in the formula $C_\beta=C_\alpha X$, where X is the electron-withdrawing group. When the electron-withdrawing group is attached to $C\alpha$, the other carbon atom of the vinyl group ($C\beta$) is more susceptible to nucleophilic attack by the thiol group. This type of addition to an activated carbon-carbon double bond is referred to as a Michael addition. Examples of electron-withdrawing groups include, but are not limited to, a nitro group, a cyano group, an ester group, an aldehyde group, a keto group, a sulfone group, or an amide group. Examples of compounds possessing thiol-reactive electrophilic groups include, but are not limited to, maleimides, vinyl sulfones, acrylonitriles, α-methylene esters, quinone methides, acryloyl esters or amides, or α-halo esters or amides.

In one aspect, the thiol-reactive compound has two electron-deficient vinyl groups, wherein the two electron-deficient vinyl groups are the same. In another aspect, the thiol-reactive compound is a diacrylate, a dimethacrylate, a diacrylamide, a dimethacrylamide, or a combination thereof.

In another aspect, the thiol-reactive compound has the formula V

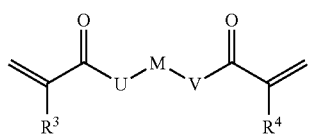

wherein
$R^3$ and $R^4$ are, independently, hydrogen or lower alkyl;
U and V are, independently, O or $NR^5$, wherein $R^5$ is, independently, hydrogen or lower alkyl; and
M is a polyalkylene group, a polyether group, a polyamide group, a polyimino group, a polyester, an aryl group, or a polythioether group.

In one aspect, $R^3$ and $R^4$ are hydrogen, U and V are oxygen, and M is a polyether group. In another aspect, $R^3$ and $R^4$ are hydrogen, U and V are NH, and M is a polyether group. In a further aspect, $R^3$ and $R^4$ are methyl, U and V are oxygen, and M is a polyether group. In another aspect, $R^3$ and $R^4$ are methyl, U and V are NH, and M is a polyether group.

Figure 22:
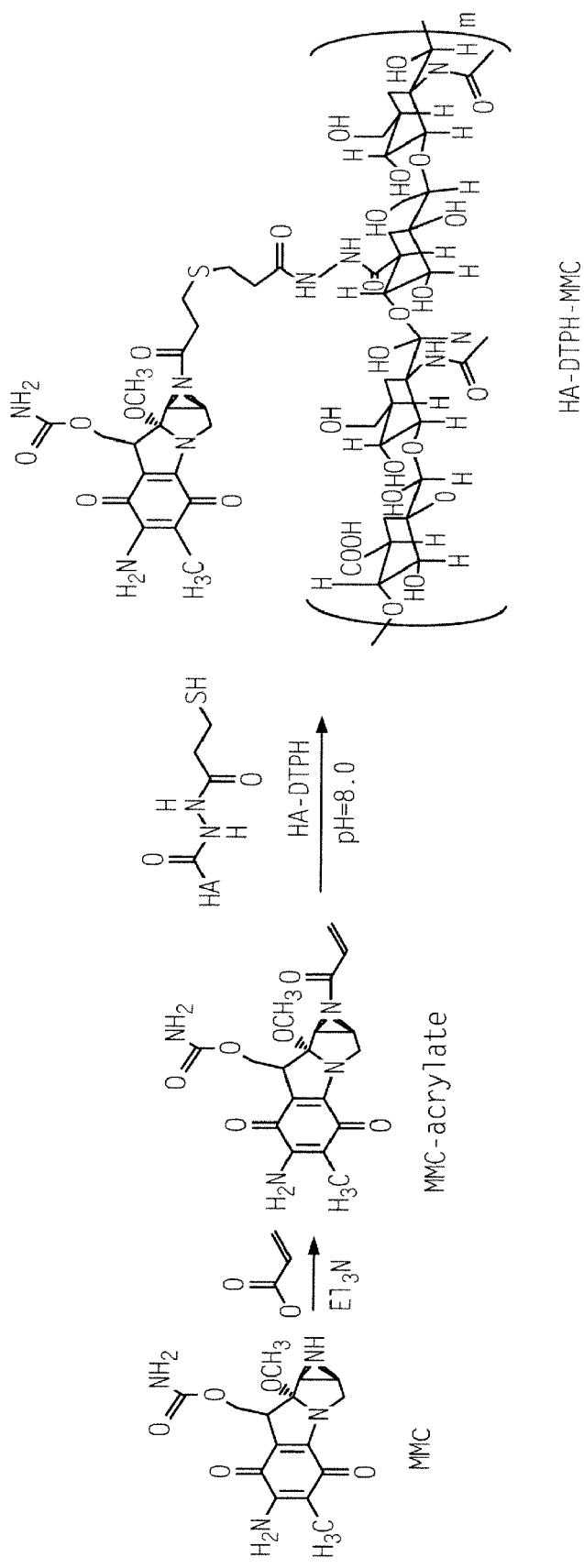
FIG. 22 shows the synthesis of HA-DTPH-MMC.
Figure 23:
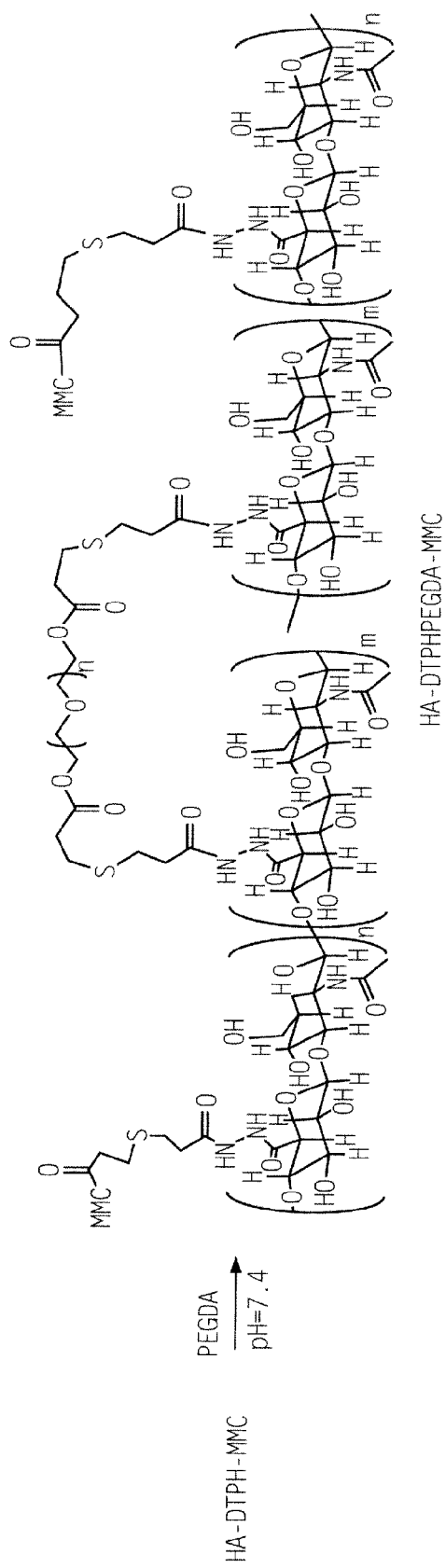
FIG. 23 shows the synthesis of HA-DTPH-PEGDA-MMC.
Figure 24A:
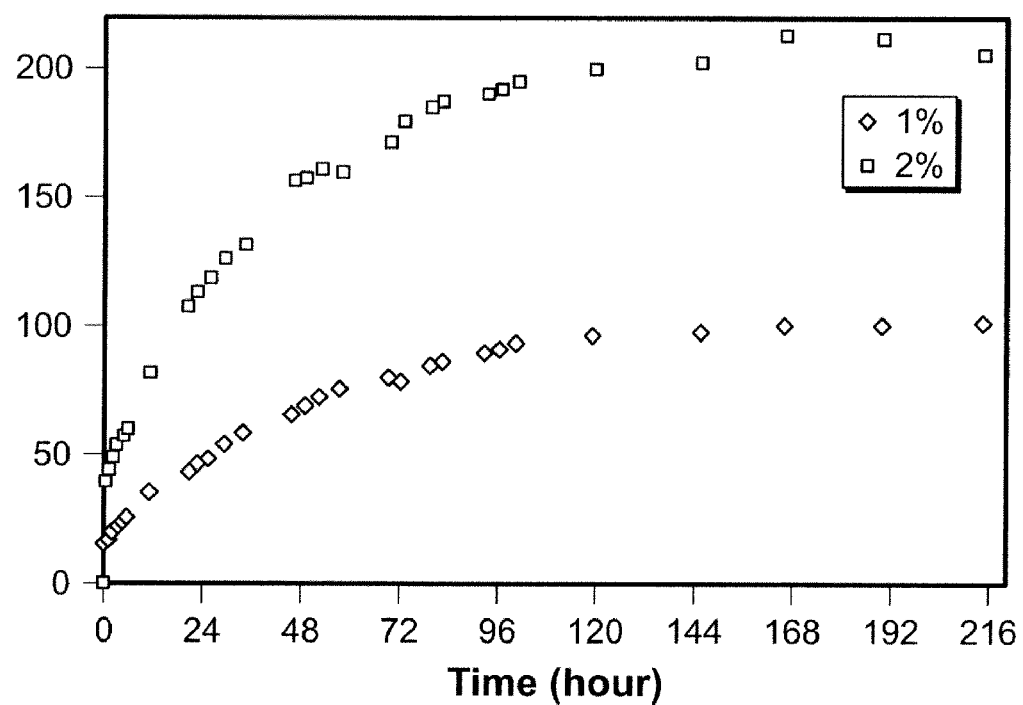
FIGS. 24a and 24b show the results of in vitro MMC release results.
Figure 24B:
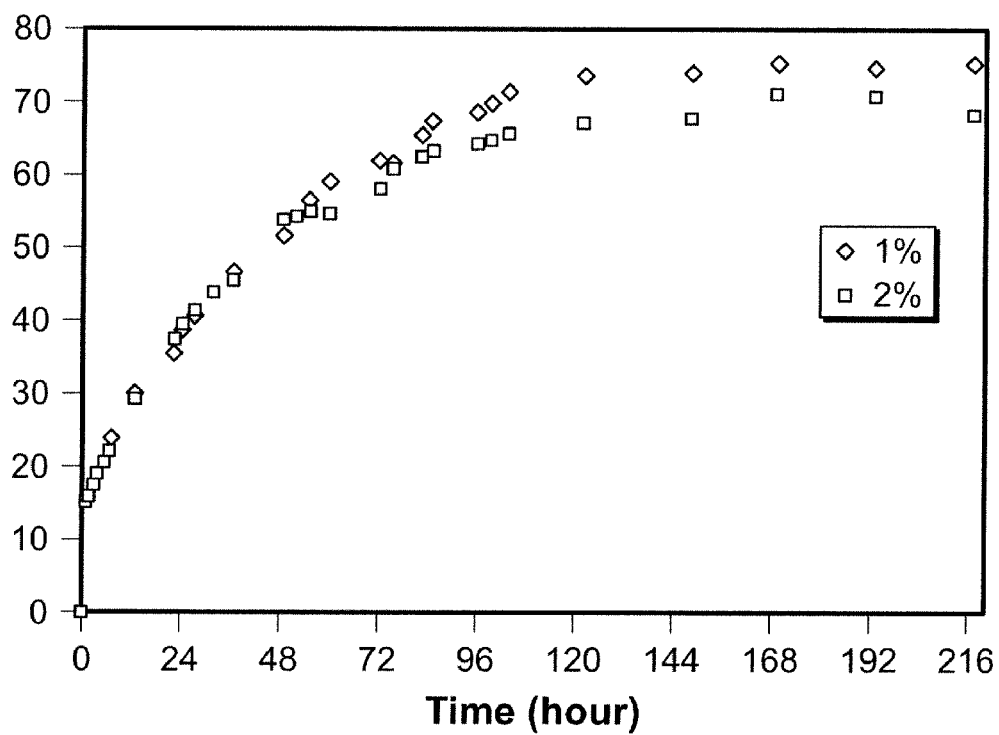

In another aspect, the thiol-reactive compound is any of pharmaceutically-acceptable compounds described above containing at least one thiol-reactive electrophilic group. FIG. 22 depicts one embodiment of this aspect. Mitomycin C (MMC) is converted to the corresponding acrylate (MMC-acrylate). MMC-acrylate is then coupled with the hydrazide-modified hyaluronan thiol compound HA-DTPH to produce HA-DTPH-MMC. HA-DTPH-MMC contains one or more free thiols groups, which then can couple with PEGDA to produce HA-DTPH-PEGDA-MMC, which is depicted in FIG. 23.

In another aspect, the first thiolated macromolecule has the formula III described above, wherein Y is a residue of polysaccharide, and L is $CH_2CH_2$ or $CH_2CH_2CH_2$, and the thiol-reactive compound has the formula V described above, wherein $R^3$ and $R^4$ are, independently, hydrogen or lower alkyl; U and V are, independently, O or $NR^5$, wherein $R^5$ is, independently, hydrogen or lower alkyl; and M is a polyether group. In this aspect, (1) Y is a residue of hyaluronan, and the reaction further comprises reacting gelatin having at least one thiol group with the compound having the formula V; (2) the polysaccharide includes a first polysaccharide and second polysaccharide having the formula I, wherein in the first polysaccharide, Y is a residue of a first sulfated-glycosaminoglycan, and in the second polysaccharide, Y is a residue of a second sulfated-glycosaminoglycan, wherein the first and second sulfated-glycosaminoglycans are the same or different; (3) the polysaccharide includes a first polysaccharide and second polysaccharide having the formula L, wherein in the first polysaccharide. Y is a residue of hyaluronan, and in the second polysaccharide, Y is a residue of a sulfated-glycosaminoglycan; or (4) further reacting a protein, an extracellular matrix protein, or growth factor having at least one thiol group with the compound having the formula V.

In another aspect, described herein is a method for coupling a compound by reacting a first thiolated macromolecule having at least one thiol-reactive electrophilic functional group with at least one compound having at least two thiol groups.

Any of the macromolecules and thiol-reactive electrophilic functional groups described above can be used in this aspect. In this aspect, the first thiolated macromolecule having at least one thiol-reactive electrophilic functional group and the thiolated compound have the formula I

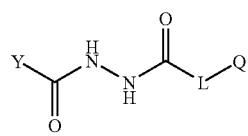

wherein
Y is a residue of the macromolecule;
Q is the thiol-reactive electrophilic function group or an SH group; and
L is a polyalkylene group, a polyether group, a polyamide group, a polyimino group, a polyester, an aryl group, of a polythioether group.

In one aspect, when Q is thiol-reactive electrophilic functional group, Y is hyaluronan and L is $CH_2CH_2$ or $CH_2CH_2CH_2$. In another aspect, Q is an acrylate, a methacrylate, an acrylamide, or a methacrylamide.

In one aspect, examples of compounds having at least two thiol groups include, but are not limited to, propane-1,3-dithiol, polyethylene glycol-α,Ω-dithiol, para, ortho, or meta-bisbenzyl thiol, dithiothreitol, a peptide containing two or more cysteine residues, or dendrimeric thiols.

The compounds produced by coupling a thiolated compound with a compound having at least one thiol-reactive electrophilic functional group possess at least one fragment of the formula VII

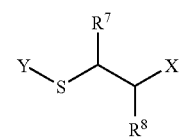

wherein
$R^7$ and $R^8$ are, independently, hydrogen or lower alkyl;
X is an electron-withdrawing group; and
Y is a residue of a macromolecule.

In this aspect, X and Y in formula VII can be any of the electron-withdrawing groups and macromolecules, respectively, described above. In one aspect, Y is a residue of a polysaccharide such as hyaluronan or a sulfated-glycosaminoglycan. In another aspect. $R^7$ is hydrogen and $R^8$ is hydrogen or methyl. In another aspect, Y is a residue of hyaluronan or a sulfated-glycosaminoglycan; $R^7$ is hydrogen; $R^8$ is hydrogen or methyl; and X is an ester group or an amide group.

In one aspect, the fragment has the formula IV

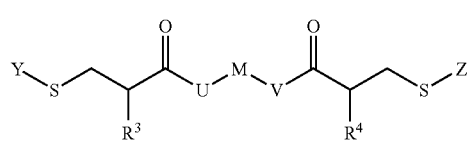

wherein
$R^3$ and $R^4$ are, independently, hydrogen or lower alkyl;
U and V are, independently, O or $NR^5$, wherein $R^5$ is, independently, hydrogen or lower alkyl;

Y is a residue of a protein;

Z is a polysaccharide residue or a residue of synthetic polymer; and

M is a polyalkylene group, a polyether group, a polyamide group, a polyester group, a polyimino group, an aryl group, or a polythioether group.

In one aspect, Y in formula IV has the formula IX

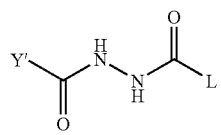

wherein

Y' is a residue of a protein, where the protein is any of the proteins described above;

L is a polyalkylene group, a polyether group, a polyamide group, a polyester group, a polyimino group, an aryl group, or a polythioether group, wherein the L group is covalently bonded to the sulfur atom.

In one aspect, Z in formula IV has the formula X

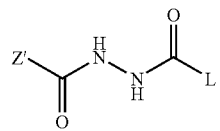

wherein

Z' is a polysaccharide residue or a residue of a synthetic polymer; and

L is a polyalkylene group, a polyether group, a polyamide group, a polyester group, a polyimino group, an aryl group, or a polythioether group, wherein the L group is covalently bonded to the sulfur atom.

In one aspect, the reaction between the thiol reactive compound and thiol compound is generally conducted at a pH of from 7 to 12, 7.5 to 11, 7.5 to 10, or 7.5 to 9.5, or a pH of 8. In one aspect, the solvent used can be water (alone) or an aqueous containing organic solvent. In one aspect, when the mixed solvent system is used, a base such as a primary, secondary, or tertiary amine can used. In one aspect, an excess of thiol compound is used relative to the thiol-reactive compound in order to ensure that all of the thiol-reactive compound is consumed during the reaction. Depending upon the selection of the thiol reactive compound, the thiol compound, the pH of the reaction, and the solvent selected, coupling can occur from within minutes to several days. If the reaction is performed in the presence of an oxidant, such as air, the thiol compound can react with itself or another thiol compound via oxidative addition to form a disulfide linkage in addition to reacting with the thiol-reactive compound.

III. Crosslinked Proteins

Described herein are methods for coupling a protein with another molecule using hydrazide compounds. In one aspect, a protein having at least one hydrazide-reactive group is reacted with a compound having at least one hydrazide group. In another aspect, a protein having at least one hydrazide group is reacted with a compound having at least one hydrazide-reactive group. In one aspect, the hydrazide-reactive group can be a —COOH group (or the salt or ester thereof), an aldehyde group, or a ketone group. The techniques disclosed in international publication nos. WO 02/06373 A1 and WO 02/090390 A1, which are incorporated by reference in their entireties, can be used in this aspect.

In one aspect, the coupled protein has the formula XI

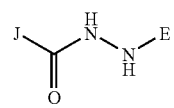

wherein

J comprises a protein residue; and

E comprises a fluorescent tag, a radiolabel, a targeting moiety, a lipid, a peptide, a radionuclide chelator with a radionuclide, a spin-label, a PEG camouflage, a metal surface, a glass surface, a plastic surface, or a combination thereof.

The protein residue can be any protein that has at least one hydrazide-reactive group or at least one hydrazide group; In one aspect, the protein can be an extracellular matrix protein, a partially hydrolyzed extracellular matrix protein, or a chemically-modified extracellular matrix protein. In another aspect, the protein is collagen, elastin, decorin, laminin, or fibronectin.

In one aspect, E in formula XI is a reporter group. Examples of reporter groups include, but are not limited to, a fluorescent tag, a radiolabel, a targeting moiety, a lipid, a peptide, a radionuclide chelator with a radionuclide, a spin-label, a PEG camouflage, a glass surface, a plastic surface, or a combination thereof. Examples of hydrazide-modified fluorescent groups include, but are not limited to, BODIPY-hydrazide, fluorescein hydrazide, or NBD-hexanoyl-hydrazide. Examples of hydrazide-modified radiolabels include, but are not limited to, 125I-tyrosine-hydrazide, 3H-acetyl-hydrazide, or $^{14}$C-acetyl-hydrazide. Examples of hydrazide-modified targeting moieties include, but are not limited to, 6-aminohexanoylhydrazide (Z) of integrin targeting peptide, such as ZYRGDS, Z-tat decapeptide for cell penetration, Z-GFLG for lysosome targeting, HA oligosaccharide hydrazide for CD-44 cancer targeting, or N—Ac glucosamine derivative for liver targeting. Examples of hydrazide-modified lipids include, but are not limited to, hydrazide of 2'-succinate of Taxol or 2'succinate of a glucucorticosteroids, alkanoic or perfluoroalkanoate hydrazides, phosphatidylserine hydrazide, or cholic acid hydrazide. Examples of hydrazide-modified radionuclides include, but are not limited to the reaction product between DTPA anhydride and hydrazine to produce the corresponding hydrazide, coupling the hydrazide to a protein, then adding a nuclide such as In-111, Tc-99m, or Y-90. Examples of spin labels include, but are not limited to, proxyl or doxyl groups. Examples of glass surfaces include, but are not limited to, glass silanized with an epoxy or activated ester or a thiol-reactive electrophilic functional group, beads, or coverslips. Examples of plastics include, but are not limited to, plasma-etched polypropylene, chemically-modified polystyrene with hydrazide, or any other plastic material. In another aspect, E is a crosslinkable thiol reactive-electrophilic groups such, but not limited to acrylic hydrazide or methacrylic hydrazide.

In another aspect, described herein is a kit including (1) a compound having at least one hydrazide group; (2) a condensing agent; (3) a buffer reagent; and (4) a purification column. In one aspect, the compound can be any compound having at least one hydrazide group and at least one of the reporter groups described above. Use of the kit generally involves admixing components (1)-(3) together with a protein having at least one hydrazide-reactive group. Components (1)-(3) and the protein can be added in any order. After the protein and the compound having at least one hyrazide group have reacted with one another to produce the coupled protein, the coupled protein is then purified by passing the admixture containing the coupled protein through a purification column. Purification columns and techniques for using the same are known in the art.

IV. Pharmaceutical Compositions

In one aspect, any of the compounds produced by the methods described above can include at least one pharmaceutically-acceptable compound. The resulting pharmaceutical composition can provide a system for sustained, continuous delivery of drugs and other biologically-active agents to tissues adjacent to or distant from the application site. The biologically-active agent is capable of providing, a local or systemic biological, physiological or therapeutic effect in the biological system to which it is applied. For example, the agent can act to control infection or inflammation, enhance cell growth and tissue regeneration, control tumor growth, act as an analgesic, promote anti-cell attachment, and enhance bone growth, among other functions. Additionally, any of the compounds described herein can contain combinations of two or more pharmaceutically-acceptable compounds.

In one aspect, the pharmaceutically-acceptable compounds can include substances capable of preventing an infection systemically in the biological system or locally at the defect site, as for example, anti-inflammatory agents such as, but not limited to, pilocarpine, hydrocortisone, prednisolone, cortisone, diclofenac sodium, indomethacin, 6$\alpha$-methyl-prednisolone, corticosterone, dexamethasone, prednisone, and the like; antibacterial agents including, but not limited to, penicillin, cephalosporins, bacitracin, tetracycline, doxycycline, gentamycin, chloroquine, vidarabine, and the like; analgesic agents including, but not limited to, salicylic acid, acetaminophen, ibuprofen, naproxen, piroxicam, flurbiprofen, morphine, and the like; local anesthetics including, but not limited to, cocaine, lidocaine, benzocaine, and the like; immunogens (vaccines) for stimulating antibodies against hepatitis, influenza, measles, rubella, tetanus, polio, rabies, and the like; peptides including, but not limited to, leuprolide acetate (an LH-RH agonist), nafarelin, and the like. All compounds are available from Sigma Chemical Co. (Milwaukee, Wis.).

Additionally, a substance or metabolic precursor which is capable of promoting growth and survival of cells and tissues or augmenting the functioning of cells is useful, as for example, a nerve growth promoting substance such as a ganglioside, a nerve growth factor, and the like; a hard or soft tissue growth promoting agent such as fibronectin (FN), human growth hormone (HGH), a colony stimulating factor, bone morphogenic protein, platelet-derived growth factor (PDGF), insulin-derived growth factor (IGF-I, IGF-II), transforming growth factor-alpha (TGF-alpha), transforming growth factor-beta (TGF-beta), epidermal growth factor (EGF), fibroblast growth factor (FGF), interleukin-1 (IL-1), vascular endothelial growth factor (VEGF) and keratinocyte growth factor (KGF), dried bone material, and the like; and antineoplastic agents such as methotrexate, 5-fluorouracil, adriamycin, vinblastine, cisplatin, tumor-specific antibodies conjugated to toxins, tumor necrosis factor, and the like.

Other useful substances include hormones such as progesterone, testosterone, and follicle stimulating hormone (FSH) (birth control, fertility-enhancement), insulin, and the like; antihistamines such as diphenhydramine, and the like; cardiovascular agents such as papaverine, streptokinase and the like; anti-ulcer agents such as isopropamide iodide, and the like; bronchodilators such as metaproternal sulfate, aminophylline, and the like; vasodilators such as theophylline, niacin, minoxidil, and the like; central nervous system agents such as tranquilizer. B-adrenergic blocking agent, dopamine, and the like; antipsychotic agents such as risperidone, narcotic antagonists such as naltrexone, naloxone, buprenorphine; and other like substances. All compounds are available from Sigma Chemical Co. (Milwaukee, Wis.).

The pharmaceutical compositions can be prepared using techniques known in the art. In one aspect, the composition is prepared by admixing a compound described herein with a pharmaceutically-acceptable compound. The term "admixing" is defined as mixing the two components together so that there is no chemical reaction or physical interaction. The term "admixing" also includes the chemical reaction or physical interaction between the compound and the pharmaceutically-acceptable compound. Covalent bonding to reactive therapeutic drugs, e.g. those having reactive carboxyl groups, can be undertaken on the compound. For example, first, carboxylate-containing chemicals such as anti-inflammatory drugs ibuprofen or hydrocortisone-hemisuccinate can be converted to the corresponding N-hydroxysuccinimide (NHS) active esters and can further react with the $NH_2$ group of the dihydrazide-modified polysaccharide. Second, non-covalent entrapment of a pharmacologically active agent in a cross-linked polysaccharide is also possible. Third, electrostatic or hydrophobic interactions can facilitate retention of a pharmaceutically-acceptable compound in a modified polysaccharide. For example, the hydrazido group can non-covalently interact, e.g., with carboxylic acid-containing steroids and their analogs, and anti-inflammatory drugs such as Ibuprofen (2-(4-iso-butylphenyl) propionic acid). The protonated hydrazido group can form salts with a wide variety of anionic materials such as proteins, heparin or dermatan sulfates, oligonucleotides, phosphate esters, and the like.

It will be appreciated that the actual preferred amounts of active compound in a specified case will vary according to the specific compound being utilized, the particular compositions formulated, the mode of application, and the particular situs and subject being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999).

Pharmaceutical compositions described herein can be formulated in any excipient the biological system or entity can tolerate. Examples of such excipients include, but are not limited to water, saline, Ringer's solution, dextrose solution. Hank's solution, and other aqueous physiologically balanced salt solutions. Nonaqueous vehicles, such as fixed oils; vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol.

Pharmaceutical carriers are known to those skilled in the art. These most typically would be standard carriers for administration to humans, including solutions such as sterile water, saline, and buffered solutions at physiological pH.

Molecules intended for pharmaceutical delivery can be formulated in a pharmaceutical composition. Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally).

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishes, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical earners, aqueous, powder or oily bases, thickeners and the like can be necessary or desirable.

Dosing is dependent on severity and responsiveness of the condition to be treated, but will normally be one or more doses per day, with course of treatment lasting from several days to several months or until one of ordinary skill in the art determines the delivery should cease. Persons of ordinary skill can easily determine optimum dosages, dosing methodologies and repetition rates.

In one aspect, any of the compounds and pharmaceutical compositions can include living cells. Examples of living cells include, but are not limited to, fibroblasts, hepatocytes, chondrocytes, stem cells, bone marrow, muscle cells, cardiac myocytes, neuronal cells, or pancreatic islet cells.

V. Methods of Use

The compounds and pharmaceutical compositions described herein can be used for a variety of uses related to drug delivery, small molecule delivery, wound healing, burn injury healing, and tissue regeneration. The disclosed compositions are useful for situations which benefit from a hydrated, pericellular environment in which assembly of other matrix components, presentation of growth and differentiation factors, cell migration, or tissue regeneration are desirable.

The compounds and pharmaceutical compositions described herein can be placed directly in or on any biological system without purification as it is composed of biocompatible materials. Examples of sites the compounds can be placed include, but not limited to, soft tissue such as muscle or fat; hard tissue such as bone or cartilage: areas of tissue regeneration: a void space such as periodontal pocket: surgical incision or other formed pocket or cavity; a natural cavity such as the oral, vaginal, rectal or nasal cavities, the cul-de-sac of the eye, and the like; the peritoneal cavity and organs contained within, and other sites into or onto which the compounds can be placed including a skin surface defect such as a cut, scrape or burn area. The present compounds can be biodegradeable and naturally occurring enzymes will act to degrade them over time. Components of the compound can be "bioabsorbable" in that the components of the compound will be broken down and absorbed within the biological system, for example, by a cell, tissue and the like. Additionally, the compounds, especially compounds that have not been rehydrated, can be applied to a biological system to absorb fluid from an area of interest.

The compounds described herein can be used as a carrier for a wide variety of releasable biologically active substances having curative or therapeutic value for human or non-human animals. Many of these substances which can be carried by the compound are discussed above. Included among biologically active materials which are suitable for incorporation into the gels of the invention are therapeutic drugs, e.g., anti-inflammatory agents, anti-pyretic-agents, steroidal and non-steroidal drugs for anti-inflammatory use, hormones, growth factors, contraceptive agents, antivirals, antibacterials, antifungals, analgesics, hypnotics, sedatives, tranquilizers, anti-convulsants, muscle relaxants, local anesthetics, antispasmodics, antiulcer drugs, peptidic agonists, sympathiomimetic agents, cardiovascular agents, antitumor agents, oligonucleotides and their analogues and so forth. A biologically active substance is added in pharmaceutically active amounts.

In one aspect, the compounds and compositions described herein can be used for the delivery of living cells to a subject. Any of the living cells described above can be used in the aspect.

In one aspect, the compounds and compositions can be used for the delivery of growth factors, and molecules related to growth factors. For example the growth factors can be a nerve growth promoting substance such as a ganglioside, a nerve growth factor, and the like; a hard or soft tissue growth promoting agent such as fibronectin (FN), human growth hormone (HGH), a colony stimulating factor, bone morphogenic protein, platelet-derived growth factor (PDGF), insulin-derived growth factor (IGF-I, IGF-II), transforming growth factor-alpha (TGF-alpha), transforming growth factor-beta (TGF-beta), epidermal growth factor (EGF), Fibroblast growth factor (FGF), interleukin-1 (IL-1). Preferred growth factors are bFGF and TGF-$\beta$. Also preferred are vascular endothelial growth factor (VEGF) and keratinocyte growth factor (KGF).

In another aspect, anti-inflammatories bearing carboxyl groups such as ibuprofen, naproxen, ketoprofen and indomethacin can be used. Other biologically active substances are peptides, which are naturally Occurring, non-naturally occurring or synthetic polypeptides or their isosteres, such as small peptide hormones or hormone analogues and protease inhibitors. Spermicides, antibacterials, antivirals, antifungals and antiproliferatives such as fluorodeoxyuracil and adriamycin can also be used. These, substances are all known in the art. Compounds are available from Sigma Chemical Company (St. Louis, Mo.).

The term "therapeutic drugs" as used herein is intended to include those defined in the Federal Food, Drug and Cosmetic Act. The United States Pharmacopeia (USP) and the National Formulary (NF) are the recognized standards for potency and purity for most common drug products.

In one aspect, the pharmaceutically acceptable compound is pilocarpine, hydrocortisone, prednisolone, cortisone, diclofenac sodium, indomethacin. 6$\alpha$-methyl-prednisolone, corticosterone, dexamethasone and prednisone. However, methods are also provided wherein delivery of a pharmaceutically-acceptable compound is for a medical purpose selected from the group of delivery of contraceptive agents, treating postsurgical adhesions, promoting skin growth, preventing scarring, dressing wounds, conducting viscosurgery, conducting viscosupplementation, engineering tissue.

The rate of drug delivery depends on the hydrophobicity of the molecule being released. Hydrophobic molecules, such as dexamethazone and prednisone are released slowly from the compound as it swells in an aqueous environment, while hydrophilic molecules, such as pilocarpine, hydrocortisone, prednisolone, cortisone, diclofenac sodium, indomethacin, 6∝-methyl-prednisolone and corticosterone, are released quickly. The ability of the compound to maintain a slow, sustained release of steroidal anti-inflammatories makes the compounds described herein extremely useful for wound healing after trauma or surgical intervention. Additionally, the compound can be used as a barrier system for enhancing cell growth and tissue regeneration.

In certain methods the delivery of molecules or reagents related to angiogenesis and vascularization are achieved. Disclosed are methods for delivering agents, such as VEGF, that stimulate microvascularization. Also disclosed are methods for the delivery of agents that can inhibit angiogenesis and vascularization, such as those compounds and reagents useful for this purpose disclosed in but not limited to U.S. Pat. No. 6,174,861 for "Methods of inhibiting angiogenesis via increasing in vivo concentrations of endostatin protein;" U.S. Pat. No. 6,086,865 for "Methods of treating angiogenesis-induced diseases and pharmaceutical compositions thereof;" U.S. Pat. No. 6,024,688 for "Angiostatin fragments and method of use;" U.S. Pat. No. 6,017,954 for "Method of treating tumors using O-substituted fumagillol derivatives;" U.S. Pat. No. 5,945,403 for "Angiostatin fragments and method of use;" U.S. Pat. No. 5,892,069 "Estrogenic compounds as anti-mitotic agents;" for U.S. Pat. No. 5,885,795 for "Methods of expressing angiostatic protein;" 5,861,372 for "Aggregate angiostatin and method of use;" U.S. Pat. No. 5,854,221 for "Endothelial cell proliferation inhibitor and method of use;" U.S. Pat. No. 5,854,205 for "Therapeutic antiangiogenic compositions and methods;" U.S. Pat. No. 5,837,682 for "Angiostatin fragments and method of use," U.S. Pat. No. 5,792,845 for "Nucleotides encoding angiostatin protein and method of use;" U.S. Pat. No. 5,733,876 for "Method of inhibiting angiogenesis;" U.S. Pat. No. 5,698,586 for "Angiogenesis inhibitory agent;" U.S. Pat. No. 5,661,143 for "Estrogenic compounds as anti-mitotic agents," U.S. Pat. No. 5,639,725 for "Angiostatin protein;" U.S. Pat. No. 5,504,074 for "Estrogenic compounds as anti-angiogenic agents;" U.S. Pat. No. 5,290,807 for "Method for regressing angiogenesis using o-substituted fumagillol derivatives;" and U.S. Pat. No. 5,135,919 for "Method and a pharmaceutical composition for the inhibition of angiogenesis" which are herein incorporated by reference for the material related to molecules for angiogenesis inhibition.

Described herein are methods for improving wound healing in a subject in need of such improvement by contacting any of the compounds or pharmaceutical compositions described herein with a wound of a subject in need of wound healing improvement. Also provided are methods to deliver at least one pharmaceutically-acceptable compound to a patient in need of such delivery by contacting any of the compounds or pharmaceutical compositions described herein with at least one tissue capable of receiving said pharmaceutically-acceptable compound.

The disclosed compositions can be used for treating a wide variety of tissue defects in an animal, for example, a tissue with a void such as a periodontal pocket, a shallow or deep cutaneous wound, a surgical incision, a bone or cartilage defect, and the like. For example, the compounds described herein can be in the form of a hydrogel film. The hydrogel film can be applied to a defect in bone tissue such as a fracture in an arm or leg bone, a defect in a tooth, a cartilage defect in the joint, ear, nose, or throat, and the like. The hydrogel film composed of the compound described herein can also function as a barrier system for guided tissue regeneration by providing a surface on or through which the cells can grow. To enhance regeneration of a hard tissue such as bone tissue, it is preferred that the hydrogel film provides support for new cell growth that will replace the matrix as it becomes gradually absorbed or eroded by body fluids.

The hydrogel film composed of a compound described herein can be delivered onto cells, tissues, and/or organs, for example, by injection, spraying, squirting, brushing, painting, coating, and the like. Delivery can also be via a cannula, catheter, syringe with or without a needle, pressure applicator, pump, and the like. The compound can be applied onto a tissue in the form of a film, for example, to provide a film dressing on the surface of the tissue, and/or to adhere to a tissue to another tissue or hydrogel film, among other applications;

In one aspect, the compounds described herein are administered via injection. For many clinical uses, when the compound is in the form of a hydrogel film, injectable hydrogels are preferred for three main reasons. First, an injectable hydrogel could be formed into any desired shape at the site of injury. Because the initial hydrogels can be sols or moldable putties, the systems can be positioned in complex shapes and then subsequently crosslinked to conform to the required dimensions. Second, the hydrogel would adhere to the tissue during gel formation, and the resulting mechanical interlocking arising from surface microroughness would strengthen the tissue-hydrogel interface. Third, introduction of an in situ-crosslinkable hydrogel could be accomplished using needle or by laparoscopic methods, thereby minimizing the invasiveness of the surgical technique.

The compounds described herein can be used to treat periodontal disease, gingival tissue overlying the root of the tooth can be excised to form an envelope or pocket, and the composition delivered into the pocket and against the exposed root. The compounds can also be delivered to a tooth defect by making an incision through the gingival tissue to expose the root, and then applying the material through the incision onto the root surface by placing, brushing, squirting, or other means.

When used to treat a defect on skin or other tissue, the compounds described herein can be in the form of a hydrogel film that can be placed on top of the desired area. In this aspect, the hydrogel film is malleable and can be manipulated to conform to the contours of the tissue defect.

The compounds described herein can be applied to an implantable device such as a suture, claps, prosthesis, catheter, metal screw, bone plate, pin, a bandage such as gauze, and the like, to enhance the compatibility and/or performance or function of an implantable device with a body tissue in an implant site. The compounds can be used to coat the implantable device. For example, the compounds could be used to coat the rough surface of an implantable device to enhance the compatibility of the device by providing a biocompatable smooth surface which reduces the occurrence of abrasions from the contact of rough edges with the adjacent tissue. The compounds can also be used to enhance the performance or function of an implantable device. For example, when the compound is a hydrogel film, the hydrogel film can be applied to a gauze bandage to enhance its compatibility or adhesion with the tissue to which it is applied. The hydrogel film can also be applied around a device such as a catheter or colostomy that is inserted through an incision into the body to help secure the catheter/colosotomy in place and/or to fill the void between the device and tissue and form a tight seal to reduce bacterial infection and loss of body fluid.

It is understood that the disclosed compositions and methods can be applied to a subject in need of tissue regeneration. For example, cells can be incorporated into the compounds described herein for implantation. In one aspect the subject is a mammal. Preferred mammals to which the compositions and methods, apply are mice, rats, cows or cattle, horses, sheep, goats, cats, dogs, and primates, including apes, chimpanzees, orangutans, and humans. In another aspect, the compounds and compositions described herein can be applied to birds.

When being used in areas related to tissue regeneration such as wound or burn healing, it is not necessary that the disclosed methods and compositions eliminate the need for one or more related accepted therapies. It is understood that any decrease in the length of time for recovery or increase in the quality of the recovery obtained by the recipient of the disclosed compositions or methods has obtained some benefit. It is also understood that some of the disclosed compositions and methods can be used to prevent or reduce fibrotic adhesions occurring as a result of wound closure as a result of trauma, such surgery. It is also understood that collateral affects provided by the disclosed compositions and compounds are desirable but not required, such as improved bacterial resistance or reduced pain etc.

It is understood that any given particular aspect, of the disclosed compositions and methods can be easily compared to the specific examples and embodiments disclosed herein, including the non-polysaccharide based reagents discussed in the Examples. By performing such a comparison, the relative efficacy of each particular embodiment can be easily determined. Particularly preferred assays for the various uses are those assays which are disclosed in the Examples herein, and it is understood that these assays, while not necessarily limiting, can be performed with any of the compositions and methods disclosed herein.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

I. Materials

Fermentation-derived hyaluronan (HA, sodium salt, $M_w$ 1.5 MDa) was obtained from Clear Solutions Biotech, Inc. (Stony Brook, N.Y.). 1-Ethyl-3-[3-(dimethylamino)propyl] carbodiimide (EDCI), 3,3'-dithiobis(propanoic acid), 4,4-dithiobis(butanoic acid), and polyethylene glycol) acrylate ($M_w$ 375), and hydrazine hydrate were from Aldrich Chemical Co. (Milwaukee, Wis.). Dulbecco's phosphate buffered saline (PBS), bovine testicular hyaluronidase (HAse, 330 U/mg) and blue dextran ($M_w$ 200,000) was from Sigma Chemical Co. (St. Louis, Mo.). Dithiothreitol (DTT) was from Diagnostic Chemicals Limited (Oxford, Conn.). 5,5'-Dithio-bis(2-nitrobenzoic acid) (DTNB) was from Acros (Houston, Tex.). 3,3'-dithiobis(propanoic dihydrazide) (DTP) and 4,4'-dithiobis(butyric dihydrazide) (DTB) was synthesized as previously described in Vercruysse K P, Marecak D M, Marecek J F, and Prestwich G D. "Synthesis and in vitro degradation of new polyvalent hydrazide cross-linked hydrogels of hyaluronic acid," Bioconjugate Chem 1997; 8:686-694, which is incorporated by reference in its entirety. Poly(ethylene glycol)-diacrylate (PEGDA), poly(ethylene glycol)-dimethacrylate (PEGDM), poly(ethylene glycol)-diacrylamide (PEGDAA) and poly(ethylene glycol)-dimethacrylamide (PEGDMA) were synthesized from poly (ethylene glycol) or poly(ethylene glycol) diamine (Mw 3,400, Shearwater Polymers) as described in Elbert D L and Hubbell J A. "Conjugate addition reactions combined with free-radical crosslinking for the design of materials for tissue engineering," Biomacromolecules 2001; 2:430-441, which is incorporated by reference in its entirety. Gelatin from bovine skin (Types B and A, gel strength approx. 225 bloom), Dulbecco's phosphate buffered saline (PBS), cystein, bovine testicular hyaluronidase (HAse, 330 U/mg), bacterial collagenase from *Clostridium histolyticum* (EC 3.4.24.3, 388 U/mg were obtained from Sigma Chemical Co. (St. Louis, Mo.). 3-(4,5-dimethylthiazol-2-yl)-2,5, diphenyl tetrazolium bromide (MTT) were obtained from Sigma Chemical Co. (St. Louis, Mo.). 5,5'-Dithio-bis(2-nitrobenzoic acid) (DTNB) was purchased from Acros (Houston, Tex.).

Analytical Instrumentation. Proton NMR spectral data were obtained using a Varian INOVA 400 at 400 MHz. UV-Vis spectral data were obtained using a Hewlett Packard 8453 UV-visible spectrophotometer (Palo Alto, Calif.). Gel permeation chromatography (GPC) analysis was performed using the following system: Waters 515 HPLC pump, Waters 410 differential refractometer. Waters™ 486 tunable absorbance detector, Ultrahydrogel 250 or 1000 columns (7.8 mm i.d.× 130 cm) (Milford, Mass.). The eluent was 200 mM phosphate buffer (pH 6.5)/MeOH=80:20 (v/v) and the flow rate was 0.3 or 0.5 mL/min. The system was calibrated with standard HA samples provided by Dr. U. Wik (Pharmacia, Uppsala, Sweden). Fluorescence images of viable cells were recorded using a Nikon Eclipse TE300 with epi-fluorescence capabilities. Cell proliferation was determined using a biochemical assay (Cell-Titer 96 Proliferation Kit, Promega, Madison, Wis.), MTT assay, or MTS assay at 550 nm, which was recorded on an OPTI Max microplate reader (Molecular Devices; Sunnyvale, Calif.).

Synthesis of thioacid dihydrazides. The oxidized forms of the required thiol crosslinkers 3,3'-dithiobis(propanoic hydrazide) (DTP) and 4,4'-dithiobis(butanoic hydrazide) (DTB) were synthesized from their diacids as described previously for DTP in Vercruysse, K. P.; Marecak, D. M.; Marecek, J. F.; Prestwich, G. D. *Bioconjugate Chem.* 1997, 8, 686-694, which is incorporated by reference in its entirety. Thus, free dicarboxylic acids were converted into diesters by refluxing in ethanol with acid catalysis. The diesters were hydrazinolyzed with hydrazine hydrate to form the corresponding dihydrazides. DTP (Vercruysse, K. P.; Marecak, D. M.; Marecek, J. F.; Prestwich. G. D. *Bioconjugate Chem.* 1997, 8, 686-694): yield. 92%; $^1$H NMR (400 MHz, DMSO-$d_6$): δ 9.05 (s, 2 H, N—NH—C(O)), δ 4.21 (s, 4 H, NH$_2$—N—C(O)), δ 2.88 (t, 4 H, C(O)—C—CH$_2$—S), δ 2.40 (t, 4 H, N—C(O)—CH$_2$—C). DTB: yield, 52%; $^1$H NMR (400 MHz, DMSO-$d_6$): δ 8.95 (s, 2 H, N—NH—C(O)), δ 4.15 (s, 4 H, NH$_2$—N—C(O)), δ 2.66 (t, 4 H, C—C—CH$_2$—S), δ 2.10 (t, 4 H, C(O)—CH$_2$—C—C), δ 1.82 (p, 4 H, C(O)—C—CH$_2$—C—S); MS-EI, m/z 266.0 (M$^+$, 1.44); 133.0 (SC$_3$H$_6$CON$_2$H$_3^+$, 46.78); 101.0 (C$_3$H$_6$CON$_2$H$_3^+$, 100.0). HRMS for C$_8$H$_{18}$O$_2$S$_2$N$_4$. Found 266.0864; Calcd. 266.0871.

Preparation of low molecular weight (LMW) HA by acid degradation. High molecular weight HA (1.5 MDa) (20 g) was dissolved in 2.0 L distilled water, and the solution pH was adjusted to ca. 0.5 by the addition of concentrated HCl. The degradation was carried out at 37° C., 130 rpm stirring for 24 h. After that, the pH of the solution was adjusted to 7.0 by the addition of 1.0 N NaOH before transfer to dialysis tubing ($M_w$ cut-off 3,500) and dialyzed against water for four days. The solution was then centrifuged, and the supernatant was lyophilized to give 15 g LMW HA ($M_w$ 246 kDa, $M_n$ 120 kDa, polydispersity index 1.97).

II. Disulfide Crosslinked Hyaluronan Hydrogels Via Oxidative Addition

Preparation of Thiolated HA.

Thiolated HA derivatives with different loadings were prepared following a general protocol (FIG. 1). In a representative example, LMW HA (20 g, 50 mmol) was dissolved in 2.0 L of water, 23.8 g of DTP or 26.6 g of DTB (100 mmol) was added while stirring. The pH of the reaction mixture was adjusted to 4.75 by the addition of 1.0 N HCl. Next, 19.2 g of EDCI (100 mmol) in solid form was added. The pH of the reaction mixture was maintained at 4.75 with aliquots of 1.0 N HCl. The reaction was stopped by addition of 1.0 N NaOH, raising the pH of the reaction mixture to 7.0. Then. 100 g DTT (ca. 650 mmol) in solid form was added and the pH of the solution was raised to 8.5 by addition of 1.0 N NaOH. After stirring for 24 h, the pH of the reaction mixture was adjusted to pH 3.5 by the addition of 1.0 N HCl. The acidified solution was transferred to dialysis tubing ($M_w$ cut-off 3,500) and dialyzed exhaustively against dilute HCl (pH 3.5, approximately 0.3 mM) containing 100 mM NaCl, followed by dialysis against dilute HCl, pH 3.5. The solution was then centrifuged, and the supernatant was lyophilized. The purity of thiolated HA (HA-DTPH and HA-DTBH) was measured by GPC and $^1$H NMR, and the degree of substitution (SD) was determined by $^1$H NMR. The free thiols on the side chain of HA-DTPH and HA-DTBH were determined by a modified Ellman method (Butterworth, P. H. W.; Baurn. H.; Porter, J. W. *Arch. Biochem. Biophys.* 1967, 118, 716-723). SD (%) and thiol content (%) were defined as the number of DTP (or DTB) residues and thiols per 100 disaccharide units, respectively. Representative results: HA-DTBH ($M_w$ 165 kDa, $M_n$ 63 kDa, polydispersity index 2.62, SD 72%) and HA-DTPH ($M_w$ 136 kDa, $M_n$ 61 kDa, polydispersity index 2.23, SD 58%). The structures of HA-DTPH and HA-DTBH were confirmed by $^1$H NMR spectroscopy in D$_2$O.

SD was mainly controlled by the molar ratios of HA/DTP/EDC (Table 1). By selecting suitable reaction parameters, the degree of substitution can be controlled over a wide range (28% to 67%) (Table 1). Similar results were also observed in case of DTB-modified HA.

TABLE 1

Optimization of DTP modification of HA.

| molar ratio of HA:DTP:EDCI | reaction time (min) | Degree of substitution (%) |
|---|---|---|
| 1:2:2 | 5 | 28.8 |
| 1:2:2 | 10 | 41.7 |
| 1:2:2 | 30 | 49.2 |
| 1:2:2 | 60 | 54.4 |
| 1:2:2 | 120 | 66.8 |
| 1:1:2 | 10 | 38.9 |
| 1:4:2 | 10 | 42.5 |
| 1:2:1 | 10 | 31.1 |
| 1:2:0.5 | 10 | 26.8 | p$K_a$ determination. The p$K_a$ of thiols in HA-DTPH and HA-DTBH was determined spectrophotometrically based on the UV absorption of thiolates as proposed by Benesch and Benesch (Benesch, R.; Benesch, R. E. *Proc. Nat. Acad. Sci. USA* 1958, 44, 848-853). Solutions of HA-DTPH and HA-DTBH (ca. 5 mg) were dissolved in 100 mL 0.001 N HCl containing 0.1 N NaCl (stable ionic strength). Freshly-prepared solutions were immediately measured in the UV region with a scan from 190 to 300 nm.

Figure 2A:
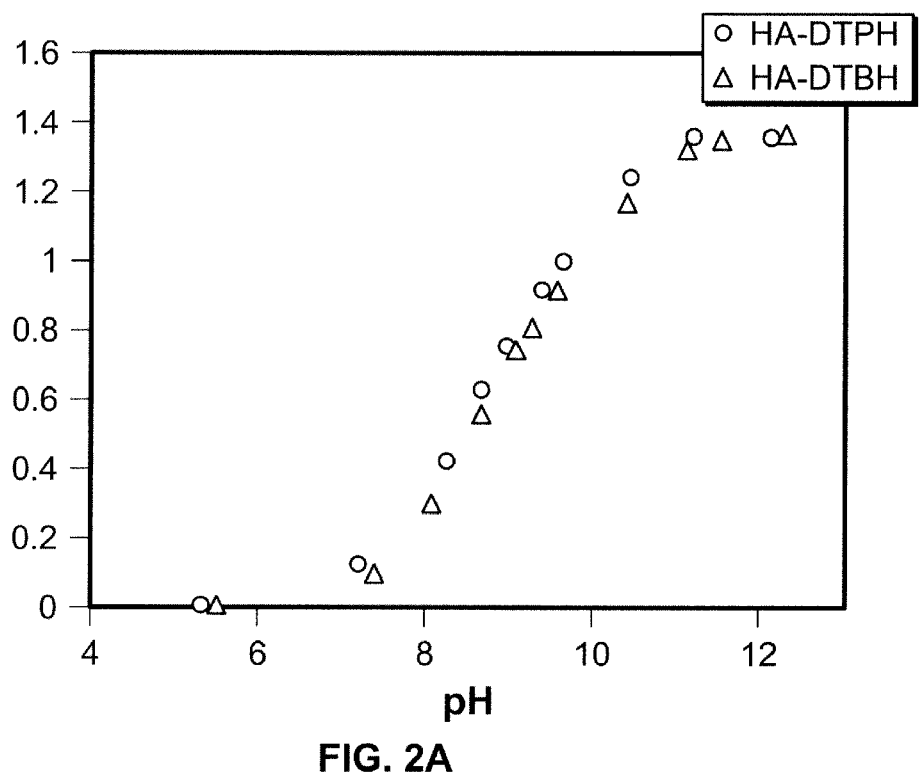
FIG. 2 shows (a) absorption at 242 nm as a function of pH for HA-DTPH and HA-DTBH solution and (b) logarithmic plot of log $[(A_{max}-A_i)/A_i]$ vs. pH. The $pK_a$ values correspond to the intercept with the abscissa.
Figure 2B:
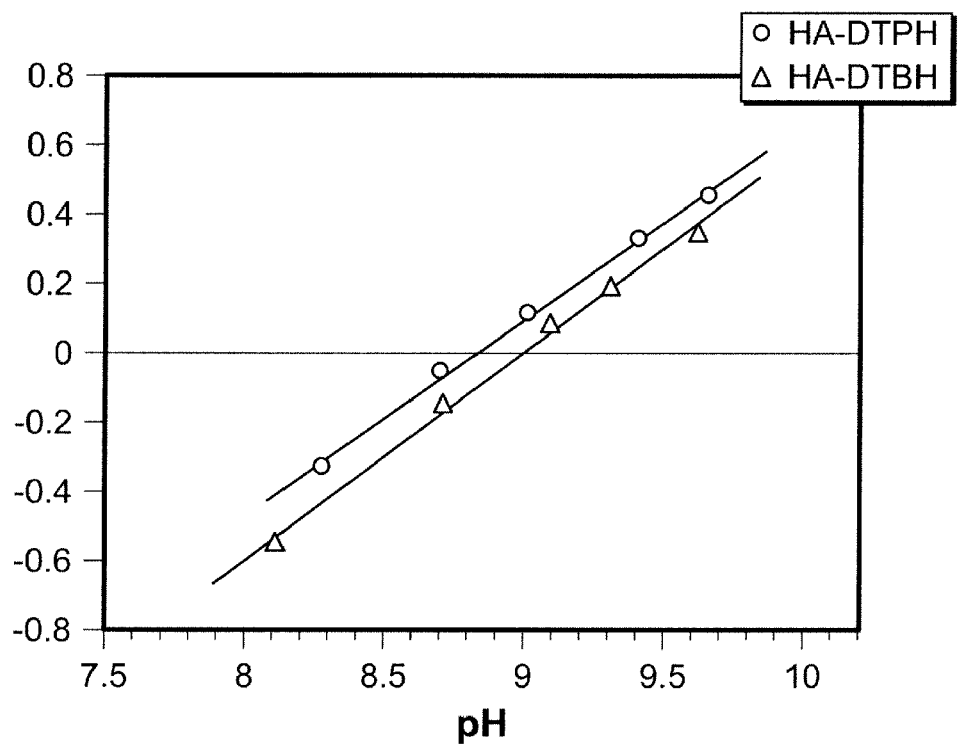

The p$K_a$ values were determined spectrophotometrically based on the UV absorption of thiolates (Benesch). With increasing pH, the absorption of solutions increased abruptly—especially at the pH near the p$K_a$ of thiols (FIG. 2a). According to the procedure reported by Lutolf and co-workers (Lutolf, M. P.; Tirelli, N. Cerritelli, S.; Cavalli, L.; Hubbell, J. A. *Bioconjugate Chem.* 2001, 12, 1051-1056) the intercept with the abscissa in a graphical representation of log|($A_{max}$–$A_i$)/$A_i$| vs. pH yielded the p$K_a$ value. There was good linear approximation of the five central points both for HA-DTPH and HA-DTBH, giving a value of 8.87 for HA-DTPH and 9.01 for HA-DTBH. The p$K_a$ of HA-DTPH was slightly lower than that of HA-DTBH because the thiol in HA-DTPH was more easily activated by the proximity of the amide group (FIG., 2b).

Compared to HA-DTBH, the lower p$K_a$ of thiols in HA-DTPH suggested increased reactivity and increased capability to regenerate the disulfide structure under the same conditions. A qualitative procedure was used to evaluate the reformation of disulfide. When HA-DTPH and HA-DTBH solutions were in contact with air, the viscosity increased and a gel formed due to the oxidation of thiols to disulfide by O$_2$. At higher pH, both HA-DTPH and HA-DTBH solutions more easily formed gels because thiols were converted to more reactive thiolates at higher pH (Table 2). For instance, with 3.0% HA-DTPH solution (SD 58%), the solution at pH 7.0, 8.0, and 90 gelled within 15 min, while at pH 5.0 and 6.0 no obvious increase in viscosity of solution was observed after 30 min (Table 2). The thiols of HA-DTBH were less reactive, and thus the gelation of HA-DTBH solution (3.0% w/v, SD 72%) was sluggish (Table 2).

TABLE 2

The air-induced gelation of HA-DTPH and HA-DTBH solution (3.0% w/v) determined by a test tube inversion method.

| | HA-DTPH | | HA-DTBH | |
|---|---|---|---|---|
| pH | 15 min | 30 min | 15 min | 30 min |
| 5.0 | S | S | S | S |
| 6.0 | S | S | S | S |
| 7.0 | G | G | VS | VS |

TABLE 2-continued

The air-induced gelation of HA-DTPH and HA-DTBH solution (3.0% w/v) determined by a test tube inversion method.

| pH | HA-DTPH | | HA-DTBH | |
|---|---|---|---|---|
| | 15 min | 30 min | 15 min | 30 min |
| 8.0 | G | G | VS | G |
| 9.0 | G | G | VS | G |

S = solution;
G = gel;
VS = highly viscous solution

Gelation of thiolated HA solutions. The solution (flow)-gel (no flow) transition was determined by a flow test utilizing a test tube inverting method reported by Jeong et al. (Jeong, B.; Bae, Y. H; Kim. S: W. *Macromol.* 1999, 32, 7064-7069). HA-DTBH and HA-DTPH were dissolved in PBS to give 3.0% (w/v) solutions under $N_2$ protection. The solution pH was adjusted to 5.0, 6.0, 7.0, 8.0 and 9.0 by 1.0 N NaOH. Freshly-prepared solutions (1.0 mL) with different pH were immediately injected into glass tubes (0.8 cm in diameter, 7.5 cm in length). After exposure to air at room temperature for 15 or 30 min, the test tube was inverted. If no fluidity was visually observed in 1 min. we concluded that that a gel had formed.

Preparation of disulfide-crosslinked HA films. HA-DTBH and HA-DTPH were dissolved in PBS to give 3.0% (w/v) solutions and the solution pH was adjusted to 7.4 by the addition of 1.0 N NaOH. For drug-loaded gels, 0.15% (w/V) blue dextran ($M_w$ 200,000) was included as a model drug. Next, 25 mL of the solution was poured into a 9-cm petri dish and allowed to dry at room temperature. After ca. three days, a film ready. As required, the film was further oxidized by immersion in 0.3% $H_2O_2$ for 1 h. The film was then rinsed with distilled water, cut into 6-mm diameter discs, and dried at room temperature for one day and then at 1 mm Hg for one week, to give films with 0.1 mm thickness.

Swelling determination. Discs of HA-DTBH and HA-DTPH film (6 mm in diameter) were weighed ($W_0$), immersed in glass vials containing 10 mL PBS (pH 7.4), and placed in a shaking incubator at; 37° C., at 300 rpm. At predetermined time intervals, the wet films were weighed ($W_t$) immediately after the removal of the surface water by blotting between two pieces of filter paper. Swelling ratio (R) was defined as $W_t/W_0$.

Figure 3:
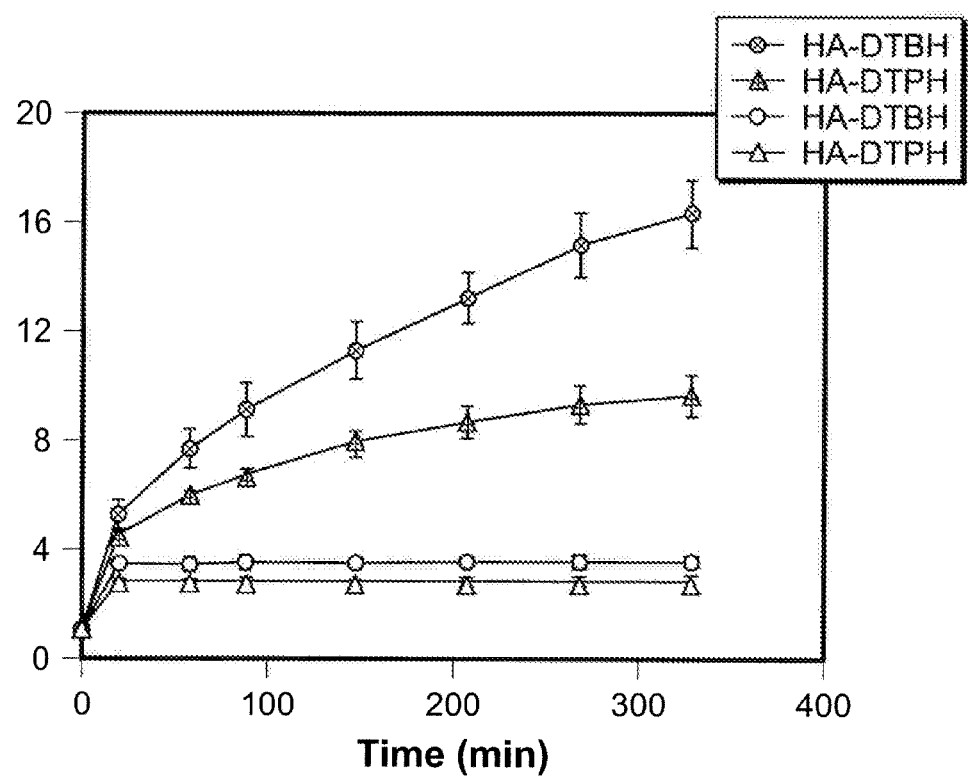
FIG. 3 shows the swelling of HA-DTPH and HA-DTBH films in PBS at pH 7.4. The open circles and triangles are the films coupled via oxidation with 0.3% $H_2O_2$ after air oxidation, and the closed circles and triangles are films coupled by air oxidation only.

The swelling of HA-DTPH and HA-DTBH films in PBS was in accordance with the disulfide content in the films as shown in FIG. 3. The air oxidized films swelled significantly because of low degree of crosslinking, with a swelling ratio at 5.5 h of 16.2 for HA-DTBH film and 9.5 for HA-DTPH. These ratios are similar to PEG-dialdehyde crosslinked HA adipic dihydrazide hydrogels used for drug release (Luo, Y.; Kirker. K. R.; Prestwich, G. D. *J. Controlled Rel.* 2000, 69, 169-184) and wound repair (Kirker, K. R.; Luo, Y.; Nieison, J. H.; J. Shelby; Prestwich, G. D. *Biomaterials* 2002, 25, 3661-3671). After $H_2O_2$ oxidation, the swelling ratio decreased to 3.5 for the HA-DTBH film and 2.9 for HA-DTPH film.

Disulfide content determination. Discs of HA-DTBH and HA-DTPH film were degraded by acid hydrolysis (0.1 N HCl). The total sulfur content (disulfide plus thiol) was measured using 2-nitro-5-thiosulphobenzoate (NTSB) according to Thannhauser et al. (Thannhauser, T. W.; Konishi, Y.; Scheraga, H. A. *Meth. Enzymol.* 1987, 143, 115-119). In addition, the free thiol content was measured by the Ellman method (Ellman, G. L. *Arch. Biochem. Biophys.* 1958, 74, 443-450). Disulfide content was calculated from the difference between total sulfur content and free thiol content.

Figure 4:
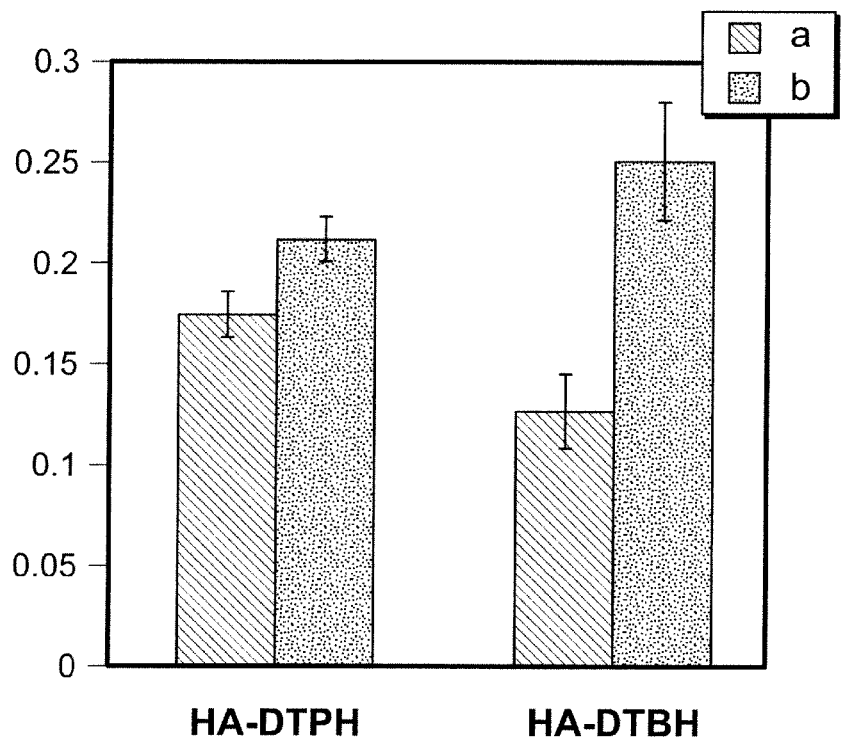
FIG. 4 shows the disulfide content in HA-DTPH and HA-DTBH films. Key: a=air oxidation only; b=air oxidation followed by oxidation with $H_2O_2$.

FIG. 4 shows the oxidation with dilute $H_2O_2$ increased the number of disulfide linkages. For example, the disulfide content in HA-DTPH film increased from 0.175 to 0.212 mmol/g after the oxidation of $H_2O_2$. In the case of HA-DTBH film, fewer disulfide linkages were formed due to air oxidation because the thiol was less reactive (the value was 0.125 mmol/g); however, this could be increased significantly to 0.25 mmol/g by oxidation with $H_2O_2$. However, following the $H_2O_2$ oxidizing procedure, no additional thiol groups are detected within both the HA-DTPH and the HA-DTBH films, and only ca. 30 to 40% of the available thiols formed disulfide bonds. This suggests that $H_2O_2$ oxidation of thiol groups not only created new disulfide bridges, but led to the production of S-oxidized sulfenic or sulfonic acids that would not be detected using NTSB and DTNB (Capozzi, G.; Modena. G. In *The Chemistry of the Thiol Group Part II*; Patai. S., Ed.; Wiley: New York. 1974; pp 785-839).

Blue dextran release studies. Drug-loaded 6-mm discs of HA-DTBH and HA-DTPH film were immersed in glass bottles containing 2 mL release media, and placed in an incubator at 37° C., at 300 rpm. At predetermined time intervals. 1 mL supernatant solution was removed, and the blue dextran content was determined by UV-vis absorption at 625 nm. Then, 1 mL blank release media was added buck to maintain constant volume. Release media: PBS containing 0, 10 and 50 mM DTT (the media pH was adjusted to pH 7.4 by adding 10 N NaOH) or PBS containing hyaluronidase (HAse, 100 U/mL).

Figure 5:
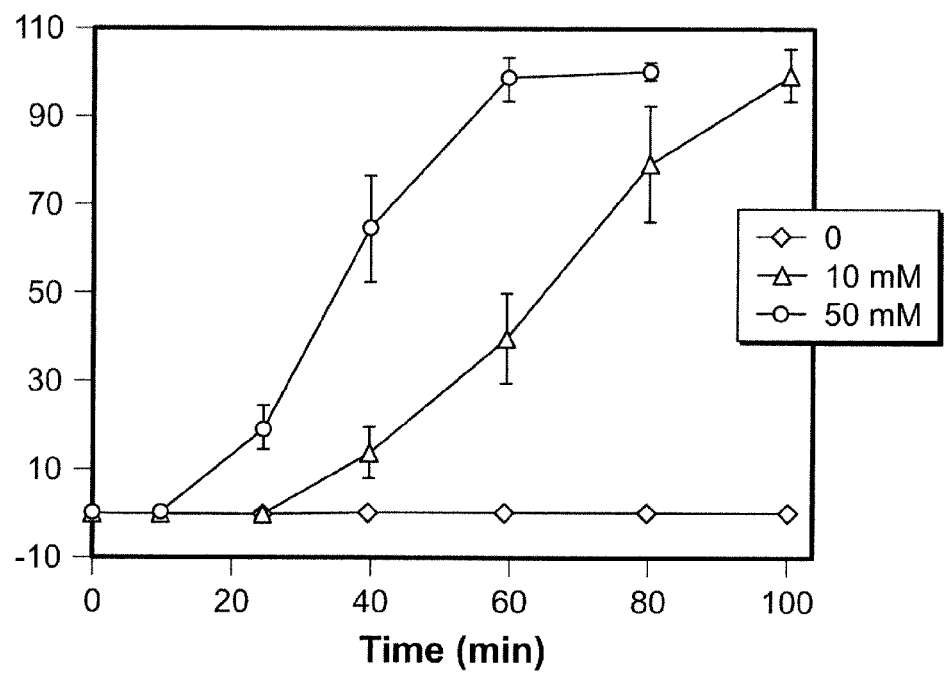
FIG. 5 shows the release of blue dextran from HA-DTPH in PBS containing different concentrations of DTT at pH 7.4.

To further confirm the HA-DTPH and HA-DTBH films were crosslinked by reversible disulfide linkages, the hydrogel films were incubated in PBS that contained different concentrations of DTT at pH 7.4 (data not shown). Even with DTT concentration as low as 10 mM, films generated from both air and $H_2O_2$ oxidation swelled significantly and dissolved gradually due to reduction of disulfide by DTT. As the gels dissolved, a model drug (blue dextran $M_w$ 200,000) that had been non-covalently entrapped in the hydrogel films was released. Thus, within 100 min both HA-DTPH films that had been further oxidized with $H_2O_2$ were dissolved and consequently the blue dextran model drug was released completely in the presence of DTT concentration of 10 mM and 50 mM. The release of blue dextran occurring in the absence of DTT (FIG. 5) was negligible.

Furthermore, the enzyme HAse also accelerated the release of model drug (blue dextran) from films. For example, in 48 h the release percentage of blue dextran from air-oxidized HA-DTPH film in PBS at 37° C. at 300 rpm was less than 7%, while under the same conditions in PBS with 100 U/mL Hase, 30% of the blue dextran was released with concomitant partial degradation of the film. After 48 h, approximately 36% of the film had been lost due to enzymatic digestion, as determined gravimetrically.

In situ cell encapsulation. HA-DTPH ($M_w$ 136 kDa, $M_n$=61 kDa, polydispersity index 2.23, SD=58%) was dissolved in DMEM/F-12 medium (GIBCO, Rockville, Md.) to give a 3.0% (w/v) solution under protection, and the solution pH was adjusted to 7.4 by adding 1.0 N NaOH. Then the solution was sterilized under UV light for 25 min under N; protection. Murine fibroblasts (L-929, ATCC, Manassas, Va.) were cultured in a triple flask (Fisher, Springfield, N.J.) until 90% confluence, and then trypsinized and mixed with HA-DTPH solution to a final concentration of $2\times10^6$/mL. Next, 0.5 mL of the HA-DTPH solution was added into each well of a 12-well plate. The cell-loaded plates were incubated (37° C., 5% $CO_2$, 4 h) until a solid hydrogel formed, and then 2 mL of DMEM/

F-12 medium with 10% of newborn calf serum (GIBCO, Rockville, Md.) was added into each well. The plates were transferred to an incubator (37° C., 5% $CO_2$, three days) without a change of medium.

Cell viability and proliferation. The viability of murine L-929 fibroblasts in the hydrogel was determined by a double-staining procedure using fluorescein diactate (F-DA) and propidium iodide (PI) (Kortemme, T.; Creighton, T. E. J. *Mol. Biol.* 1995, 253, 799-812). F-DA (Molecular Probes, Eugene, Oreg.), a non-fluorescent fluorescein derivative, diffuses through the membrane of living cells and is hydrolyzed by intracellular esterase to produce a green fluorescence. PI (Sigma Chemical Co., St. Louis, Mo.), which is excluded by intact cell membranes, but was able to diffuse across a damaged cell membrane, binds to nucleic acids to produce a bright red fluorescence. Briefly, a 5 mg/ml solution of F-DA in acetone was diluted to 20 μg/ml in PBS that contained 0.2 μg/ml PI. After 1 and 3 days culture with encapsulated cells in vitro, the hydrogels were rinsed twice with PBS, immersed in the diluted F-DA/PI solution for 10 min at room temperature and then washed with PBS for 5 min. Then, live and dead cells were observed on a Nikon TS 100 microscope (Nikon, Melville, N.Y.) with Triple (DAPI/FITC/CY3) filter.

After different culture limes, the number of viable cells in each hydrogel was determined using a biochemical assay (Cell-Titer 96 Proliferation Kit, Promega, Madison, Wis.) as previously described (Lutolf. M. P.: Tirelli. N.; Cerritelli. S.; Cavalli, L.; Hubbell, J. A. *Bioconjugate Client.* 2001, 12, 1051-1056). In this method, a tetrazolium salt (MTS) is reduced by the mitochondria of living cells into a colored formazan product whose presence can be detected spectrophotometrically.

The hydrogels in 12-well plates were rinsed twice with PBS buffer, then 900 μl of DMEM/F-12 medium with 5% of newborn calf serum and 180 μL of Cell Titer 96 Proliferation Kit solution were added into each well. After 2 h of incubation with gentle shaking (37° C., 5% $CO_2$), a 125-μL aliquot of each of the solutions was transferred individually into a 96-well plate and read at 550 nm with a OPTI Max microplate reader (Molecular Devices). The absorbance reading was converted into a cell number based on standard curves generated from the assay of known numbers of cells. Data sets were compared using two-tailed, unpaired t-tests. P-values less than 0.05 were considered to be significant.

The rapid gelation of HA-DTPH solution under physiological conditions exhibits potential utility for many biomedical applications, e.g., wound healing, defect filling, prevention of post-surgical adhesions, and cell encapsulation for tissue repair. Murine fibroblasts were entrapped within a crosslinking HA-DTPH hydrogel, and the encapsulated cells were examined after 24 h and 96 h of culture. Viable cells, indicated by green fluorescence upon F-DA staining, were evident after 96 h of culture. Fewer than 5% dead cells were observed as red fluorescence from PI staining (data not shown). Unlike two-dimensional culture in flasks, the fibroblasts in the hydrogel maintained a round shape. In addition, clumps of cells, as well as individual cells, were observed in hydrogel.

Figure 6:
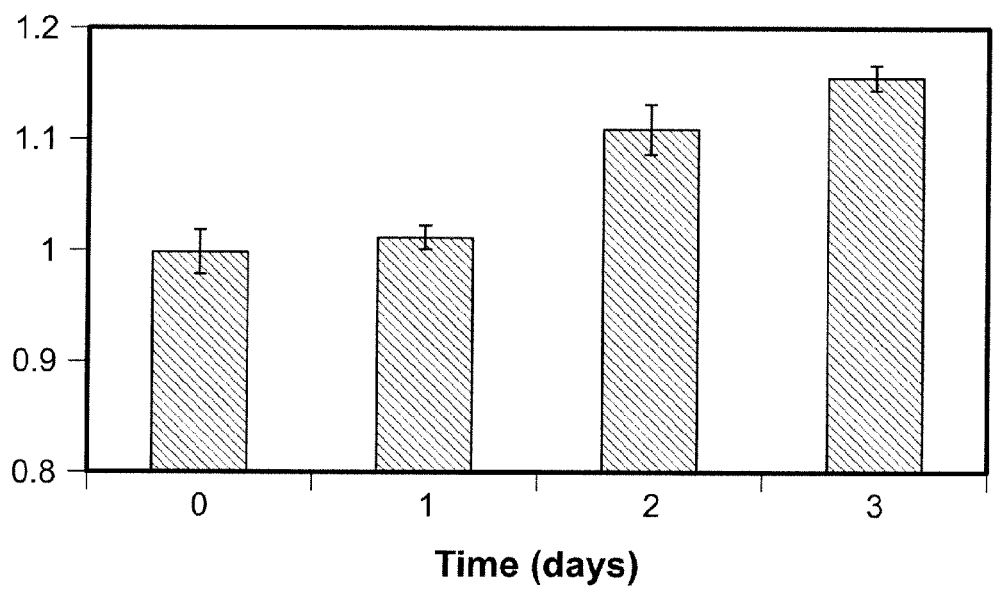
FIG. 6 shows fibroblast proliferation in HA-DTPH hydrogel after in vitro culture of 0, 1, 2, and 3 days.

After in vitro culture for 1,2, and 3 days, the number of viable cells residing in the hydrogel were determined by MTS assay (Cell-Titer 96 Proliferation Kit, Promega, Madison, Wis.). The results indicated that cells proliferated in hydrogel after culture of 2 and 3 days, and the cell number increased ca. 15% at day 3, which was significant with p<0.05 (FIG. 6).

Figure 7:
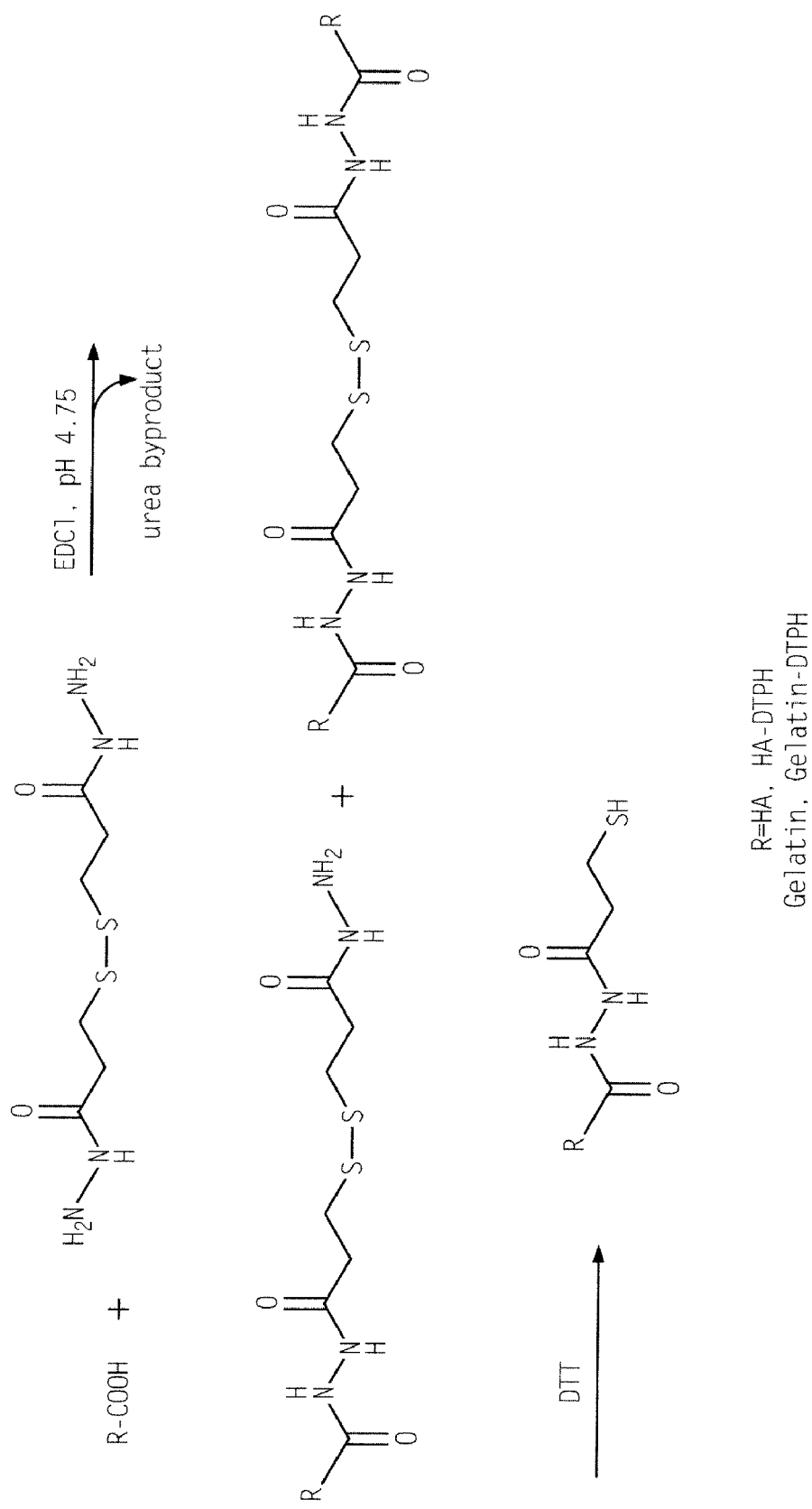
FIG. 7 shows the synthesis of thiolated HA and gelatin.

III. Disulfide Crosslinked Hyaluronan-Gelatin Hydrogels
Synthesis of thiolated HA and gelatin. Low molecular weight (LMW) HA (Mw 246 kDa. Mn 120 kDa, polydispersity index 1.97) was prepared by degradation of high molecular weight HA (1.5 MDa) in dilute HCl (pH ca. 0.5) for 24 h at 37° C. 150 rpm. Thiolated HA and gelatin were synthesized, separately following a general protocol as previously described for HA and chondroitin sulfate (CS) modification (FIG. 7). Thus, 20 g of LMW HA (50 mmol) or 20 g of gelatin was dissolved in 2.0 L of water, and then DTP (11.9 g, 50 mmol for HA; 20 g for gelatin) was added while stirring. The pH of the reaction mixture was adjusted to 4.75 by the addition of 1.0 N HCl. Next EDCI (4.8 g, 25 mmol for HA; 10 g for gelatin) was added in solid form. The pH of each reaction mixture was maintained at 4.75 by the addition of aliquots of 1.0 N HCl. The reaction was stopped by addition of 1.0 N NaOH to increase the pH to 7.0. Then, 100 g of DTT (ca. 650 mmol) was added in solid form and the pH of the solution was further increased to 8.5 by addition of 1.0 N NaOH. After stirring for 24 h at ambient temperature, the pH of the reaction mixture was adjusted to pH 3.5 by the addition of 1.0 N HCl. The acidified solution was transferred to dialysis tubing (MWCO 3,500) and dialyzed exhaustively against ca. 0.3 mM HCl solution (pH 3.5) containing 100 mM NaCl, followed by dialysis against 0.3 mM HCl (without salt) at pH 3.5. The solution was then clarified by centrifugation, and the supernatant was lyophilized. The purity of thiolated HA (HA-DTPH) and thiolated gelatin (gelatin-DTPH) were measured by GPC and $^1$H NMR, and the degree of substitution (SD) and the free thiols on the side chain of HA-DTPH and gelatin-DTPH were determined by $^1$H NMR and by a modified Ellman method (Butterworth P H W. Baum H. and Porter J W. A modification of the Ellman procedure for the estimation of protein sulfhydryl groups. Arch Biochem Biophys 1967, 118: 716-723).

pKa determination. The pKa values for the thiols in HA-DTPH and gelatin-DTPH were determined spectrophotometrically based on the UV absorption of thiolates (Benesch R and Benesch R E. Thiolation of protein. Proc Nat Acad Sci USA 1958; 44:848-853; Lutolf M P, Tirelli N, Cerritelli S, Cavalli L, and Hubbell J A. Systematic modulation of Michael-type reactivity of thiols through the use of charged amino acids. Bioconjugate Chem 2001; 12:1051-1056). Solutions of HA-DTPH and gelatin-DTPH (ca. 5 mg each) were dissolved in 100 ml of 0.001 N HCl containing 0.1 N NaCl (stable ionic strength). UV scans from 190-300 nm were recorded for freshly-prepared solutions.

Turbidimetric titration. The electrostatic interactions of HA-DTPH and gelatin-DTPH were investigated by turbidimetric titration (Shu X Z, Zhu K J, and Song W. Novel pH-sensitive citrate crosslinked chitosan film for drug controlled release. Int J Pharm 2001; 212:19-28; Park J M, Muhoberac B B, Dubin P L, and Xia J. Effects of protein charge heterogeneity in protein-polyelectrolyte complexation. Macromolecules 1992; 25:290-295). A solution of 1.0 mg/ml of either HA-DTPH or LMW HA and 1.0 mg/ml of either gelatin-DTPH or unmodified gelatin was prepared at pH 1.5, and aliquots of a stock NaCl solution were added to adjust the ionic strength. Titrant (0.01-0.2 N NaOH) was delivered using a microburette into the solution with gentle stirring at 30 plus/minus 0.5° C., and the pH was monitored by a digital pH meter with a precision of plus/minus 0.01. Changes in turbidity were monitored at 420 nm with an UV-vis spectrophotometer and reported as (100-T) %, which is linearly proportional to the true turbidity measurements when T>09. The time interval between turbidity measurements was ca. 4 min.

Next, HA-DTPH and gelatin-DTPH were dissolved in 0.02 M PBS (pH 6.5) to give 3.0% (w/v) solutions. The pH of each solution was adjusted to 7.4 by the addition of 1.0 N NaOH, and then the solutions were mixed according to volume ratio of HA-DTPH:gelatin-DTPH of 100:0, 80:20, 60:40, 40:60, 20:80, and 0:100. At different times, the transmittance of the solutions was monitored at 550 nm.

Turbidimetric titration revealed that there were ionic interaction between LMW HA and gelatin, with the formation of a polyelectrolyte complex in the pH range 2.3-5.0, where HA was negatively charged while gelatin (Type B, pI=4.9) was positively charged (data not shown). This phenomenon was evaluated for the thiolated derivatives of HA and gelatin, which still have numerous unmodified carboxylates (1.58 mmol/g for HA-DTPH. 0.65 mmol/g for gelatin-DTPH) and amine groups (0.35 mmol/g for gelatin-DTPH). Turbidometric titration indicated that similar electrostatic interactions occurred in the mixed solutions of HA-DTPH and gelatin-DTPH, but over a broader pH region due to the shift to higher pI for gelatin-DTPH resulting from conversion of >40% of the carboxylates to thiols.

Figure 8:
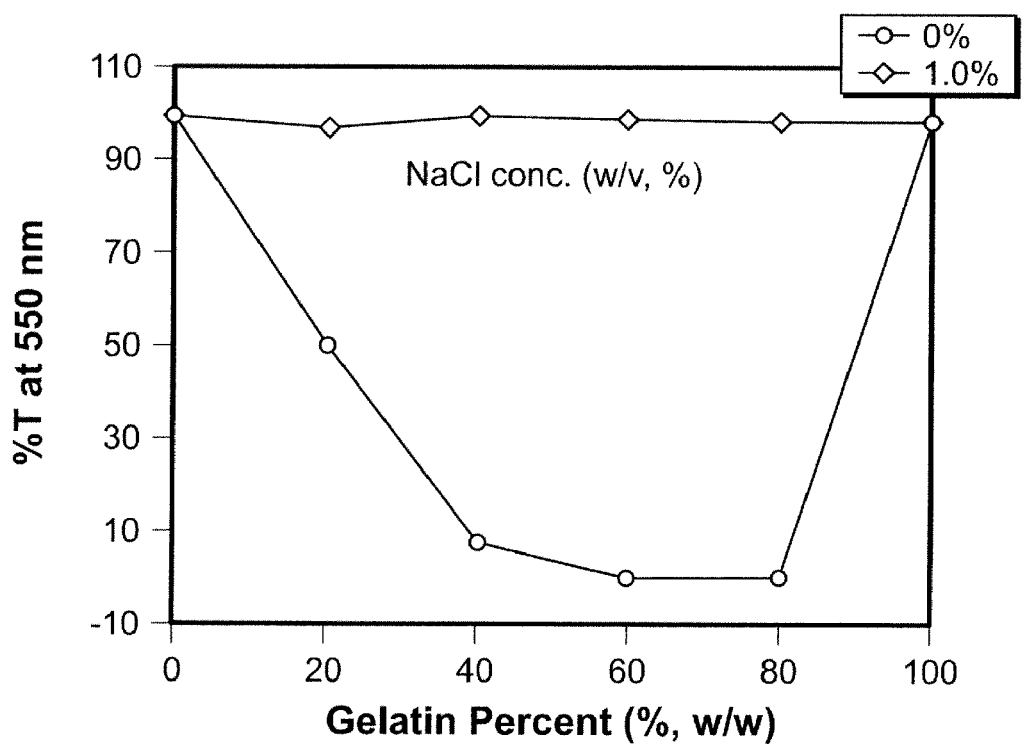
FIG. 8 shows the effect of salt concentration on polyelectrolyte complex formation in mixed HA-gelatin solutions. HA-DTPH and gelatin-DTPH, both 3.0% (w/v), were dissolved in 0.02 M PBS, the pH was adjusted to 7.4 (3.0% w/v), and the solutions were then mixed at different ratios. The absorption was determined at 15 min (open circles, no added salt) and 2 h (open diamonds, 1.0% NaCl) after the preparation of solution in 0.5-cm spectrophotometer cell.

HA-DTPH and gelatin-DTPH were dissolved in 0.02 M PBS, and the pH was adjusted to 7.4 to give clear solutions. When mixed, solutions containing various ratios of HA-DTPH and gelatin-DTPH became translucent, and phase separation occurred immediately due to their electrostatic interactions (FIG. 8). This effect precluded fabrication of homogeneous, transparent hydrogel films from blends of HA-DTPH and gelatin-DTPH. To overcome the formation of polyelectrolyte complexes, the ionic strength of the solutions was increased to mask the electrostatic binding. Indeed, turbidimetric titration revealed that this binding was completely prevented by 3.0% (w/v) NaCl (data not shown). However, this high concentration of salt disturbed the film formation and resulted in an unacceptably brittle film. Therefore; 1.0% (w/v) NaCl was added into HA-DTPH and gelatin-DTPH solution to permit the formation of clear solutions at ratios of HA-DTPH to gelatin-DTPH of 80:20, 60:40, 40:60, and 20:80. No phase separation occurred in 2 h (FIG. 8), although after 24 h, these blended solutions also became opaque, indicating the persistence of electrostatic interactions between these two macromonomers.

Preparation of HA-gelatin hydrogel films crosslinked by disulfide bond. HA-DTPH and gelatin-DTPH (3.0 g each) were separately dissolved in 100 ml of 20 mM PBS buffer (pH 6.5) containing 1.0% (w/v) NaCl, and then the pH of each solution was adjusted to 7.4 by the addition of 1.0 N NaOH. Then, HA-DTPH and gelatin-DTPH solutions were combined in volume ratios of 100:0, 80:20, 60:40, 40:60, 20:80, and 0:100, and thoroughly mixed by gentle vortexing. The mixed solutions (30 ml) were poured into 9-cm petri-dishes and allowed to crosslink in air and to dry at room temperature. After 3 days, air-crosslinked films were obtained and cut into 6, 8, or 1.6-mm diameter discs. The film discs were then further oxidized by immersion in 0.1% $H_2O_2$ for 1 h. The film discs were then rinsed with distilled water and dried at ambient pressure and temperature for one day, and then at 1 mm Hg for one week.

Based on the above results, 1.0% NaCl was used to shield the electrostatic interaction between HA-DTPH and gelatin-DTPH during film formation and crosslinking. The blended hydrogel films were obtained by pouring 30 ml of mixed HA-DTPH—gelatin-DTPH solutions containing 1.0% NaCl (w/v) into 9-cm petri-dishes. Air oxidation and drying at room temperature produced disulfide-crosslinked films. Crosslinking density in these films was increased by further oxidation with 0.1% (w/v) $H_2O_2$; films were then rinsed and dried in vacuo.

Figure 9:
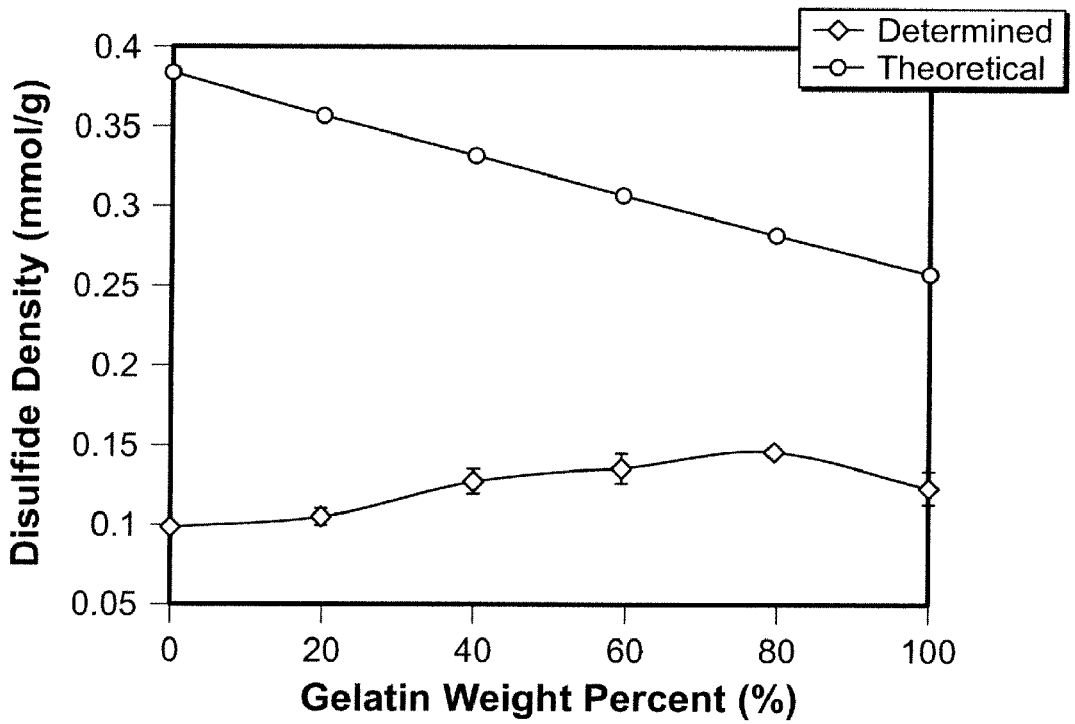
FIG. 9 shows the determination of disulfide density in HA-DTPH gelatin-DTPH hydrogel films. The hydrogel films were prepared with 3.0% (w/v) polymer in 0.02 M PBS (pH 7.4) with 1.0% (w/v) NaCl and then exhaustively hydrolyzed in acid (n=3). NTSB and DTNB reagents were, used as described to obtain total sulfur and thiol contents. The theoretical disulfide density (open circles) was calculated from thiol density (HA-DTPH 0.77 mmol/g, gelatin-DTPH 0.51 mmol/g).

The disulfide content of the HA-gelatin hydrogel films was determined by NTSB after exhaustive acidic hydrolysis (FIG. 9). In agreement with previous results (Nicolas F L and Gagnieu C H. Denatured thiolated collagen II. Crosslinking by oxidation. Biomaterials 1997; 18:815-821), only 25-50% of the thiols were oxidized to disulfides. Since no free thiols were detected by DTNB (Ellman G L. A colorimetric method for determining low concentrations of mercaptans. Arch Biochem Biophys 1958; 74:443-450), this indicated that the other thiols were oxidized by $H_2O_2$ to S-oxidized sulfuric, sulfenic, or sulfonic acids that would not be detected using NTSB and DTNB (Capozzi G and Modena G. Oxidation of thiol, In: Patai S, editor. The Chemistry of the Thiol Group Part II. New York: Wiley, 1974, p. 785-839). However, in contrast with the thiolated HA alone, a high proportion of disulfide-crosslinking was observed in the gelatin-DTPH film, despite the lower acidity of the thiols. Clearly, additional factors, such as the more flexible conformation of the modified gelatin and more mobile, longer thiol-containing side chain could facilitate disulfide formation. For the more rigid linear polysaccharide HA. ca. 25% of the theoretical disulfide bonds were formed in the HA-DTPH hydrogel film; however, over 50% of the theoretical disulfide bonds were formed in gelatin-DTPH hydrogel film. Thus, even though the thiol concentration in HA-DTPH (0.768 mmol/g) is higher than for gelatin-DTPH (0.512 mmol/g), a significantly higher disulfide content was found for the gelatin-DTPH film (0.123 mmol/g) relative to the HA-DTPH film (0.100 mmol) ($p<0.02$). Electrostatic attraction between HA-DTPH and gelatin-DTPH also facilitated disulfide formation; blended films had more disulfide bonds than the HA-DTPH film ($p<0.01$, except for HA-DTPH:gelatin-DTPH of 80:20). The disulfide density of the films with ratio of HA-DTPH:gelatin-DTPH of 40:60 (0.136 mmol/g) and 20:80 (0.145 mmol/g) even higher than that in gelatin-DTPH film (0.123 mmol/g) ($p<0.01$).

Swelling determination. Film discs with diameter of 6 mm were weighed (Wd), immersed in glass vials containing 10 ml PBS (pH 7.4), and placed in an incubator at 37° C. 300 rpm. At predetermined time intervals, the wet films were weighed ($W_t$) immediately after the removal of the surface water by blotting briefly between two pieces of filter paper. The swelling ratio (R) was defined as Wt/Wd.

Figure 10:
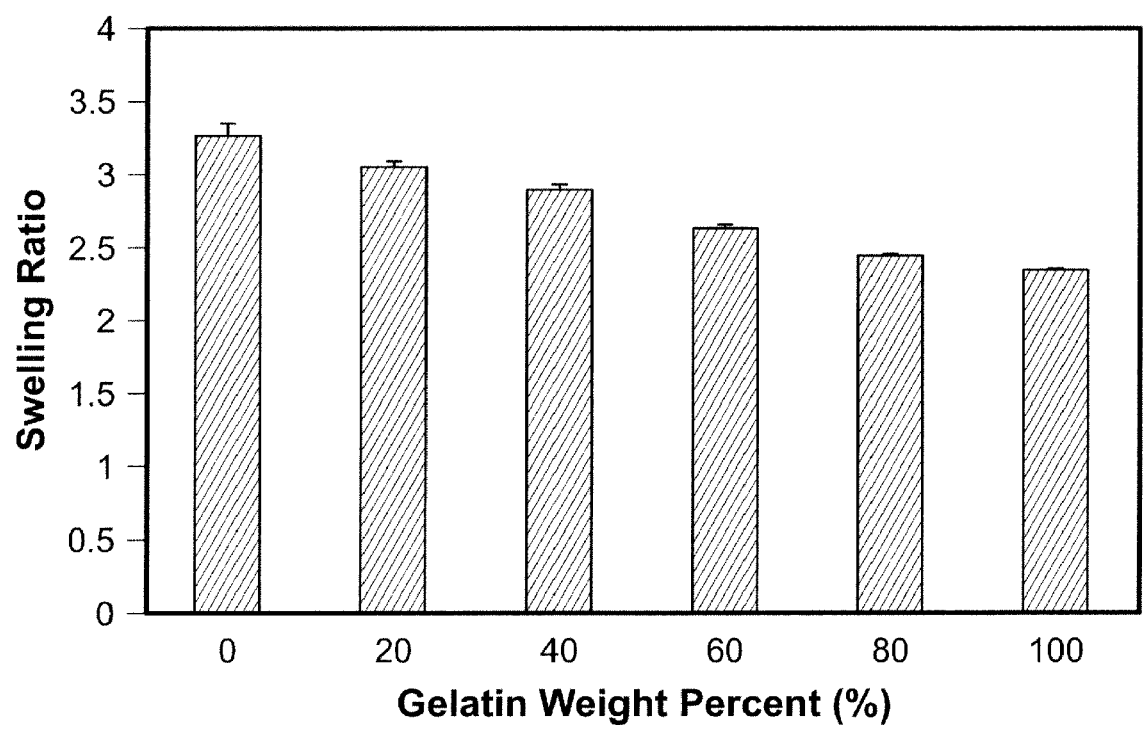
FIG. 10 shows the equilibrium swelling ratio of HA-gelatin films. The ratio was measured in PBS at 37° C., 300 rpm (n=3). The hydrogel films were prepared with 3.0% (w/v) polymer in 0.02 M PBS (pH 7.4) with 1.0% (w/y) NaCl.

The equilibrium swelling ratio of the hydrogel films in PBS is shown in FIG. 10. With increasing percentages of gelatin-DTPH, the swelling ratio decreased from 3.27 to 2.33. This ratio is determined only by the crosslinking density, but is also related to the bulk properties of the films.

One of the disadvantages for many HA and gelatin-based biomaterials is rapid degradation in vivo. Therefore, the optimization of the mechanical properties and rate of degradation by co-crosslinking the HA and gelatin was sought. This strategy proved effective. Preliminary evidence showed that disulfide-crosslinked HA-DTPH hydrogels would degrade slowly, both in vitro and in vivo, and that the degradation rate could be controlled by altering the disulfide-crosslinking density. Thus, approximately 30% weight loss of HA-DTPH hydrogel film was found after 42 days of implantation in vivo in mice (data not shown). With a very high concentration of HAse (300 U/ml) in vitro, only ca. 8% weight loss of HA-DTPH hydrogel film was observed in 48 h (data not shown). On the other hand with the same concentration of enzyme (collagenase 300 U/ml), in 48 h, ca. 62% of gelatin-DTPH hydrogel film was digested (data not shown). The rapid degradation of gelatin-based biomaterials could limit usage in many biomedical applications (Nicolas F L and Gagnieu C H. Denatured thiolated collagen II. Crosslinking by oxidation. Biomaterials 1997; 18:815-821).

Disulfide content determination. Film discs with diameter of 6 mm were degraded by acid hydrolysis (0.1 N HCl, 37° C.

150 rpm for 10 days). The total sulfur content (S—S+SH) was measured using 2-nitro-5-thiosulfohenzoate (NTSB) (Thannhauser T W, Konishi Y, and Scheraga H A. Analysis for disulfide bonds in peptides and proteins. Methods In Enzymology 1987; 143:115-119), and the free thiol content was measured by the Ellman method (Ellman G L. A colorimetric method for determining low concentrations of mercaptans. Arch Biochem Biophys 1958, 74:443-450). Disulfide content, equivalent to crosslinking density, was calculated as the difference between total sulfur content and free thiol content. In vitro degradation of HA-gelatin hydrogel film. The degradation of disulfide-crosslinked HA-gelatin films was performed using collagenase and HAse. Film discs with diameter of 8 mm were incubated in a glass bottle containing 3 ml medium with 300 U/ml collagenase or HAse, and placed in an incubator at 37° C., 150 rpm. The medium was changed every two days. At predetermined intervals, the films were washed five times with distilled water and dried under vacuum. The buffer used for collagenase was 100 mM Tris-HCl buffer (pH 7.4) containing 5 mM $CaCl_2$ and 0.05 mg/ml sodium azide (Choi Y S, Hong S R, Lee Y M, Song K W, Park M H, and Nam Y S. Studies on gelatin-containing artificial skin:II, preparation and characterization of crosslinked gelatin-hyaluronate sponge. J Biomed Mater Res (Appl Biomater) 1999; 48:631-639). HAse digestions were performed in 30 mM citric acid, 150 mM $Na_2HPO_4$, 150 mM NaCl (pH 6.3) (Bulpitt P and Aeschlimann D. New strategy for chemical modification of hyaluronic acid: Preparation of functionalized derivatives and their use in the formation of novel biocompatible hydrogels. J Biomed Mater Res 1999; 47:152-169). For simultaneous digestion with collagenase and HAse, the buffer used was 100 mM. Tris-HCl buffer (pH 7.4) containing 5 mM $CaCl_2$, 150 mM NaCl, and 0.05 mg/ml sodium azide. The weight loss fraction was determined as (t−Wt/W0), where Wt is the weight of dried film at time t, and W0 is the original weight of dried film.

Figure 11A:
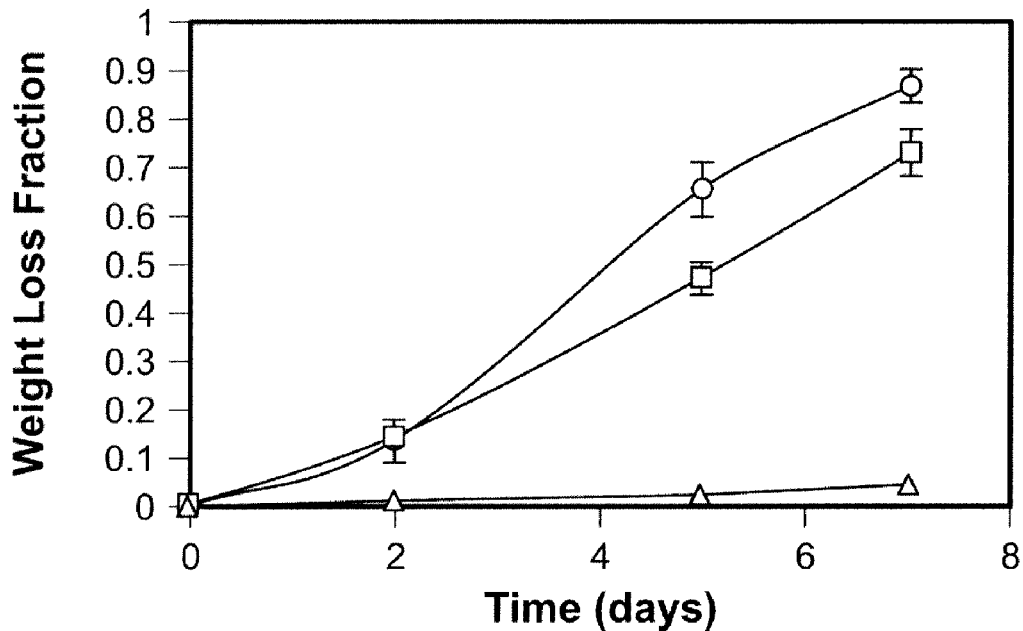
FIG. 11 shows the enzymatic degradation of mixed HA-gelatin films. The weight loss of HA-gelatin hydrogel films in 300 U/ml enzyme solutions (HAse, open triangles; collagenase, open squares; open circles, HAse plus collagenase) at 37° C., 150 rpm (n=3). Panel A: HA-gelatin, 20:80. Panel B: HA-gelatin, 40:60. The hydrogel films were prepared with 3.0% (w/v) polymer in 0.02 M PBS (pH 7.4) with 1.0% (w/v) NaCl.
Figure 11B:
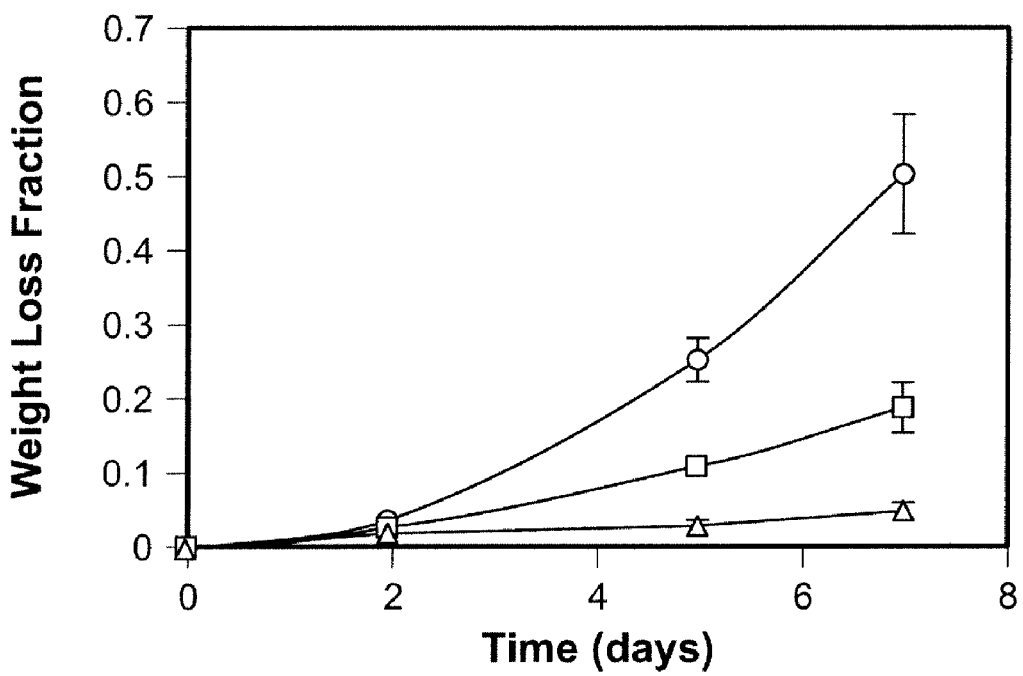

The blending of HA-DTPH with the gelatin-DTPH in films significantly slowed digestion by collagenase. Thus, with 300 U/ml collagenase, HA-gelatin films (80% or 60% gelatin), the weight loss in two days was only 15% and 2%, respectively (FIG. 11a and 11b). These films were also more resistant to the digestion by HAse than HA-DTPH films, with less than 5% weight loss in 300 U/ml HAse for two days (FIGS. 11a and b). When both HAse and collagenase were present, degradation of HA-gelatin film was accelerated. For instance, the weight loss after 7 days for an HA-gelatin (60% gelatin) film was 18% with 300 U/ml collagenase and 5% with HAse; with both enzymes combined, weight loss was as high as 50% (FIG. 11b).

Cell growth on the surface of hydrogel films. The growth of murine Balb/c 3T3 fibroblasts (ATCC) on disulfide-crosslinked HA/gelatin hydrogel film was evaluated. The cells were cultivated in Modified Eagle Medium (DMEM, GIBCO) supplemented with 10% newborn calf serum (GIBCO), Pen-Strep, L-glutamine and sodium bicarbonate. The fibroblasts were trypsinized in the logarithmic growth state and evenly seeded onto the hydrogel surfaces at ca. 5,000 or at 25,000 cells/$cm^2$.

Cell viability. An in situ fluorescence viability assay with fluorescein diacetate (F-DA, Molecular Probes, Eugene, Oreg.) was performed to assess the cell viability on the hydrogel surface. A 5 mg/ml solution of F-DA in acetone was prepared and diluted to 0.02 mg/ml in PBS. After 24 h of in-vitro culture in an incubator with 5% $CO_2$ at 37° C. (25,000 cells/$cm^2$ were initially seeded), the hydrogel films were rinsed with PBS twice to remove the unattached cells, and then immersed in the diluted F-DA solution for 3 min at room temperature and then washed in PBS for 5 min. Fluorescence in the live cells was observed using a Nikon TS 100 microscope (Nikon, Melville, N.Y.) with DAPI filter, and photomicrographs of the cell attachment and spreading were recorded.

Figure 12:
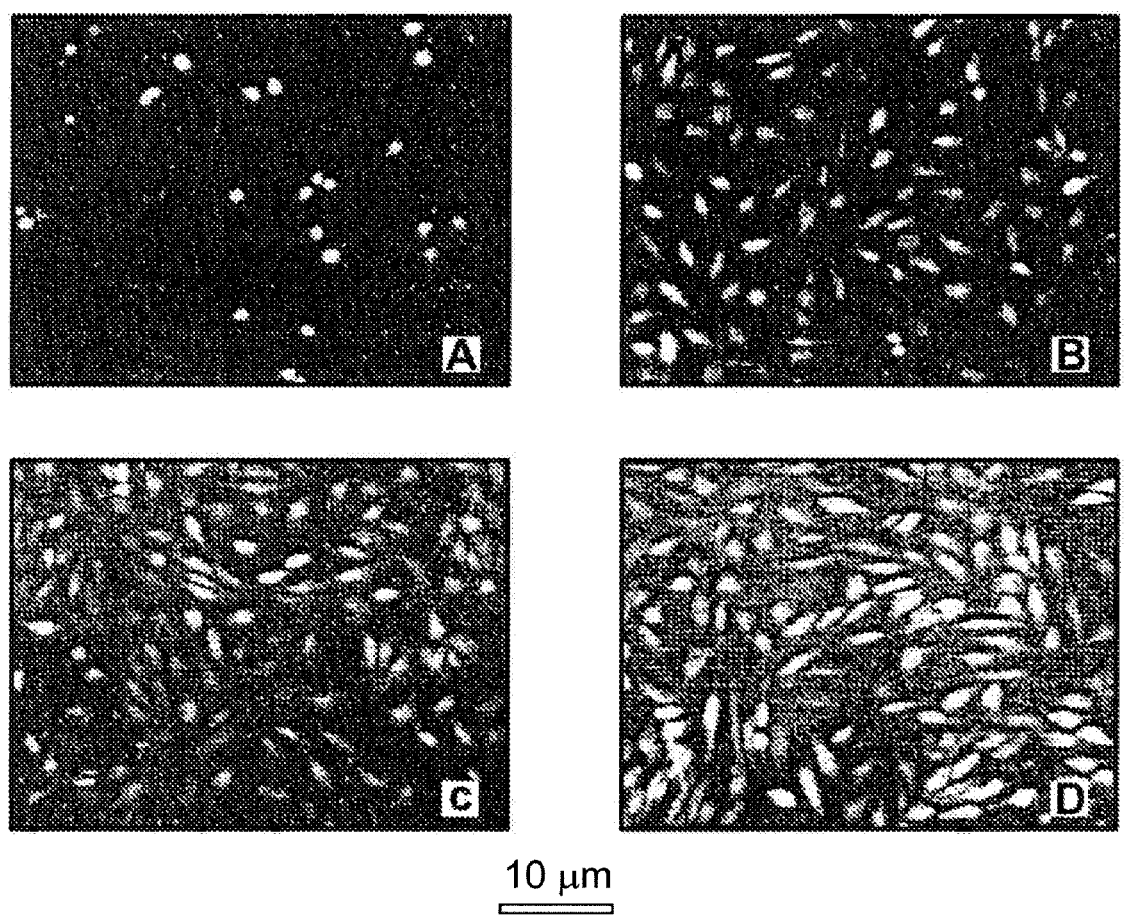
FIG. 12 shows the cell attachment and spreading of fibroblasts of HA-gelatin films. Fluorescent microscopic images of adherent and spread Balb/c 3T3 fibroblast on the surface of HA-gelatin hydrogel films after 24 h of in vitro culture. The cells were initially seeded at 25,000 cells/cm2 and were stained with F-DA. Panel a: 100% HA film: Panel b: HA-gelatin, 80:20; Panel c: HA-gelatin, 40:60 film; and Panel d: 100% gelatin-DTPH film. Original magnification: Panels a, b, c, and d at ×100.

Balb/c 3T3 fibroblasts; were seeded on the surface of the HA-gelatin films of different compositions and cultured in vitro for 24 h. and then the live cells were stained with F-DA to give green fluorescence. A morphological study revealed that only a very small number of cells with spherical shape were attached to the surface of HA-DTPH hydrogel film that lacked a protein component (FIG. 12a). Addition of gelatin-DTPH significantly improved the cell attachment (FIG. 12b-12d), even at 20% (w/v). At gelatin concentrations of 40% and higher, the majority of cells adopted a spindle-shaped morphology and spread uniformly on the hydrogel surface (FIG. 12b-12d).

Cell proliferation. The surfaces of 2-$cm^2$ film discs were seeded with 5,000 cells/$cm^2$. After 24 and 72 h of incubation without changing the cell culture media, the cell numbers were evaluated by the metabolic reduction of MTT to a colored formazan dye by viable cells. Thus, sterile aliquots of a 5 mg/ml stock solution of MTT in PBS were added at a ratio of 60 l per 500 l of medium to each film disc (2 $cm^2$), and incubated for 4 h at 37° C. Then, the medium was discarded, and each film disc was incubated in 1.0 ml DMSO to lyse the cells and dissolve the dyes. Cell-free film discs were used as blanks. Next, 200 µl of each DMSO solution was transferred into a 96-well plate and the absorption was recorded at 550 nm on an OPTI Max Microplate Reader.

Figure 13:
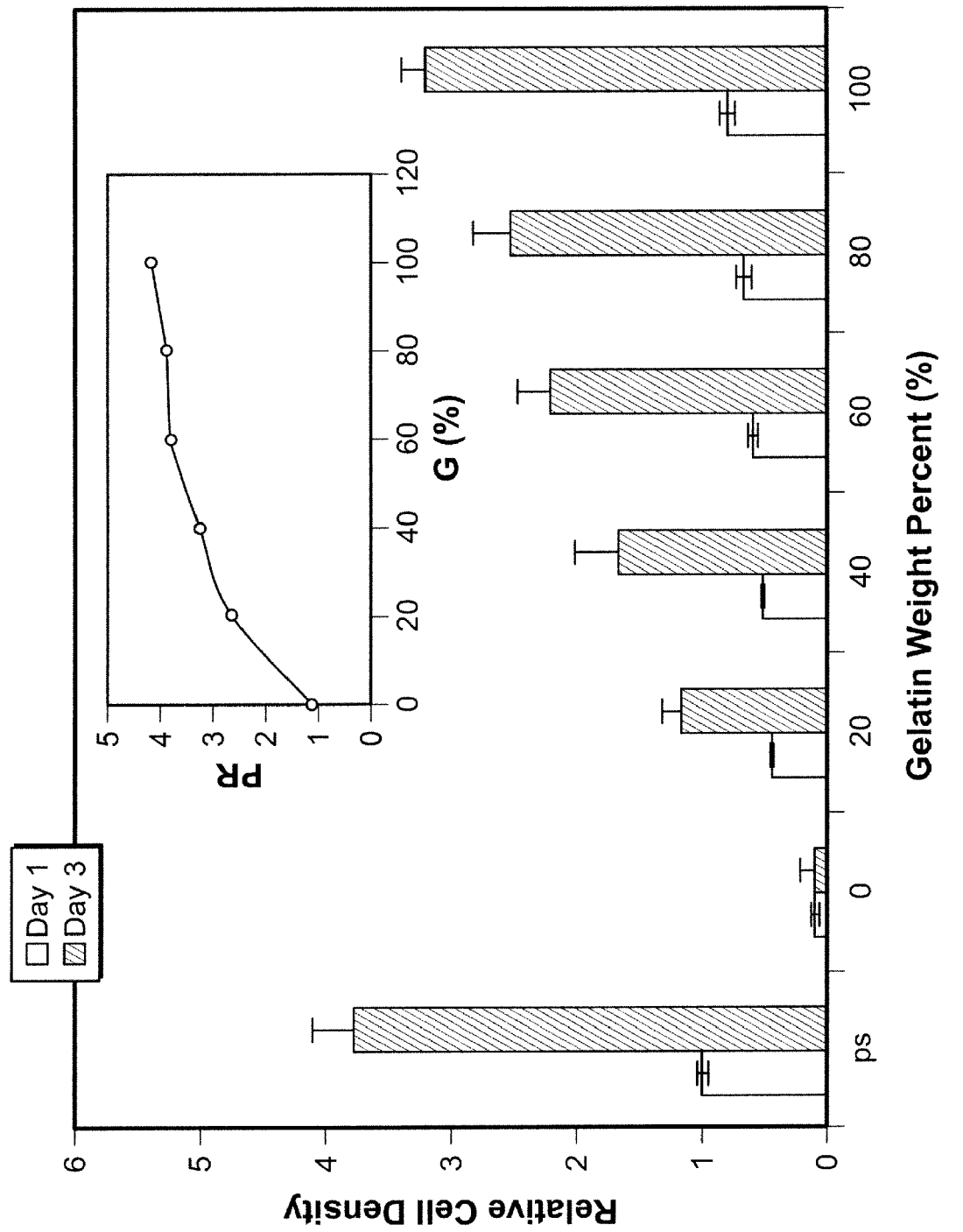
FIG. 13 shows the proliferation of Balb/c 3T3 fibroblast on the surface of HA-gelatin hydrogel film. The cells were initially seeded at 5,000 cells/$cm^2$ and the cell number was determined by MTT assay after one day and three days culture in vitro (n=5). Tissue culture polystyrene (PS) was used as control, and the relative cell density on tissue culture polystyrene after one day of in vitro culture was defined as 1:0: The inset shows the proliferation ratio (PR) as a function of percent gelatin (% G) in the hydrogel.

Using cell culture-grade polystyrene as control, the proliferation of Balb/c 3T3 fibroblasts on the hydrogel surface was evaluated. The cells were initially seeded at a density of 5,000 cells/$cm^2$, and cultured in vitro for one day and three days, and then the cell number was determined by MTT assay. The cell number in cell culture polystyrene after one day culture was defined as 1.0 and the relative cell density was calculated. FIG. 13 shows that while cells on the HA-DTPH hydrogel surface failed to proliferate, increasing percentages of gelatin in the films result in accelerated cell proliferation. After three days culture in vitro, the cell number on the hydrogel surface with a gelatin percentage greater than 60% (w/v), was more than 50% of the polystyrene control, while the cell number on gelatin-DTPH hydrogel surface was 85% of the control.

Statistical analysis. Data sets were compared using two-tailed, unpaired t-tests; values of $p<0.05$ were considered to be significant.

IV. Preparation of Hydrogels Via Michael Addition

Synthesis of thiolated HA and thiolated gelatin. Low molecular weight (LMW) HA ($M_w$ 246 kDa, $M_n$ 120 kDa, polydispersity index 1.97) was used after the degradation of high molecular weight HA (1.5 MDa) in dilute HCl (pH 0.5) for 24 h at 37° C. 150 rpm. Thiolated HA (HA-DTPH and HA-DTBH) and thiolated gelatin (gelatin-DTPH and gelatin-DTBH) were synthesized as described above. The degree of substitution (SD), i.e., the fraction of carboxylates modified, was calculated from the integrated $^1$H-NMR spectrum.

Synthesis of Homobifunctional PEG Electrophiles

PEG-diacrylate (PEGDA), PEG-dimethacrylate (PEGDM), PEG-diacrylamide (PEGDAA) and PEG-dimethacrylamide (PEGDMA) were synthesized from PEG (Mw 3400 KDa, Aldrich) or PEG-diamine (Mw 3400, Shearwater Polymers) as described with minor modifications. Briefly: PEG (or PEG-diamine) molecular weight 3400 (10 g, 5.88 mmol of functional group) was azeotropically distilled with 400 ml of toluene under argon, removing ca. 100 ml of toluene. The anhydrous solution was cooled at room temperature under argon and then copied in an ice bath. Anhydrous dichloromethane (Aldrich) (ca. 50 ml) was added until the solution become clear. Triethylamine (1.23 ml, 8.82 mmol, Aldrich) was added dropwise with stirring, followed by the dropwise addition of 0.72 ml of acryloyl chloride (8.82 mmol, Aldrich) or 0.85 ml of methacryloyl chloride (8.82 mmol, Aldrich). The reaction was stirred in the dark, overnight under argon. The solutions were then filtered under vacuum until clear, and the product was precipitated in diethyl ether, collected by filtration and dried under vacuum. Next, 10 g of the product were dissolved in 10 ml of distilled water, adding 5 g of NaCl (the pH was adjusted to 6). The derivatives were then extracted 3 times with dichloromethane and precipitated in diethyl ether, and collected by filtration and dried under vacuum. PEG diacrylate: yield 75%. $^1$H-NMR ($DCCl_3$): 3.6 ppm (303.5 H, PEG), 4.3 ppm (t, 4H, —$CH_2$—$CH_2$—O—CO—CH=$CH_2$), 5.8 ppm (dd, 2H, $CH_2$=CH—COO), 6.1 ppm, 6.4 ppm (dd, 4H, $CH_2$=CH—COO—). Degree of substitution 95%. PEG dimethacrylate: yield 60%. $^1$H-NMR ($DCCl_3$): 2.3 ppm (s, 6 H, $CH_2$=C($CH_3$)=COO—), 3.6 ppm (303.5H, PEG). 4.3 ppm (t, 4H, —$CH_2$—$CH_2$—O—CO—C($CH_3$)=$CH_2$), 5.8 ppm, 6.1 ppm (d, 4H, $CH_2$=C($CH_3$)—COO—). Degree of substitution 91%. PEG diacrylamide: yield 75%. $^1$H-NMR ($DCCl_3$): 3.6 ppm (304.4H, PEG), 5.6 ppm (dd, 2H, $CH_2$=CH—CON—), 6.1 ppm and 6.3 ppm (dd, 4 H, $CH_2$=CH—COO—). Degree of substitution 100%. PEG dimethacrylamide: yield 71%. $^1$H-NMR ($DCCl_3$): 2 ppm (s. 6 H, $CH_2$=C($CH_3$)—CON—), 3.6 ppm (304.4H, PEG), 5.3 ppm, 5.8 ppm (d, 4H, $CH_2$=C($CH_3$)—CON—). Degree of substitution 100%.

Figure 15:
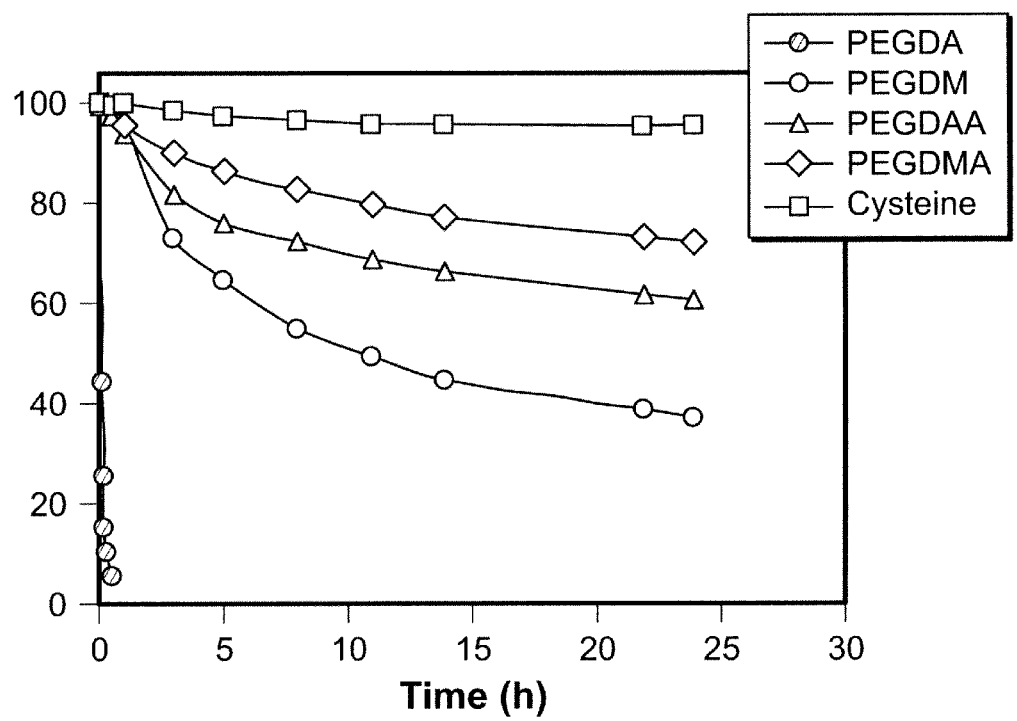
FIG. 15 shows the conjugate addition between PEGDA, PEGDM, PEGDAA, PEGDMA and cysteine.

Conjugate addition. The relative reactivity of conjugate addition of $\alpha,\beta$-unsaturated esters and amides of poly(ethylene glycol) to thiols was first evaluated using cysteine as a model. The conjugate addition of cysteine to each of the four electrophilic species is shown in FIG. 15. Cysteine (2.5 mg) and PEG-diacrylate (PEGDA), PEG-dimethacrylate (PEDMA), PEG-diacrylamide (PEGDAA) or PEG-dimethacrylamide (PEGDMA) were dissolved in 5 ml of 0.1 N PBS, pH 7.4 (ratio of double bond/SH 2/1). Then the consuming of thiols was monitored by DTNB (Ellman) or NTSB (Thannhauser). Next, the conjugate addition of thiols with different reactivity (i.e., different pKa values) was evaluated using the MW 375 monofunctional PEG-acrylate as a model compound. HA-DTPH or HA-DTBH (10 mg) was dissolved in 5 ml of 0.1 N PBS, pH 7.4, and then PEG-acrylate was added (double bond: thiol=10:1). The consumption of free thiols was monitored using DTNB (Ellman, Thannhauser).

Figure 14:
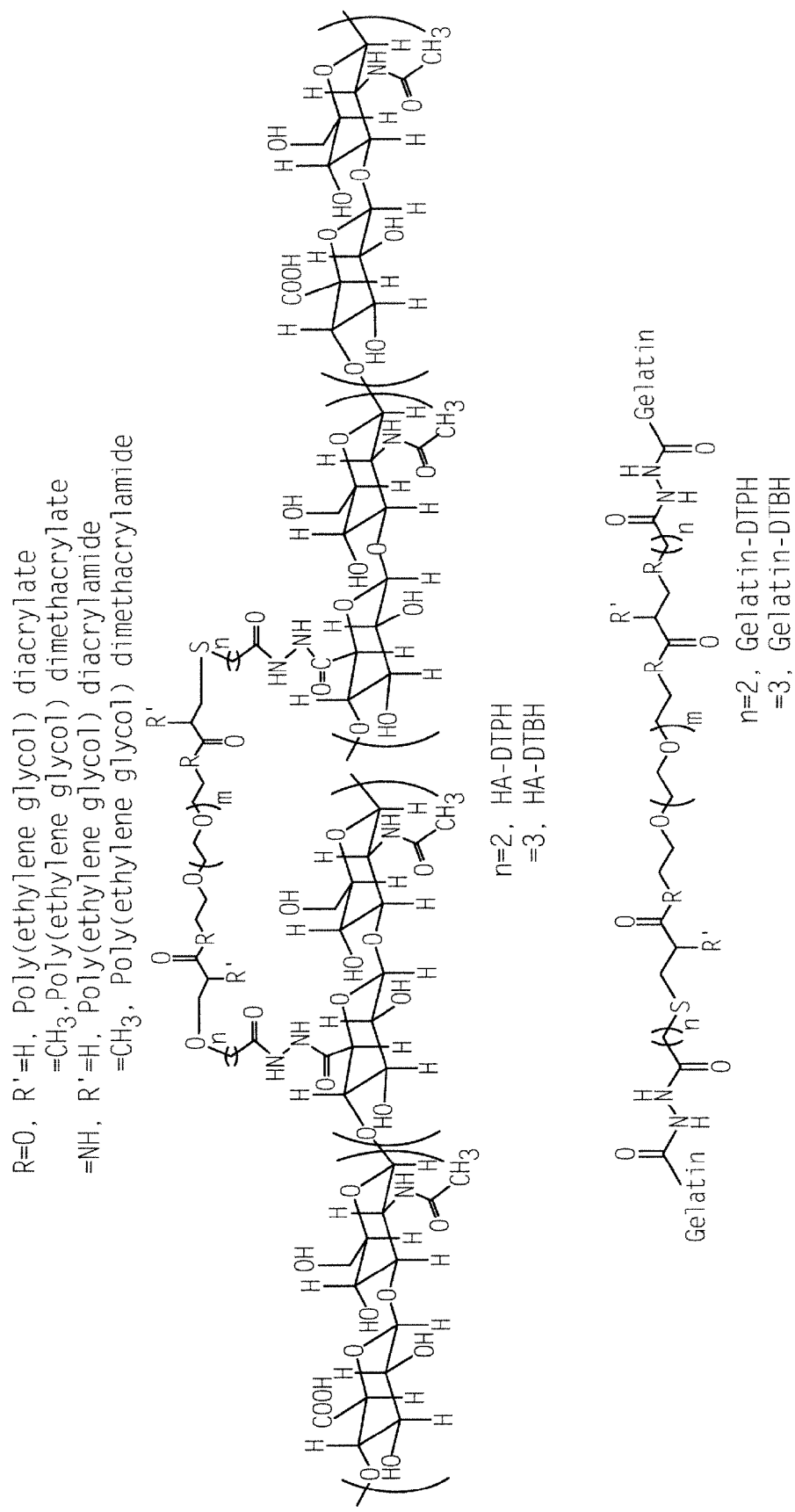
FIG. 14 shows structures of α,β-unsaturated esters and amides of poly(ethylene glycol) crosslinked with thiolated HA and thiolated gelatin.
Figure 16:
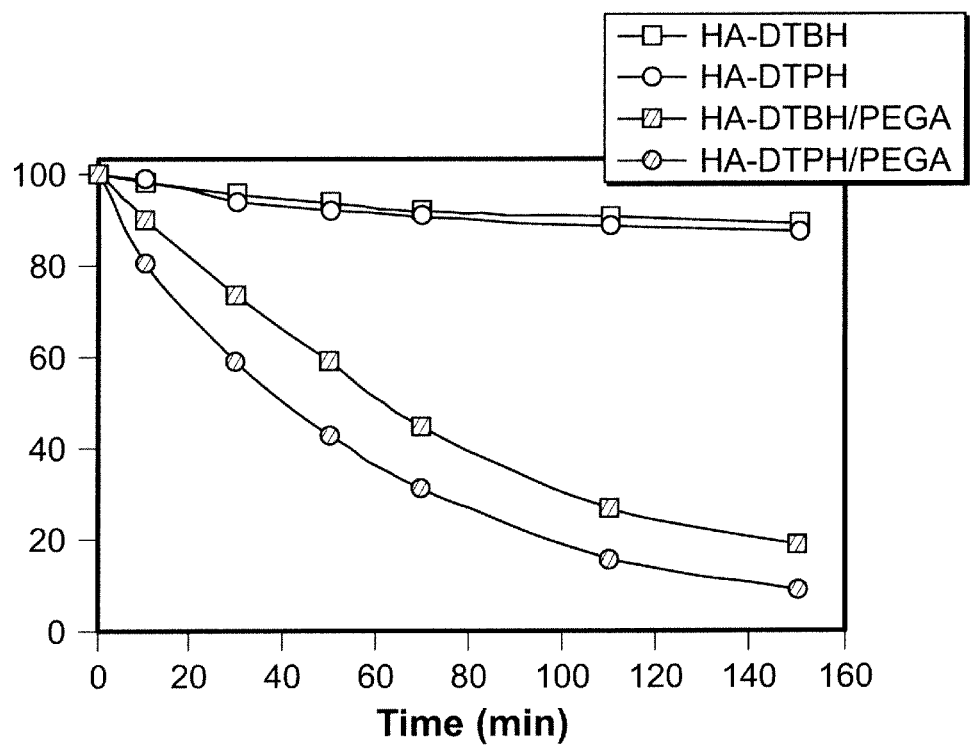
FIG. 16 shows the conjugate addition of HA-DTPH, HA-DTBH and PEG-acrylate.

Hydrogel preparation. Thiolated HA and/or thiolated gelatin were dissolved in cell culture medium to give 1.25% (w/v) solution, and the pH was adjusted to 7.4. Two $\alpha,\beta$-unsaturated ester and two $\alpha,\beta$-unsaturated amide derivatives of PEG were synthesized and used to crosslink thiolated HA and gelatin (FIG. 14). Each of the four PEG derivatives (PEGDA, PEGDM, PEGDAA, and PEGDMA) was dissolved in PBS to give 4.5% (w/v; stock solution. Then, 1 ml of the stock reactive PEG solution was added in one portion to 4 ml of the thiolated HA, thiolated gelatin solution, or a blend of the two components, and mixed for 30 seconds. Gel formation occurred within 10 min (PEGDA) to several days (PEGDMA), with the time dependent on the structure of the reactive PEG derivative. The conjugate addition of HA-DTPH to a low molecular weight PEG-monoacrylate was a slightly faster than between with the less reactive HA-DTBH (FIG. 16).

Determination of Crosslinking Efficiency

Crosslinking was evaluated in detail for both thiolated HA deriviatives with PEGDA as the homobifunctional crosslinker. After 1 h, a mixture of each thiolated HA (HA-DTPH and HA-DTBH) and PEGDA had completely gelled. The resulting hydrogels were then incubated in medium (pH 4.5 or 1.0) to quench the crosslinking addition, and the crosslinking efficiency was determined by measuring the remaining free PEG electrophile and the remaining free thiols and performing the calculations indicated below.

First, the quantity of free PEGDA in the hydrogel was determined by GPC with monitoring of the eluent at 233 nm; Briefly, the hydrogel (0.1 ml) was ground into small particles and suspended in 2 ml of 0.1 M acetate buffer (pH 4.5). After stirring for 4 h at room temperature, the amount of residual PEG derivatives was determined using a standard calibration curve. No free thiolated HA was detected by GPC at 210 nm.

Next, the free thiols in the hydrogel were determined using either the DTNB or NTSB assay. Briefly, a 0.05-ml fragment of hydrogel was suspended in 0.5 ml of 0.1 N HCl solution. After 48 h at room temperature with agitation at 150 rpm, the hydrogel had dissociated. Next, 2.0 ml of either NTSB or DTNB reagent was added to each gel, and the number of free thiols in the hydrogel was determined spectrophotometrically at 412 nm. Thiolated HA solutions alone were used as reference materials, and the disulfide formation during hydrogel preparation (1 h) under nitrogen protection was negligible.

The extent of effective crosslinking (i.e. double-end anchorage), unreacted pendent double bond groups during the coupling reaction (i.e., single-end anchorage) was calculated from the total PEGDA used (A), the unreacted PEGDA (B), the total thiols (C) and the free thiols in hydrogel (D). Single-end anchorage equals to the theoretical consumed thiols (2(A-B)) minus the actually consumed thiols (C-D). Subtraction of single-end anchorage from the experimentally measured consumed thiols (C-D) reveals the extent of double-end anchorage. Table 3 shows the crosslinking efficiencies, and Table 4 shows the crosslinking densities, equilibrium swelling ratios, and gelation times for the gels obtained by the reaction of HA-DTPH and HA-DTBH.

TABLE 3

Crosslinking efficiency of PEGDA to HA-DTPH and HA-DTBH

| | Molar ratio of thiols to double bonds | Crosslinking efficiency (%) of PEGDA | | |
|---|---|---|---|---|
| | | Double-end anchorage | Single-end anchorage | Unreacted |
| HA-DTPH: PEGDA | 1:1 | 76.2 | 9.7 | 14.1 |
| | 2:1 | 93.7 | 6.3 | 0 |
| | 3:1 | 100.0 | 0 | 0 |
| HA-DTBH: PEGDA | 1:1 | 48.3 | 19.3 | 32.4 |
| | 2:1 | 60.0 | 12.7 | 27.3 |
| | 3:1 | 73.8 | 8.3 | 17.9 |

TABLE 4

Crosslinking density, equilibrium swelling ratio (Q) and gelation time for gels prepared using PEGDA (Mw 3400) with HA-DTPH and HA-DTBH

| | Molar ratio of thiols to double bonds | Crosslinking density (mmol/ml)* | Swelling ratio (Q) | Gelation time (min) |
|---|---|---|---|---|
| HA-DTPH:PEGDA | 1:1 | 8.1 | 39.41 ± 0.34 | 5 |
| | 2:1 | 5.0 | 46.15 ± 0.38 | 9 |
| | 3:1 | 3.5 | 61.06 ± 0.89 | 19 |

TABLE 4-continued

Crosslinking density, equilibrium swelling ratio (Q) and gelation time for gels prepared using PEGDA (Mw 3400) with HA-DTPH and HA-DTBH

|   | Molar ratio of thiols to double bonds | Crosslinking density (mmol/ml)* | Swelling ratio (Q) | Gelation time (min) |
|---|---|---|---|---|
| HA-DTBH:PEGDA | 1:1 | 5.1 | 58.14 ± 0.94 | 11 |
|  | 2:1 | 3.2 | 69.33 ± 2.94 | 19 |
|  | 3:1 | 2.6 | 84.62 ± 1.98 | 31 |

*Crosslinking density was defined as the number of effective crosslinking sites in 1 ml of hydrogel.

Swelling Determination

Hydrogels were placed in PBS buffer at 37° C. for 48 h and the medium was changed frequently. The swelling ratio (Q) was defined as a ratio of the weight of swollen gel to the weight of dry gel. The weight of the dry gels was determined by washing the hydrogel with distilled water 5 times and then drying the gel under vacuum (1 mm Hg) at room temperature for 3 days.

Figure 17:
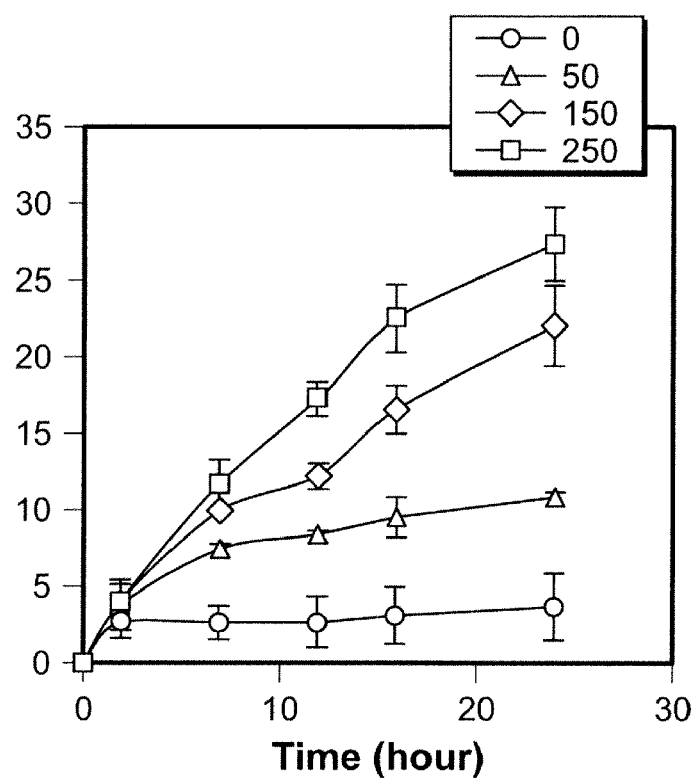
FIG. 17 shows the digestion of HA-DTPH-PEGDA with HAse.

The degradation of hydrogel. Hydrogel discs (0.5 ml) were prepared from HA-DTPH and PEGDA as described above by crosslinking in the bottom of a 6-mm diameter vial. Hyaluronidase (HAse) solutions (0, 50, 150 and 250 U/ml) were prepared in 30 mM citric acid, 150 mM $Na_2HPO_4$, 150 mM NaCl (pH 6.3); 5 ml of enzyme solution was added to each vial containing the hydrogel, and vials were incubated at 37° C. with orbital agitation at 150 rpm. The degradation of the gel was determined from the release of glucuronic acid into the supernatant as measured by the carbazole assay (Bitter T and Muir H. A modified uronic acid carbazole reaction. Anal. Biochem. 1962; 4:330-334). FIG. 17 shows the digestion of a HA-DTPH/-PEGDA hydrogel by HAse, showing that at lower concentrations of enzyme the gel remains largely intact for several days in vitro.

In Vitro Cell Culture

Preparation of composites of T31 fibroblasts and HA-DTPH/PEG-diacrylate hydrogel. HA-DTPH solution (1.25% (w/v)) was prepared by dissolving lyophilized HA-DTPH (SD=42%) in complete DMEM/F-12 medium, adjusted pH=7.4-7.5 with 1.0N NaOH, and sterilized by filtration with 0.45 μm syringe filter. Next, a 4.5% PEGDA solution was prepared by dissolving PEGDA in PBS buffer and sterilized by filtration with 0:45 μm syringe filter. Then, T31 human pharyngeal fibroblasts that had been cultured in triple flasks (175 $cm^2$) and trypsinized with 0.25% sterile trypsin in 0.05% EDTA, were suspended in freshly prepared HA-DTPH solution at concentration of $10^6$ cells/ml. To four volumes of the cell suspension was added one volume of the PEGDA stock solution, and the mixture was vortexed gently. Next. 300 μl of the mixture of the fibroblast-seeded HA-DTPH-PEGDA mixture was poured into each well of 12-well plate and gelation was allowed to occur (1 h). Finally, complete DMEM/F-12 medium was added into each well and the plate was incubated for at 37° C. in a 5% $CO_2$ incubator. The medium was changed every three days without damaging the gel. The seeded hydrogels were used to determine in vitro cell viability and proliferation and for transplantation in vivo into nude mice for fibrous tissue generation.

Figure 18:
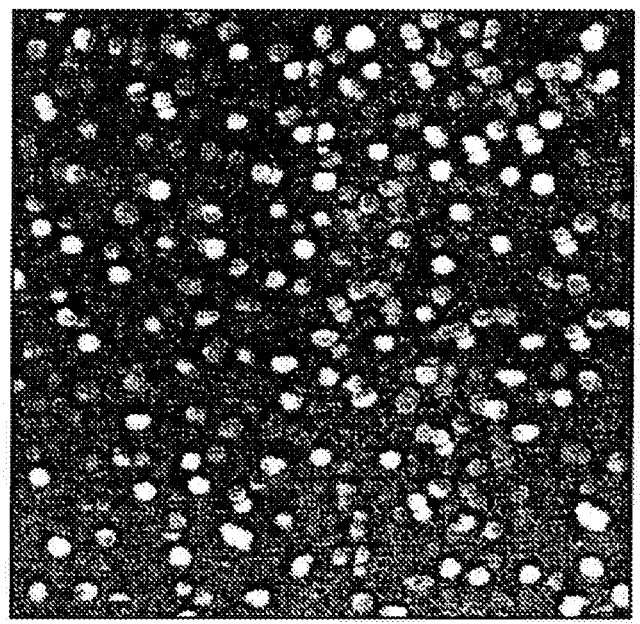
FIG. 18 shows the viability of T31 fibroblasts after 28 days in vitro culture in HA-DTPH-PEGDA hydrogel, confocal microscope, magnification=×200.

Cell viability and proliferation. Viability was determined with live-dead staining methods at day 6 and day 28 of culture in vitro. At each time, four fibroblast-seeded HA-DTPH-PEGDA hydrogels were rinsed twice with PBS buffer, stained for 3 min with fluorescein diacetate (F-DA, 0.02 mg/ml) and propidium iodide (PI, 0.2 μg/ml) at room temperature, rinsed twice with PBS buffer, stored on ice, and observed using a confocal microscope. The density of living cells in the gel was demonstrated by in situ fluorescence staining, and greatly increased after 28 days culture in vitro compared with that of 6 days. No dead cells were found as demonstrated by the absence of PI staining. FIG. 18 shows the viability after 28 days of culture in vitro.

Figure 19:
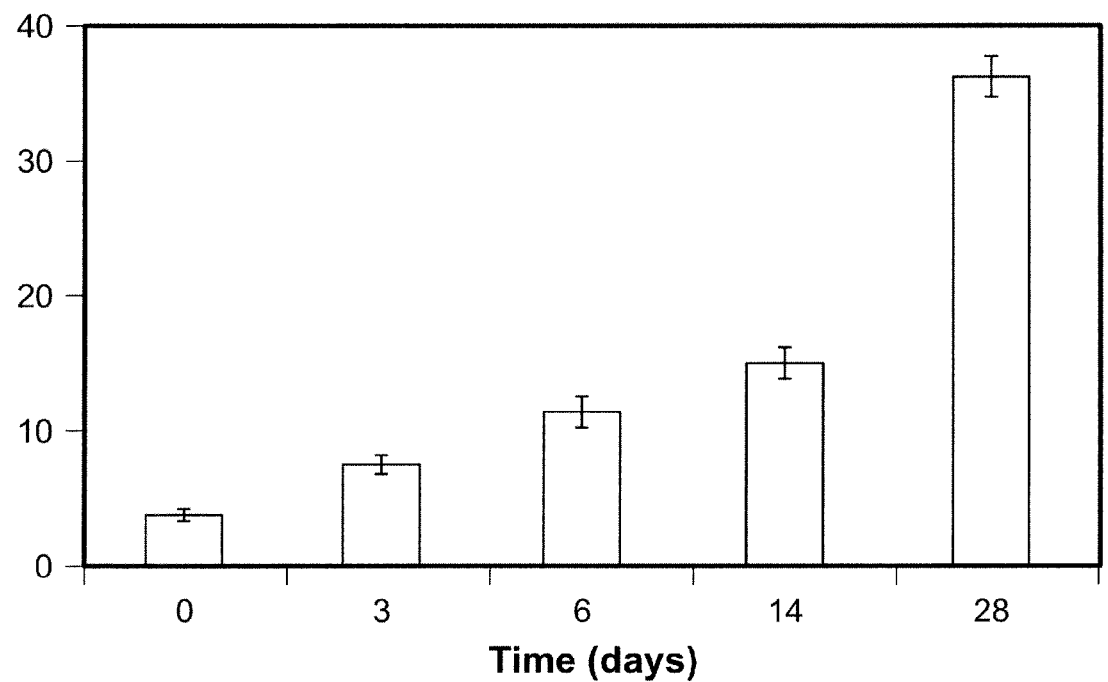
FIG. 19 shows the proliferation of T31 fibroblasts in HA-DTPH-PEGDA gel.

Cell proliferation was determined at day 0, 3, 6, 14, and 28. At each time, four fibroblast-seeded HA-DTPH-PEGDA hydrogels were transferred into each well of a 12-well plate, and rinsed twice with PBS buffer. Next, 900 μl of DMEM/F-12 medium with 5% newborn calf serum and 180 μl of Cell-Titer 96 Proliferation Kit (Promega, Madison, Wis.) were added into each well of a 12-well plate. After 2 hr at 37° C. in a 5% $CO_2$ incubator on an orbital shaker. 125 μl of the solution was transferred into each of six wells of a 96-well plate. Absorbance ($\lambda$=550 nm) was measured using an OPTI Max microplate reader (Molecular Devices, Sunnyvale, Calif.) and was converted into cell number based on a standard curve. The number of fibroblasts in the HA-DTPH-PEGDA hydrogel increased almost tenfold after 28 days of culture in vitro (FIG. 19).

Collagen Typing

At each time point (day 0, 3, 6, 14, and 28), four fibroblast-seeded HA-DTPH-PEGDA hydrogels were minced with 22 gauze needles, digested in 5% cyanogen bromide (CNBr, Sigma) in 70% formic acid (Sigma) for 8 h at 35° C., diluted with same volume of distilled water, and lyophilized overnight. The lyophilized samples were dissolved in PBS buffer and read with Cary 3E spectrophotometer (Varian, Inc., Walnut Creek, Calif.) at 280 nm to determine the protein concentration. Sample buffer containing β-mercaptoethanol was added (50 μg of sample per 20 μl of sample buffer) and aliquots were separated on a 10% PAGE/SDS at 80 v for 8 h plus 300 v for 3 h. The gel was silver stained and collagen peptide fragments were analyzed by comparison with standard collagen type 1 fragments. The collagen typing of these cultured fibroblasts showed that even after 28 days of in vitro culture, the cells retained the same phenotype as characterized by collagen type 1 production.

In vivo implantation of fibroblast-seeded hydrogels. Animal experiments were carried our according to NIH guidelines for the care and use of laboratory animals. Male nude mice (n=12) (Simonsen Laboratories Inc., Gilroy, Calif.), 4-6 weeks old, were reared in the Animal Resources Center at The University of Utah. Under anesthesia, four fibroblast-seeded HA-DTPH-PEGDA hydrogels were implanted bilaterally into subcutaneous pockets surgically prepared in the backs of nude mice. These served as the experimental group, including 24 implants in 6 nude mice, following an approved IACUC protocol. Six additional nude mice received 24 non-cell-loaded HA-DTPH-PEGDA hydrogels as the control group. At each time point (2.4, and 8 weeks after implantation), four nude mice (two experimentals and two controls) were sacrificed and the specimens were dissected for macrographical and immunohistochemical (anti-fibronectin) evaluation.

Figure 20:
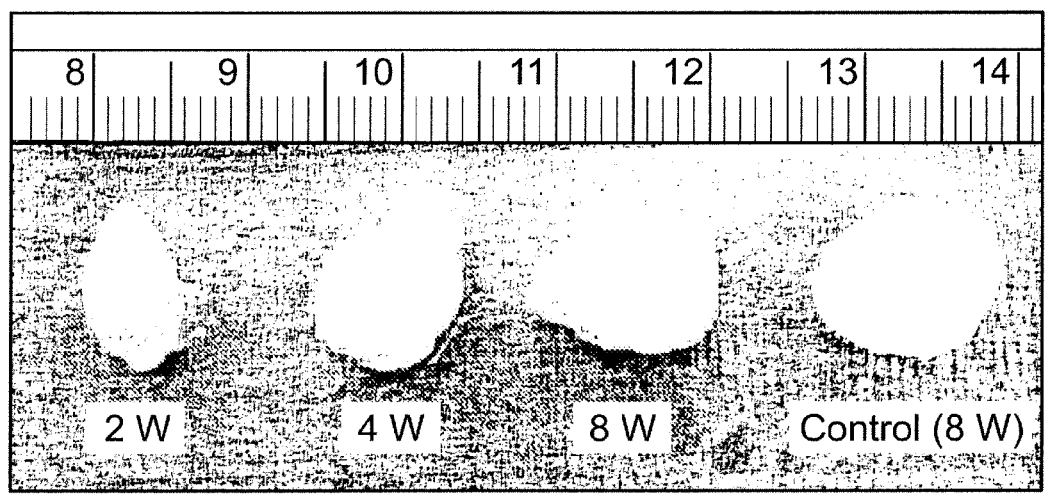
FIG. 20 shows the gross view of explants of HA-DTPH-PEGDA seeded with T31 fibroblasts after subcutaneous implantation in vivo in nude mice.
Figure 21:
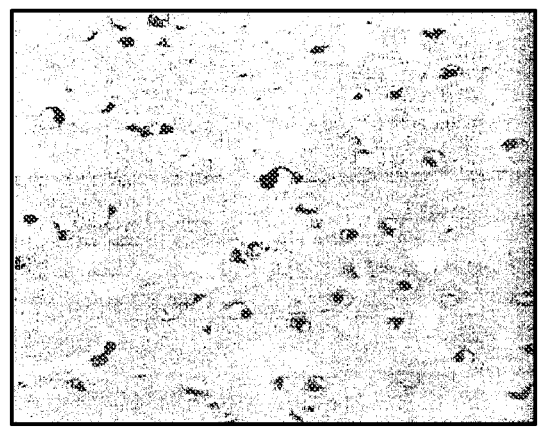
FIG. 21 shows the histological examination of the explants after incubation in nude mice for 2 weeks (Panel A), 4 weeks (Panel B), and 8 weeks (Panel C), immunohistochemistry (fibronectin). Original magnification ×200.
Figure 21:
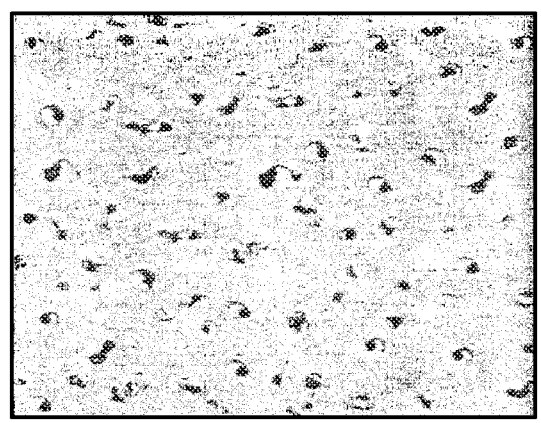
Figure 21:
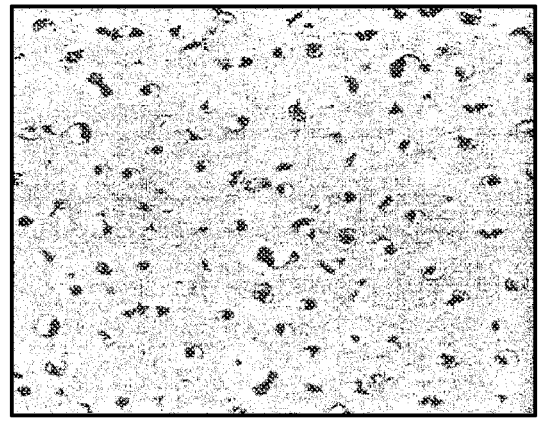

After removal from the mice, the explants appeared more opalescent and elastic with increasing implantation time, suggesting increased cell density (FIG. 20). The gross examination was confirmed by histology (FIG. 21), by staining for fibronectin production. In controls, after 8 weeks of implantation in nude mice, there was no new fibrous tissue formed. In the experimentals, little new fibrous tissue was observed, likely because the cell density for initial seeding was too low, and cell attachment and proliferation factors were added to the implanted gel. Burdick and Anseth (Burdick, J A and Anseth K S. Photoencapsulation of osteoblasts, in injectable RGD-modified PEG hydrogel for bone tissue engineering. Biomaterials 2002:23:4315-4323) photoencapsulated osteoblasts, man injectable RGD-modified PEG hydrogel for bone tissue engineering. However the cell number decreased following two weeks culture in vitro. In our case. T31 fibroblast increased tenfold after 28 days in vitro culture, which indicated the injectable hydrogel described here was excellent candidate for tissue regeneration.

V. Preparation of Mitomycin C Hydrogel Films

Synthesis of MMC-acrylate. Mitomycin C (2 mg) was dissolved in 10 ml dried methylene chloride, and 1.7 μl TEA and 1 μl distilled acryloyl chloride were added consecutively (FIG. 22). The reaction mixture was stirred at room temperature for 4 hours, then concentrated and purified by a silica column (methylene chloride:methanol=20:1). The yield is 1.78 mg. $^1$H NMR (400 MHz, MeOD-d3): δ 6.31 (dd, J=2, J=10, 2'-H), 5.82 (dd, J=10, J=2.4, 1H. 3'-H), 5.48 (d, J=0.8, 1H, 3'-H), 4.81 (dd, obscured by MeOH, 1H, 10-H), 4.49 (d, J=13, 1H, 3-H), 3.93 (t, J=11, 1H, 3-H), 3.67 (d, J=4.4, 1H, 10-H), 3.64 (d, J=4.8, 1H, 9-H), 3.51 (d, J=12, 1H, 1-H), 3.48 (dd, J=1.2, J=4.8, 1H, 2-H), 3.24 (s, 3H, 9a-OCH$_3$), 1.75 (s, 3H, 6-CH$_3$). $^{13}$C NMR (400 MHz, MeOD-d3): δ 177.7 (C-1'), 176.1 (C-5), 176.0 (C-8), 158.4 (CONH$_2$), 155.4 (C-4a), 149.7 (C-7), 130.4 (C-2'), 129.4 (C-3'), 109.9 (C-8a), 106.0 (C-9a), 103.8 (C-6), 61.5 (C-10), 53.6 (C-9), 49.0 (9a-OCH$_3$), 48.9 (C-3), 42.3 (C-1), 40.9 (C-2). 6.9 (6-CH$_3$).

Preparation of MMC-HA.

Model reaction of MMC-acrylate react with thiol group:

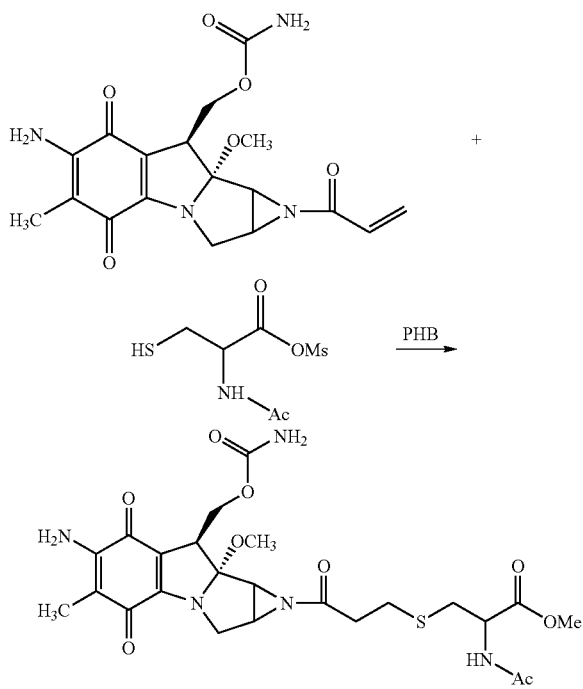

The reaction time of MMC-acrylate conjugate to thiol modified HA was derived by a model reaction. Double protected cysteine was used as a model reagent to react with MMC-acryloyl. The concentration of thiol group was measured using 2-nitro-5-thiosulfobenzoate (NTSB) or Ellman reagent. The reaction was performed in PBS buffer (pH 8.0) with a concentration of MMC-acrylate of 0.3 mg/mL and an initial ratio of 2 acrylates to 1 thiol.

Preparation of HA-MMC Conjugate

Thiol-modified HA was prepared using the hydrazide technology described above. Briefly, low molecular weight HA (200 k Da) was reacted with 3,3'-dithiobis propanoic hydrazide (DTPH) at pH 4.75 by the carbodiimide-catalysed reaction. The gel like product was reduced by solid form DTT, after dialysis, the thiolated HA derivatives were prepared with different loadings. HA-DTPH was dissolved in PBS buffer to the concentration of 1.25% (w/v). Modified MMC was dissolved in minimal ethanol and added into the HA-DTPH solution. The theoretical MMC loading to the disaccharides was 0.5%, 1% and 2% respectively. The procedure was conducted under N$_2$ protection and the final pH of the mixture was adjusted to 8.0. The reaction was processed for three hours with stirring. FIG. 22 depicts the reaction sequence.

Preparation of HA-MMC-PEG Hydrogel Films

HA-MMC solution was adjusted to pH 7.4 after the coupling reaction. PEG diacrylate was dissolved in PBS buffer to the concentration of 4.5% (w/v). The two solutions were mixed together and vortexed for one minute. The reaction mixture was removed by Eppendorf® Combitips and added to 2 cm×2 cm dishes, 2 mL/dishes. The hydrogels were formed in about half hour and were evaporated in air to dryness for several days to form the films. FIG. 23 depicts the reaction sequence.

MMC release experiment. Dried hydrogel films were cut into 2 cm squares. The square gel film and the cut off margin were weighed separately, and the MMC contained in each square film was calculated. Each film was dipped into 5 mL 100 mM PBS buffer and shaken gently at 37° C. At each time point. 0.5 mL solution was removed and 0.5 mL fresh PBS buffer was added. The solution containing released MMC was detected at a wavelength of 358 nm. The accumulated concentration of released MMC was plotted as a function of the time.

FIGS. 25a and b show the results of in vitro MMC release results. FIG. 25a shows the absolute released concentration. The released MMC is proportional to the MMC contained in the hydrogel. The relative release pattern is shown in FIG. 25b after repoltting the data. HA films with 1% and 2% MMC loadings have similar release profiles. At the first half hour, about 13% MMC was released from the hydrogel, which may come from two sources: one was the un-coupled MMC, the other was hydrolyzed MMC. Then a slow release pattern was observed with a half-life around 48 hours. The release of MMC continued for 5 days until reaching a platform. There were still a considerable amount of MMC embedded in the film after 8 days. These results indicate that the newly synthesized HA-MMC-PEG hydrogel has similar hydrolysis kinetics as the described MMC-TA conjugate.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

The invention claimed is:

1. A compound corresponding to formula (I)

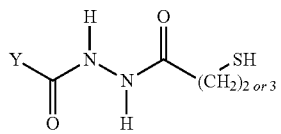

wherein Y is a residue of a protein selected from the group consisting of an extracellular matrix protein, a chemically-modified extracellular matrix protein, and a partially hydrolyzed derivative of an extracellular matrix protein.

2. The compound of claim 1, wherein the protein is collagen or gelatin.

3. The compound of claim 2, wherein the protein is collagen.

4. The compound of claim 1, corresponding to the formula:

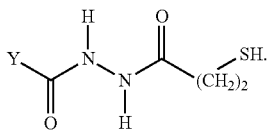

5. The compound of claim 4, wherein the protein is either an extracellular matrix protein or a partially hydrolyzed derivative of an extracellular matrix protein.

6. The compound of claim 5, wherein the protein is collagen or gelatin.

7. The compound of claim 1, corresponding to the formula:

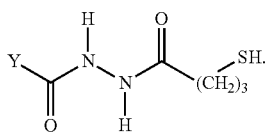

8. The compound of claim 7, wherein the protein is either an extracellular matrix protein or a partially hydrolyzed derivative of an extracellular matrix protein.

9. The compound of claim 8, wherein the protein is collagen or gelatin.

* * * * *

UNITED STATES PATENT AND TRADEMARK OFFICE
CERTIFICATE OF CORRECTION

| | | |
|---|---|---|
| PATENT NO. | : 7,928,069 B2 | Page 1 of 1 |
| APPLICATION NO. | : 12/244135 | |
| DATED | : April 19, 2011 | |
| INVENTOR(S) | : Prestwich et al. | |

It is certified that error appears in the above-identified patent and that said Letters Patent is hereby corrected as shown below:

In the specification

Column 1, lines 19 through 22: change "The research leading to this invention was funded in part by the National Institutes of Health, Grant No. NIH 5R01 DC04663. The U.S. Government may have certain rights on this invention." to --This invention was made with government support under Grant Number R01 DC004663 awarded by the National Institutes of Health. The government has certain rights in the invention.--

Signed and Sealed this
Twenty-fourth Day of May, 2016

Michelle K. Lee
*Director of the United States Patent and Trademark Office*